(12) United States Patent
Tachdjian et al.

(10) Patent No.: US 8,784,782 B2
(45) Date of Patent: Jul. 22, 2014

(54) COMPOUNDS COMPRISING LINKED HETEROARYL MOIETIES AND THEIR USE AS NOVEL UMAMI FLAVOR MODIFIERS, TASTANTS AND TASTE ENHANCERS FOR COMESTIBLE COMPOSITIONS

(75) Inventors: Catherine Tachdjian, San Diego, CA (US); Marketa Lebl-Rinnova, San Diego, CA (US); David Wallace, San Diego, CA (US)

(73) Assignee: Senomyx, Inc., La Jolla, CA (US)

( * ) Notice: Subject to any disclaimer, the term of this patent is extended or adjusted under 35 U.S.C. 154(b) by 86 days.

(21) Appl. No.: 13/616,585

(22) Filed: Sep. 14, 2012

(65) Prior Publication Data

US 2013/0071536 A1 Mar. 21, 2013

Related U.S. Application Data

(63) Continuation of application No. 11/349,071, filed on Feb. 6, 2006.

(60) Provisional application No. 60/650,029, filed on Feb. 4, 2005.

(51) Int. Cl.
| | |
|---|---|
| A61K 8/00 | (2006.01) |
| A61K 8/18 | (2006.01) |
| A61Q 11/00 | (2006.01) |
| A01N 43/64 | (2006.01) |
| A61K 31/41 | (2006.01) |
| A61K 9/00 | (2006.01) |
| A61K 31/395 | (2006.01) |

(52) U.S. Cl.
CPC ............. *A61K 9/0056* (2013.01); *A61K 31/395* (2013.01)
USPC ............................................. 424/49; 514/359

(58) Field of Classification Search
CPC ........................... A61K 9/0056; A61K 31/395
USPC ............................................. 424/49; 514/359
See application file for complete search history.

(56) References Cited

U.S. PATENT DOCUMENTS

| | | |
|---|---|---|
| 3,294,544 A | 12/1966 | Stanko et al. |
| 3,503,962 A | 3/1970 | Beregi et al. |
| 3,535,335 A | 10/1970 | Beregi et al. |
| 3,625,949 A | 12/1971 | Schorre et al. |
| 4,034,109 A | 7/1977 | Rowsell et al. |
| 4,091,018 A | 5/1978 | Asato |
| 4,136,163 A | 1/1979 | Watson et al. |
| 4,150,052 A | 4/1979 | Watson et al. |
| 4,177,279 A | 12/1979 | Archibald et al. |
| 4,332,724 A | 6/1982 | Bentley et al. |
| 4,535,084 A | 8/1985 | Lombardino et al. |
| 4,645,678 A | 2/1987 | Nofre et al. |
| 4,810,715 A | 3/1989 | Schickaneder et al. |
| 4,997,667 A | 3/1991 | Nofre et al. |
| 5,780,090 A | 7/1998 | Frerot et al. |
| 5,877,218 A | 3/1999 | Herzig et al. |
| 5,877,221 A | 3/1999 | Cohen et al. |
| 5,880,159 A | 3/1999 | Herzig et al. |
| 5,914,349 A | 6/1999 | Cohen et al. |
| 5,994,408 A | 11/1999 | Cohen et al. |
| 6,271,263 B1 | 8/2001 | Sklarz et al. |
| 6,277,395 B1 | 8/2001 | Fukui et al. |
| 6,383,778 B1 | 5/2002 | Zuker et al. |
| 6,417,370 B1 | 7/2002 | Lieb et al. |
| 6,429,207 B1 | 8/2002 | Van Wagenen et al. |
| 6,451,843 B1 | 9/2002 | Lieb et al. |
| 6,462,148 B1 | 10/2002 | Suzuki et al. |
| 6,528,685 B2 | 3/2003 | Cohen et al. |
| 6,617,351 B1 | 9/2003 | Arnold et al. |
| 6,818,747 B2 | 11/2004 | Yao et al. |
| 6,906,078 B2 | 6/2005 | Moorman et al. |
| 2001/0047038 A1 | 11/2001 | Moorman et al. |
| 2002/0128433 A1 | 9/2002 | Yao et al. |
| 2002/0132273 A1 | 9/2002 | Stryer et al. |
| 2002/0143151 A1 | 10/2002 | Yao et al. |
| 2002/0160424 A1 | 10/2002 | Adler et al. |
| 2003/0008344 A1 | 1/2003 | Adler et al. |
| 2003/0054448 A1 | 3/2003 | Adler et al. |
| 2003/0089885 A1 | 5/2003 | Rogers et al. |
| 2003/0139470 A1 | 7/2003 | Peter et al. |

(Continued)

FOREIGN PATENT DOCUMENTS

| | | |
|---|---|---|
| EP | 0055689 A1 | 7/1982 |
| EP | 0413162 A2 | 2/1991 |

(Continued)

OTHER PUBLICATIONS

Biagi et al (Euro. Jor. of Med. Chem, vol. 38 No. 11-12, 2003, 983-990.*

(Continued)

*Primary Examiner* — Benjamin Packard
(74) *Attorney, Agent, or Firm* — Cooley LLP

(57) ABSTRACT

The inventions disclosed herein relate to the discovery of the use of compounds having the formula shown below

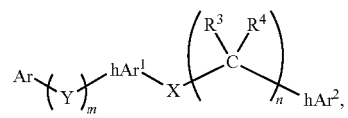

and certain subgenera or species thereof, as flavor or taste modifiers, particularly, savory ("umami") taste modifiers, savory flavoring agents and savory flavor enhancers in foods, beverages, and other comestible compositions.

27 Claims, No Drawings

(56) References Cited

U.S. PATENT DOCUMENTS

| | | |
|---|---|---|
| 2003/0170608 A1 | 9/2003 | Pronin et al. |
| 2003/0207337 A1 | 11/2003 | Han et al. |
| 2003/0220479 A1 | 11/2003 | Li et al. |
| 2003/0228633 A1 | 12/2003 | Zoller et al. |
| 2003/0232407 A1 | 12/2003 | Zoller et al. |
| 2004/0072254 A1 | 4/2004 | Callamaras et al. |
| 2004/0086553 A1 | 5/2004 | Shinohara et al. |
| 2004/0132075 A1 | 7/2004 | Elliot et al. |
| 2004/0132134 A1 | 7/2004 | Adler et al. |
| 2004/0171042 A1 | 9/2004 | Adler et al. |
| 2004/0175792 A1 | 9/2004 | Zoller et al. |
| 2004/0175793 A1 | 9/2004 | Zoller et al. |
| 2004/0185469 A1 | 9/2004 | Zoller et al. |
| 2004/0191805 A1 | 9/2004 | Adler et al. |
| 2004/0191862 A1 | 9/2004 | Zoller et al. |
| 2004/0209286 A1 | 10/2004 | Adler et al. |
| 2004/0229239 A1 | 11/2004 | Adler et al. |
| 2005/0032158 A1 | 2/2005 | Adler et al. |
| 2005/0069944 A1 | 3/2005 | Adler |
| 2005/0084506 A1 | 4/2005 | Tachdjian et al. |
| 2005/0084932 A1 | 4/2005 | Zoller et al. |
| 2006/0045953 A1 | 3/2006 | Tachdjian et al. |
| 2006/0263411 A1 | 11/2006 | Tachdjian et al. |
| 2013/0071536 A1 | 3/2013 | Tachdjian et al. |

FOREIGN PATENT DOCUMENTS

| | | |
|---|---|---|
| EP | 0656350 A1 | 6/1995 |
| EP | 0854134 A1 | 7/1998 |
| EP | 0976744 A1 | 2/2000 |
| EP | 1142490 A1 | 10/2001 |
| EP | 1205116 A2 | 5/2002 |
| EP | 1500650 A1 | 1/2005 |
| GB | 1457671 | 12/1976 |
| GB | 1502680 | 3/1978 |
| GB | 1489359 | 10/1997 |
| JP | 50-64235 A | 5/1975 |
| JP | 54-122773 A | 9/1979 |
| JP | 61-148176 A | 7/1986 |
| JP | 4-8264 A | 1/1992 |
| JP | 9-173008 A | 7/1997 |
| JP | 10-507086 A | 7/1998 |
| JP | 11-313635 A | 11/1999 |
| JP | 2000-169438 A | 6/2000 |
| JP | 2000-175650 A | 6/2000 |
| JP | 2005-500318 A | 1/2005 |
| WO | WO 95/18617 A1 | 7/1995 |
| WO | WO 96/21640 A1 | 7/1996 |
| WO | WO 97/04667 A1 | 2/1997 |
| WO | WO 98/32733 A1 | 7/1998 |
| WO | WO 99/07235 A1 | 2/1999 |
| WO | WO 99/26927 A2 | 6/1999 |
| WO | WO 00/06156 A1 | 2/2000 |
| WO | WO 00/63166 A1 | 10/2000 |
| WO | WO 01/35768 A1 | 5/2001 |
| WO | WO 01/77292 A2 | 10/2001 |
| WO | WO 01/77676 A1 | 10/2001 |
| WO | WO 01/79204 A1 | 10/2001 |
| WO | WO 02/06254 A1 | 1/2002 |
| WO | WO 02/36622 A2 | 5/2002 |
| WO | WO 02/064139 A1 | 8/2002 |
| WO | WO 02/064631 A2 | 8/2002 |
| WO | WO 02/078696 A1 | 10/2002 |
| WO | WO 03/001876 A2 | 1/2003 |
| WO | WO 03/013517 A1 | 2/2003 |
| WO | WO 03/037332 A1 | 5/2003 |
| WO | WO 03/070713 A1 | 8/2003 |
| WO | WO 04/000355 A1 | 12/2003 |
| WO | WO 2004/011617 A2 | 2/2004 |
| WO | WO 2004/026840 A1 | 4/2004 |
| WO | WO 2004/080976 A1 | 9/2004 |
| WO | WO 2004/081018 A1 | 9/2004 |
| WO | WO 2004080976 A1 * | 9/2004 |
| WO | WO 2004/089470 A2 | 10/2004 |
| WO | WO 2004/092182 A1 | 10/2004 |
| WO | WO 2004/113304 A1 | 12/2004 |
| WO | WO 2005/015158 A2 | 2/2005 |
| WO | WO 2005/041684 A2 | 5/2005 |
| WO | WO 2006/084184 A2 | 8/2006 |

OTHER PUBLICATIONS

Adler et al., "A Novel Family of Mammalian Taste Receptors," Cell, 100(6):693-702 (2000).

Ager et al., "Commercial, Synthetic Nonnutritive Sweeteners," Angew. Chem. Int. Ed., 37:1802-1817 (1998).

Ahn et al., "A General Diastereoselective Synthesis of Spiroacetals Related to Those in Ionophores via the Reaction of Lacones with Cerium(III) γ-Cerioalkoxide. MAD Reverses the Diastereoselectivity of the Addition of Methylmetallics to a β-Keto Ether," J. Org. Chem., 59:3142-3150 (1994).

Amantini et al., "TBAF-Catalyzed Synthesis of 5-Substituted 1H-Tetrazoles under Solventless Conditions," J. Org. Chem., 69(8):2896-2898 (2004).

Antti, "International Search Report," 9 pages, PCT appl. no. PCT/US2006/003956, European Patent Office (mailed Oct. 19, 2006).

Antti, "Written Opinion of the International Searching Authority," 10 pages, PCT appl. no. PCT/US2006/003956, European Patent Office (mailed Oct. 19, 2006).

Appukkuttan et al., "A Microwave-Assisted Click Chemistry Synthesis of 1,4-Disubstituted 1,2,3-Triazoles via a Copper(I)-Catalyzed Three-Component Reaction," Org. Letters, 6(23):4223-4225 (2004).

Ashton et al., "Renin Inhibitors Containing C-Termini Derived From Mercaptoheterocycles," J. Med. Chem., 35(11):2103-2112 (1992).

Berge et al., "Pharmaceutical Salts," J. Pharm. Sci., 66:1-19 (1977).

Biagi et al., "$N^6$-Cycloalkyl-2-phenyl-3-deaza-8-azaadenines: a new class of $A_1$ adenosine receptor ligands. A comparison with the corresponding adenines and 8-azaadenines," European Journal of Medicinal Chemistry, 38:983-990 (2003).

Bors et al., "Antioxidant Mechanisms of Polyphenolic Caffeic Acid Oligomers, Constituents of Salvia officinalis," Bio. Res., 37:301-311 (2004).

Chandrashekar et al., "T2Rs Function as Bitter Taste Receptors," Cell, 100:703-711 (2000).

Clark et al., "Synthesis and Analgesic Activity of 1,3-Dihydro-3-(substituted phenyl)imidazo[4,5-b]pyridine-2-ones and 3-(Substituted phenyl)-1,2,3,-triazolo[4,5,-b]pyridines," Journal of Medicinal Chemistry, 21 (9):965-968 (1978).

Contreras et al., "Design, Synthesis, and Structure-Activity Relationships of a Series of 3-[2-(1-Benzylpiperidin-4-yl)ethylamino]pyridazine Derivatives as Acetylcholinesterase Inhibitors," J. Med. Chem. 44(17):2707-2718 (2001).

Crosignani et al., "Polymer-Supported Mukaiyama Reagent: A Useful Coupling Reagent for the Synthesis of Esters and Amides," Organic Letters, 6(24):4579-4582 (2004).

Darses et al., "Palladium-Catalyzed Cross-Coupling Reactions of Arenediazonium Tetrafluoroborates with Aryl- and Alkenylboronic Acids," Bull. Soc. Chem. Fr., 133:1095-1102 (1996).

Date et al., "Reactions of Lithiated ortho-Toluamides and Related Compounds with Vinysilanes: Synthesis of 1-Tetralones and 1-Naphtols," S. Chem. Pharm. Bull., 38(4):902-906 (1990).

Evangelista et al., "Sintesi Ed Attivita Antiulcera Di Alcuni Nuovi Composti a Struttura Ariltiometil-Piridinica," Farmaco; Edizione Scientifica, Societa Chimica Italiana, Pavia, IT, 43(11):901-908 (Nov. 1988) (English abstract included, reference may disclose arguably material compounds).

Firooznia et al., "Enantioselective Synthesis of 4-Substituted Phenylalanines by Cross-Coupling Reactions," Tetrahedron Letters, 40:213-216 (1999).

Gawley et al., "(R,R)-1,3-Dibenzylisoindoline: A New C2-Symmetric Secondary Amine, by Stereoselective and Regioselective α,d-Dialkylation of Isoindoline, and an Improved Procedure for the Preparation of Isoindoline," J. Org. Chem., 53:5381-5383 (1988).

Higuchi et al., "4-Alkyl-and 3,4-Dialkyl-1,2,3,4-Tetrahydro-8-Pyridono[5,6-g]Quinolines: Potent, Nosteroidal Androgen Receptor Agonists," Bioorganic & Medicinal Chemistry Letters, 9:1335-1340 (1999).

(56) References Cited

OTHER PUBLICATIONS

Huang et al., "2-{2[3-(Pyridin-3-yloxy)phenyl]-2H-tetrazol-5-yl} pyridine: a highly potent, orally active, metabotropic glutamate subtype 5 (mGlu5) receptor antagonist," Bioorg. Med. Chem. Lett. 14(22):5473-5476 (2004).
Huffman et al., "n-Cyanoimdates," J. Org. Chern., 28:1816-1821 (1963).
Indolese, "Suzuki-Type Coupling of Chloroarenes with Arylboronic Acids Catalysed by Nickel Complexes," Tetrahedron Letters, 38:3513-3516 (1997).
Jasiczk et al., "Structure-Activity Relationship of Sweet Molecules: Phenylurea Derivatives," Polish J. Chem. 74:1259-1273 (2000).
Kelp Soup. http://web.archive.org/web/20020602200005/http://www.innerself.com/recipes/soups/Kelp_Soup.htm. Archived Jun. 2, 2002. Accessed Apr. 22, 2009.
Kinghorn et al., "Noncariogenic Intense Natural Sweeteners," Med. Res. Rev., 18(5):347-360 (1998).
Kinoshita et al., "Chalcogeno Morita-Baylis-Hillman Reaction of 2-(Methylchalcogeno)phenyl Vinyl Ketones with Aldehyds, Ketones, and α-Dicarbonyl Compunds," Eur. J. Org. Chem., 4852-4861 (2003).
Li et al., "Human Receptors for Sweet and Umami Taste," PNAS, 99(7):4692-4696 (2002).
Linton et al., "Acyl Dipeptides as Reversible Caspase Inhibitors. Part 1: Initial Lead Optimization," Bioorganic & Medicinal Chemistry Letters, 12:2969-2971 (2002).
Littke et al., "A Convenient and General Method for Pd-Catalyzed Suzuki Cross-Couplings of Aryl Chlorides and Arylboronic Acids," Angew. Chem. Int. Ed., 37:3387-3388 (1998).
Marcus, "Culinary Applications of Flavor Enhancement in Product Development," Slide Presentation Annual Meeting of Institute of Food Technology, Las Vegas, Nevada, Jul. 12-16, 2004.
Matsunami et al., "A Family of Candidate Taste Receptors in Human and Mouse," Nature, 404:601-604 (2000).
Maxwell et al., "Synthesis of 5-aryl-2H-tetrazoles, 5-aryl-2H-tetrazole-2-acetic acids, and [(4-phenyl-5-aryl-4H-1,2,4-triazol-3-yl)thio]acetic acids as possible superoxide scavengers and antiinflammatory agents," J. Med. Chern., 27(12):1565-1570 (1984).
McMurry, "Isoxazole Annelation Reaction: 1-Methyl-4,4a,5,6,7,8-Hexahydronaphthalen-2(3H)-One," Org. Syn. Coll., vol. 6, p. 781; vol. 53, p. 70, (1973).
misosouprecipe. http://www.geocities.com/japanese_gifts_online/japanese_recipe/clear_miso_soup.html. Copyright 1997-2003. Accessed Apr. 22, 2009.
Miyaura et al., "Palladium-Catalyzed Cross-Coupling Reactions of Organoboron Compounds," Chem. Rev. 95:2457-2483 (1995).
Montmayeur et al., "A Candidate Taste Receptor Gene Near a Sweet Taste Locus," Nature Neuroscience, 4(5):492-498 (2001).
Morini et al., "From Small Sweeteners to Sweet Proteins: Anatomy of the Binding Sites of the Human T1R2_T1R3 Receptor," J. Med. Chem., 48(17):5520-5529 (Aug. 2005).
Musser et al., "Synthesis and Antiallergic Activities of 1,3-Oxazolo[4,5-h]quinolines," J. Med. Chem., 28:1255-1259 (1985).
Naito et al., "Synthesis and Pharmacological Activity of Triazole Derivatives Inhibiting Eosinophilia," J. Med. Chern., 39(15);3019-3029 (1996).
Nelson et al., "Mammalian Sweet Taste Receptors," Cell, 106: 381-390 (2001).
Noyes et al., "Phthalimide," Organic Syntheses, Coll. vol. 1, p. 457; vol. 2, p. 75, 1941 and 1922.

Office Action issued in related Austrlaian Patent Application No. 2006210513, mailed on Jun. 22, 2010.
Oshiro et al., "Novel Cerebroprotective Agents with Central Nervous System Stimulating Activity. 1. Synthesis and Pharmacology of 1-Amino 7-hydroxyindan Derivatives, " J. Med. Chem., 34:2004-2013 (1991).
Patonay et al., "Chemo—and Diastereoselectivity in the Dimethyldioxirane Oxidation of 2,3-Dihydro-4H-1-benzothiopyran-4-ones and 4H-1-Benzothiopyran-4-ones. Unusual Reactivity of 4H-1-Benzothiopyran-4-one 1-Oxides[1]," J. Org. Chem. 66:2275-2280 (2001).
Pernak et al., "Activity of new quaternary ammonium compounds on strains of bacteria and fungi. Part 5: Synthesis of 3-Methyl-N-Alkylthiomethylpyridine-, 1-Methyl-3-N-Alkylthiomethylimidazole—and 1-Ethyl-3-N-Alkylthiolimid Azoline Chlorides," Pharmazie, Die, Govi Verlag, Eschborn, DE, 38(11):752-754 (1983) (English abstract included, reference may disclose arguably material compounds).
Sarges et al., "5,8-Diubstituted 1-Aminotetralins. A Class of Compounds with a Novel Profile of Central Nervous System Activity," Journal of Medicinal Chemistry, 16(9):1003-1011 (1973).
Sato et al., "New Synthesis of Dimethyl N-Aroylcarbimidodithioates and 3-Aryl-5-methylthio-1H-1,2,4-triazoles," Synthesis, 7:554-557 (1981).
Sayed et al., "The Use of 4-(3,4-Dichlorophenyl)-4-Oxo-2-(4-Antipyrinyl)-Butanoic Acid in the Preparation of Some New Heterocyclic Compounds With Expected Biological Activity," Molecules, 8:322-332(2003).
Skupinska et al., "Concise Preparation of Amino-5,6,7,8-tetrahydroquinolines and Amino-5,6,7,8-tetrahydroisoquinolines via Catalytic Hydrogenation of Acetamidoquinolines and Acetamidoisoquinolines," J. Org. Chem., 67:7890-7893 (2002).
Skupinska et al., "Enzymatic Resolution of Bicyclic 1-Heteroarylamines using Candida antarcticai Lipase B," J. Org. Chem., 68(9):3546-3551 (2003).
Smith et al., "GRAS Flavoring Substances 21," Food Technology, 57(5):46-59 (2003).
Stalker et al., "Asymmetric Synthesis of Two New Conformationally Constrained Lysine Derivatives," Tetrahedron, 58:4837-4849 (2002).
Suzuki, "New Synthetic Transformations Via Organoboron Compounds," Pure & Applied Chem., 66:213-222 (1994).
Swallowing problems. http://my.clevelandclinic.org/healthy_living/nutrition/hic_nutrition_problems_and_their_solutions.aspx. Archived Feb. 1, 2001.
Szczepankiewicz et al., "New Antimitotic Agents with Activity in Multi-Drug-Resistant Cell Lines and in Vivo Efficacy in Murine Tumor Models," J. Med. Chern., 44(25):4416-4430 (2001).
Thate, "The Relationship Between Constitution and Taste Among Some Derivatives of Urea," Recueil Des Travaux Chimiques Des Pays-Bas et de La Belgique 48:116-120 (1929).
Turnbull et al., "Disposition and Metabolism of 4-Methyl-2-(4-phenylbenzyl)-2-oxazoline-4-methanol in the Rat and Dog," Journal of Medicinal Chemistry, 17(1):45-48 (1974).
Vivona et al., "Photoinduced Molecular Rearrangements. The Photochemistry of 1,2,4,-oxadiazoles in the Presence of Sulphur Nucleophiles. Synthesis of 1,2,4,-thiadiazoles," Tetrahedron, 53(37): 12629-12636 (1997).
Watanabe et al., "Synthesis of Sterically Hindered Biaryls via the palladium-Catalyzed Cross-Coupling Reaction of Arylboronic Acids or Their Esters With Haloarenes," Synlett., 207-210 (1992).

\* cited by examiner

US 8,784,782 B2

COMPOUNDS COMPRISING LINKED HETEROARYL MOIETIES AND THEIR USE AS NOVEL UMAMI FLAVOR MODIFIERS, TASTANTS AND TASTE ENHANCERS FOR COMESTIBLE COMPOSITIONS

RELATED APPLICATIONS

The present application is a continuation of U.S. patent application Ser. No. 11/349,071, filed on Feb. 6, 2006, which claims the priority of U.S. provisional patent application Ser. No. 60/650,029 filed Feb. 4, 2005, the entire disclosure of which is hereby incorporated herein by this reference, for all purposes.

FIELD OF THE INVENTION

The present invention relates to the discovery of flavor or taste modifiers, such as a flavoring or flavoring agents and flavor or taste enhancers, more particularly, savory ("umami") taste modifiers, savory flavoring agents and savory flavor enhancers, for foods, beverages, and other comestible compositions.

BACKGROUND OF THE INVENTION

For centuries, various natural and unnatural compositions and/or compounds have been added to foods, beverages, and/or comestible (edible) compositions to improve their taste. Although it has long been known that there are only a few basic types of "tastes" (sweet, sour, bitter, salty, and "umami"/savory), the biological and biochemical basis of taste perception was poorly understood, and most taste improving or taste modifying agents have been discovered largely by simple trial and error processes.

For example, one of the five known basic tastes is the "savory" or "umami" flavor of monosodium glutamate ("MSG"), which is now commonly added to many food and beverage compositions to desirably improve their "savory" flavor. MSG is known to produce adverse reactions in some people, but very little progress has been made in identifying artificial substitutes for MSG. It is known that a few naturally occurring materials can increase or enhance the effectiveness of MSG as a savory flavoring agent, so that less MSG is needed for a given flavoring application. For example the naturally occurring nucleotide compounds inosine monophosphate (IMP) or guanosine monophosphate (GMP) are known to have a synergistic and/or multiplier effect on the savory taste of MSG. Nevertheless, IMP and GMP are difficult and expensive to isolate and purify from natural sources, or synthesize, and hence have limited practical application to many commercial needs in food compositions. Less expensive compounds that would provide and/or replace the flavor of MSG itself, or multiply the effectiveness of any MSG that is present so as to replace the need for the addition of IMP or GMP additives could be of very high value, especially if the compounds could be used at extremely low concentrations, so as to minimize costs and any possible health risks.

In recent years substantial progress has been made in biotechnology in general, and in better understanding the underlying biological and biochemical phenomena of taste perception. For example, taste receptor proteins have been recently identified in mammals which are involved in taste perception. Particularly, two different families of G protein coupled receptors believed to be involved in taste perception, T2Rs and T1Rs, have been identified. (See, e.g., Nelson, et al., *Cell* (2001) 106(3):381-390; Adler, et al., *Cell* (2000) 100(6):693-702; Chandrashekar, et al., *Cell* (2000) 100:703-711; Matsunami, et al., *Number* (2000) 404:601-604; Li, et al., *Proc. Natl. Acad. Sci. USA* (2002) 99:4962-4966; Montmayeur, et al., *Nature Neuroscience* (2001) 4(S):492-498: U.S. Pat. No. 6,462,148; and PCT publications WO 02/06254, WO 00/63166 art, WO 02/064631, and WO 03/001876, and U.S. Patent publication US 2003-0232407 A1). The entire disclosures of the articles, patent applications, and issued patents cited immediately above are hereby incorporated herein by reference, for all purposes, including their disclosures of the identities and structures of T2Rs and T1Rs mammalian taste receptor proteins and methods for artificially expressing those receptors in cell lines and using the resulting cell lines for screening compounds as potential "savory" flavoring agents.

Whereas the T2R family includes a family of over 25 genes that are involved in bitter taste perception, the T1Rs only includes three members, T1R1, T1R2 and T1R3. (See Li, et al., *Proc. Natl. Acad. Sci. USA* (2002) 99:4962-4966.) Recently it was disclosed in WO 02/064631 and/or WO 03/001876 that certain T1R members, when co-expressed in suitable mammalian cell lines, assemble to form functional taste receptors. Particularly it was found that co-expression of T1R1 and T1R3 in a suitable host cell results in a functional T1R1/T1R3 savory ("umami") taste receptor that responds to savory taste stimuli, including monosodium glutamate. (See Li, et al. (Id.). The references cited above also disclosed assays and/or high throughput screens that measure T1R1/T1R3 or T1R2/T1R3 receptor activity by fluorometric imaging in the presence of the target compounds.

Very recently, certain U.S. and international patent applications have been filed by some of the current Applicants that disclosed the use of certain amide compounds as umami and/or sweet tastants, and/or synergistic enhancers of the "Umami" taste of MSG, and/or the sweet taste of a variety of natural and artificial sweeteners. See, for example, U.S. Provisional Patent Application Ser. No. 60/494,071 filed Aug. 6, 2003, U.S. Provisional Patent Application Ser. No. 60/552,064 filed Mar. 9, 2004, U.S. Utility patent application Ser. No. 10/913,303, filed Aug. 6, 2004 and published as U.S. Patent Publication Serial No. US-2005-0084506-A1 on Apr. 21, 2005; and PCT Patent Application Serial No. PCT/US04/25419 filed Aug. 6, 2004 and published as PCT Publication WO 2005/041684 on May 12, 2005, and PCT Publication WO 2005/015158 published on Feb. 17, 2005. The entire disclosures of the patent applications cited immediately above are hereby incorporated herein by this reference, for all purposes, including their disclosures of the identities and structures of amide compounds that can serve as potential "savory" or sweet flavoring agents or enhancers. Nevertheless, there is a continuing need for new and improved taste enhancing compounds.

We employed the above-described assays and/or high throughput screening methods to identify from a very large number of initial compounds a very few linked heteroaryl "lead" compounds that modulate the activity of T1R1/T1R3 "savory" taste receptors, then embarked on a long, complex and iterative process of investigation, evaluation and revision, and chemical structural optimization, so as to arrive at the various inventions described below.

SUMMARY OF THE INVENTION

The invention has many aspects, all of which relate to certain non-naturally occurring compounds comprising linked heteroaryl moieties which have the generic structure shown below in Formula (I), and methods for the synthesis of those compounds, and the use of those compounds and commestibly acceptable salts and/or compositions thereof as savory flavoring agents for comestible compositions or one or more of their precursor components. In many embodiments, the invention relates to methods for modulating the savory taste of a comestible product comprising:

a) providing at least one comestible product, or one or more precursors thereof, and
b) combining the comestible product or one or more precursors thereof with at least a savory flavor modulating amount of at least one compound of Formula (I), or a comestibly acceptable salt thereof, so as to form a modified comestible product;

wherein the compound of Formula (I) has the formula:

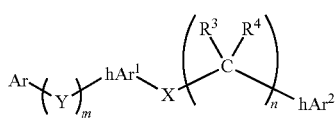

(I)

wherein
i) Ar is an aryl or heteroaryl radical optionally having at least one substituent radical bound thereto;
ii) Y is O, S, S(O), SO$_2$, CR$^1$R$^2$, or NR$^5$;
iii) m is the integer zero or one;
iv) hAr$^1$ is an optionally substituted heteroaryl ring radical;
v) X is O, S, S(O), SO$_2$, CR$^8$R$^9$, or NR$^{10}$;
vi) n the integers zero, one, two, or three;
vii) hAr$^2$ is an optionally substituted heteroaryl ring radical.

In related embodiments of the compounds of Formula (I), hAr$^2$ can be an optionally substituted aryl radical, such as a phenyl radical.

Additional embodiments of the inventions related to the compounds of Formula (I) provide for modified comestible products or compositions comprising one or more of the compounds of Formula (I) or its various subgeneric or species compounds or comestibly acceptable salts thereof, or the products produced by the processes recited above, or below. For example in further related embodiments, the inventions disclosed herein relate to taste modified comestible compositions comprising:

a) at least one comestible product, or one or more precursors thereof, and
b) at least a savory flavor modulating amount of at least one compound having the formula:

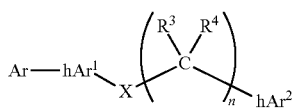

wherein
i) Ar is a monocyclic or bicyclic aryl or heteroaryl radical comprising one or two aromatic rings independently selected from benzene rings and five or six membered heteroaryl rings, each aromatic ring optionally having one, two, or three R$^{20}$ substituent radicals bound thereto, wherein each R$^{20}$ radical is independently selected from hydroxyl, NH$_2$, NO$_2$, SH, SO$_3$H, P(O)(OH)$_2$, halogen, or a C$_1$-C$_4$ organic radical;
ii) hAr$^1$ is an optionally substituted five or six-membered heteroaryl ring radical having from 1 to 4 heteroatoms independently selected from oxygen, sulfur and/or nitrogen, wherein any remaining members of the heteroaromatic ring are independently selected from CR$^6$, N, NR$^7$;
iii) X is O, S, S(O), SO$_2$, CR$^8$R$^9$, or NR$^{10}$;
iv) n the integer zero, one, two, or three;
v) R$^3$, R$^4$, R$^8$ and R$^9$ are independently selected from hydrogen, oxygen, hydroxyl, NH$_2$, SH, halogen, or a C$_1$-C$_4$ organic radical, and R$^7$ and R$^{10}$ are independently selected from hydrogen, hydroxyl, or a C$_1$-C$_4$ organic radical, and R$^6$ is hydrogen, hydroxyl, NH$_2$, NO$_2$, SH, SO$_3$H, P(O)(OH)$_2$, halogen, or a C$_1$-C$_4$ organic radical;
vi) hAr$^2$ is an optionally substituted five or six-membered heteroaryl ring having at least one ring carbon atom and at least one ring nitrogen atom, and wherein the remaining members of the heteroaryl ring are independently selected from CR$^{30}$, N, NR$^{31}$, O, and S, wherein each R$^{30}$ is independently selected from hydrogen, hydroxyl, NH$_2$, NO$_2$, SH, SO$_3$H, P(O)(OH)$_2$, a halogen, or a C$_1$-C$_4$ organic radical, and each R$^{31}$ is independently selected from hydrogen, or a C$_1$-C$_4$ organic radical;

or a comestibly acceptable salt thereof.

In some such embodiments, the inventions relate to sub-genuses of the linked heteroaryl compounds of Formula (I) and their uses in methods for modulating the savory taste of comestible compositions. For example, one sub-genus of the linked heteroaryl compounds has the structure shown in Formula (IA) below:

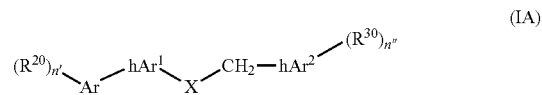

(IA)

wherein
i) n' is the integer zero, one, two, or three, and each R$^{20}$ is independently selected from the group consisting of hydroxy, SH, NH$_2$, a halogen, or a C$_1$-C$_4$ organic radical,
ii) n" is zero, one, two, or three, and each R$^{30}$ is independently selected from the group consisting of hydroxy, SH, NH$_2$, a halogen, or a C$_1$-C$_4$ organic radical,
iii) X is NH, O, S, S(O), SO$_2$, or CH$_2$,
iv) Ar is a phenyl, pyridyl, pyrazinyl, pyrimidinyl, furanyl, thiofuranyl, pyrrolyl, benzofuranyl, benzothiofuranyl, or benzopyrrolyl ring
v) hAr$^1$ has the structure:

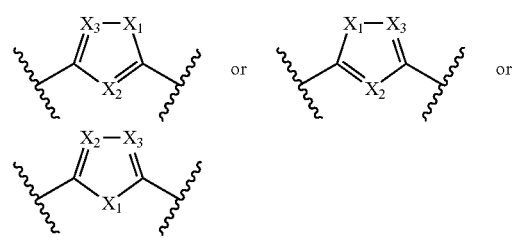

(1) X$_1$ is NH, O, or S,
(2) X$_2$ is N or CR$^6$ wherein R$^6$ is hydrogen, a halogen, or a C$_1$-C$_4$ organic radical,
(3) X$_3$ is N or CR$^6$ wherein R$^6$ is hydrogen, a halogen, or a C$_1$-C$_4$ organic radical, and
vi) hAr$^2$ is a pyridyl, pyrazinyl, or pyrimidinyl ring;
or a comestibly acceptable salt thereof.

Another related sub-genus of the linked heteroaryls of Formula (I), useful as savory flavoring agents, are triazole compounds having the structure shown in Formula (IB) below;

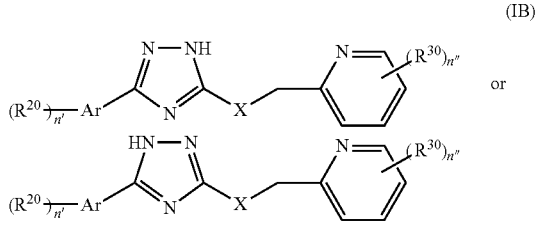

(IB)

wherein
i) n' is zero, one, two, or three, and each $R_{20}$ is independently selected from hydroxy, SH, $NH_2$, a halogen, and a $C_1$-$C_4$ radical selected from an alkyl, alkoxyl, alkoxyalkyl, hydroxyalkyl, haloalkyl, CN, $CO_2H$, CHO, $COR^{21}$, $CO_2R^{21}$, $NHR^{21}$, $NR^{21}R^{21'}$, or $SR^{21}$ radical, wherein $R^{21}$ is an alkyl,
ii) n" is zero, one, two, or three, and each $R_{30}$ is independently selected from hydroxy, SH, $NH_2$, a halogen, and a $C_1$-$C_4$ radical selected from an alkyl, alkoxyl, alkoxyalkyl, hydroxyalkyl, haloalkyl, CN, $CO_2H$, CHO, $COR^{32}$, $CO_2R^{32}NHR^{32}$, $NR^{32}R^{32'}$, or $SR^{32}$ radical, wherein $R^{32}$ is an alkyl,
iii) X is NH, O, S, S(O), $SO_2$, or $CH_2$,
iv) Ar is a phenyl, pyridyl, pyrazinyl, pyrimidinyl, furanyl, thiofuranyl, or pyrrolyl ring;
or a comestibly acceptable salt thereof.

Yet another related sub-genus of the linked heteroaryls of Formula (I) are triazole compounds having the structure shown in Formula (IC) below in which both the X and Y linker groups are present;

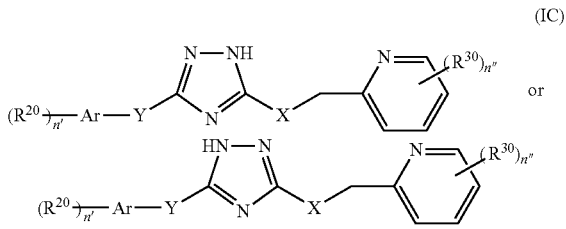

(IC)

wherein
i) n' is zero, one, two, or three, and each $R^{20}$ is independently selected from the group consisting of hydroxyl, SH, $NH_2$, a halogen, or a $C_1$-$C_4$ organic radical,
ii) n" is zero, one, two, or three, and each $R^{30}$ is independently selected from the group consisting of OH, SH, $NH_2$, a halogen, or a $C_1$-$C_4$ organic radical,
iii) X is NH, O, S, S(O), $SO_2$, or $CR^8R^9$, wherein $R^8$ and $R^9$ are independently selected from hydrogen, oxygen, hydroxyl, $NH_2$, a halogen, or a $C_1$-$C_4$ organic radical,
iv) Y is NH, O, S, S(O), $SO_2$, or $CR^8R^9$, wherein $R^8$ and $R^9$ are independently selected from hydrogen, oxygen, hydroxyl, $NH_2$, a halogen, or a $C_1$-$C_4$ organic radical,
v) Ar is a phenyl, pyridyl, pyrazinyl, pyrimidinyl, furanyl, thiofuranyl, or pyrrolyl ring;
or a comestibly acceptable salt thereof.

Yet another related sub-genus of the linked heteroaryls of Formula (I) are compounds having hAr1 heteroaryl rings that are six-membered nitrogen heteroaryls as shown in Formula (ID):

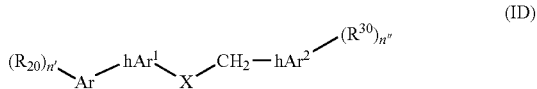

(ID)

wherein
i) n' is zero, one, two, or three, and each $R^{20}$ is independently selected from the group consisting of hydroxy, SH, $NH_2$, a halogen, or a $C_1$-$C_4$ organic radical,
ii) n" is zero, one, two, or three, and each $R^{30}$ is independently selected from the group consisting of hydroxy, SH, $NH_2$, a halogen, or a $C_1$-$C_4$ organic radical,
iii) X is NH, O, S, S(O), $SO_2$, or $CH_2$,
iv) Ar is a phenyl, pyridyl, pyrazinyl, pyrimidinyl, furanyl, thiofuranyl, pyrrolyl, benzofuranyl, benzothiofuranyl, or benzopyrrolyl ring
v) $hAr^1$ has the structure

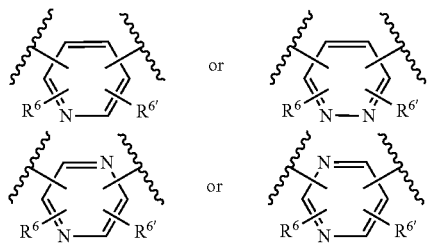

wherein $R^6$ and $R^{6'}$ are independently selected from hydrogen, a halogen, or a $C_1$-$C_4$ organic radical, and
vi) $hAr^2$ is a pyridyl, pyrazinyl, or pyrimidinyl ring.

The linked heteroaryl compounds of Formulas (I), (IA), (IB), (IC), and (ID), and species compounds encompassed therein can bind to and/or activate the T1R1/T1R3 "savory" ("umami") taste receptor proteins in-vitro, at very unexpectedly low concentrations on the order of micromolar or lower. The linked heteroaryl compounds are also believed to interact in the same or a similar manner with savory flavor receptors of animals or humans in vivo, as has been confirmed by actual human taste tests of selected compounds of Formula (I) that are reported below.

Accordingly, many of the subgenuses and species of the linked heteroaryl compounds of Formula (I) further described herein below can, at unexpectedly low concentrations be used as savory flavoring agents, or savory enhancers that substitute for and/or synergistically enhance the savory flavor of MSG.

Additional optional limitations on the chemical and physical characteristics of the heterocyclic compounds of Formula (I) and their substituent radicals or groups will be described below. Some of the heterocyclic compounds with structures encompassed within Formula (I) have been synthesized by methods known in the prior art, for various purposes, but to the knowledge of the inventors it has not been previously recognized that such linked heteroaryl compounds can be utilized as savory flavoring agents, or savory taste enhancers. Moreover many of the heterocyclic compounds of Formula (I) disclosed herein are novel compounds that have not been previously synthesized at all, and possess the unexpected property of being savory taste flavoring agents or taste enhancers.

The invention also relates to flavor modified comestible products, such as food and drinks, produced by contacting the compounds of the invention with comestible products or precursors thereof.

In many embodiments, one or more of the linked heteroaryl compounds of Formula (I) further identified, described, and/or claimed herein, or a comestibly acceptable salt thereof, can be used in mixtures or in combination with other known savory compounds such as MSG, as savory flavor enhancers in comestible food, and beverage compositions for human or animal consumption, or their precursors.

In many embodiments, the linked heteroaryl compounds of Formula (I) and its various subgenuses are T1R1/T1R3 receptor agonists and accordingly are believed to be capable of inducing or enhancing savory taste perception in humans. Many of the heterocyclic compounds of Formula (I) and/or its various subgenuses of heterocyclic compounds, when used together with MSG or alone, increase or modulate a response in vitro, and savory taste perception in humans at surprisingly low concentrations.

In some embodiments, the invention relates to novel compounds, flavoring agents, flavor enhancers, flavor modifying compounds, and/or compositions containing the compounds of Formula (I), and its various subgenuses and species compounds.

In some embodiments, the invention relates to comestible or medicinal compositions suitable for human or animal consumption, or precursors thereof, containing at least one compound of Formula (I), or a comestibly acceptable salt thereof.

The foregoing discussion merely summarizes certain aspects of the inventions and is not intended, nor should it be construed, as limiting the invention in any way.

DETAILED DESCRIPTION OF THE INVENTION

The present invention can be understood more readily by reference to the following detailed description of various embodiments of the invention and the Examples included therein and to the chemical drawings and Tables and their previous and following description. Before the present compounds, compositions, and/or methods are disclosed and described, it is to be understood that unless otherwise specifically indicated by the claims, the invention is not limited to specific foods or food preparation methods, specific comestible carriers or formulations, or to particular modes of formulating the compounds of the invention into comestible products or compositions intended for oral administration, because as one of ordinary skill in relevant arts is well aware, such things can of course, vary. It is also to be understood that the terminology used herein is for the purpose of describing particular embodiments only and is not intended to be limiting.

DEFINITIONS

A "comestibly acceptable carrier or excipient" is a solid or liquid medium and/or composition that is used to prepare a desired dispersed dosage form of the inventive compound, in order to administer the inventive compound in a dispersed/diluted form, so that the biological effectiveness of the inventive compound is maximized. Comestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste and/or smell in a subject, which include sweet, sour, salty, bitter, umami, and others. The subject may be a human or an animal.

A "flavoring agent" herein refers to a compound or a biologically acceptable salt thereof that induces a flavor or taste in an animal or a human.

A "flavor modifier" herein refers to a compound or biologically acceptable salt thereof that modulates, including enhancing or potentiating, and inducing, the tastes and/or smell of a natural or synthetic flavoring agent in an animal or a human.

A "flavor enhancer" herein refers to a compound or biologically acceptable salt thereof that enhances and/or multiplies the tastes or smell of a natural or synthetic flavoring agent, or a comestible composition comprising the flavor enhancer.

"Savory flavor" herein refers to the savory "umami" taste typically induced by MSG (mono sodium glutamate) in an animal or a human.

"Savory flavoring agent," "savory compound" or "savory receptor activating compound" herein refers to a compound or biologically acceptable salt thereof that elicits a detectable savory flavor in a subject, e.g., MSG (mono sodium glutamate) or a compound that activates a T1R1/T1R3 receptor in vitro. The subject may be a human or an animal.

A "savory flavor modifier" herein refers to a compound or biologically acceptable salt thereof that modulates, including enhancing or potentiating, inducing, and blocking, the savory taste of a natural or synthetic savory flavoring agents, e.g., monosodium glutamate (MSG) in an animal or a human.

A "savory flavor enhancer" herein refers to a compound or biologically acceptable salt thereof that enhances or potentiates the savory taste of a natural or synthetic savory flavoring agents, e.g., monosodium glutamate (MSG) in an animal or a human.

An "umami receptor activating compound" herein refers to a compound that activates an umami receptor, such as a T1R1/T1R3 receptor.

An "umami receptor modulating compound" herein refers to a compound that modulates (activates, enhances or blocks) an umami receptor.

An "umami receptor enhancing compound" herein refers to a compound that enhances or potentiates the effect of a natural or synthetic umami receptor activating compound, e.g., monosodium glutamate (MSG).

A "savory flavor modulating amount" herein refers to an amount of a compound of Formula (I) that is sufficient to alter (either increase or decrease) savory taste in a comestible or medicinal product or composition, or a precursor thereof, sufficiently to be perceived by a human subject. In many embodiments of the invention, at least about 0.001 ppm of the heterocyclic compound would need to be present in order for most human subjects to perceive a modulation of the savory flavor of a comestible composition comprising the heterocyclic compound. A broad range of concentration that would typically be employed in order to economically provide a desirable degree of savory flavor modulation can be from about 0.001 ppm to 100 ppm, or a narrow range from about 0.1 ppm to about 10 ppm. Alternative ranges of savory flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "savory flavor enhancing amount" herein refers to an amount of a compound that is sufficient to enhance the taste of a natural or synthetic flavoring agents, e.g., monosodium glutamate (MSG) in a comestible or medicinal product or composition, as perceived by an animal or a human. A broad range of a savory flavor enhancing amount can be from about 0.001 ppm to 100 ppm, or a narrow range from about 0.1 ppm to about 10 ppm. Alternative ranges of savory flavor enhancing amounts can be from about 0.01 ppm to about 30 ppm, from about 0.05 ppm to about 15 ppm, from about 0.1 ppm to about 5 ppm, or from about 0.1 ppm to about 3 ppm.

An "umami receptor modulating amount" herein refers to an amount of a compound that is sufficient to modulate (activate, enhance or block) an umami taste receptor protein. In many embodiments of the invention, an umami receptor modulating amount is at least about 1 pM, or at least about 1 nM, or at least about 10 nM, or at least about 100 nM (i.e. about 0.1 µM). A "T1R1/T1R3 receptor modulating or activating amount" is an amount of compound that is sufficient to modulate or activate a T1R1/T1R3 receptor. These amounts are preferably the same as the umami receptor modulating amounts.

An "umami receptor" is a taste receptor that can be modulated by a savory compound. Preferably an umami receptor is a G protein coupled receptor, and more preferably the umami receptor is a T1R1/T1R3 receptor.

Compounds of the invention modulate an umami receptor and preferably are agonists of the T1R1/T1R3 receptor. An agonist of this receptor has the effect of activating a G protein signaling cascade. In many cases, this agonist effect of the compound on the receptor also produces a perceived savory flavor in a taste test. It is desirable, therefore, that such inventive compounds serve as a replacement or enhancer for MSG, which is not well tolerated by some in, for example, comestible products.

In addition, this agonist effect also is responsible for the synergistic savory taste effect, which occurs when a compound of the invention is combined with another savory flavoring agent such as MSG. The nucleotides, IMP or GMP, are conventionally added to MSG, to intensify the savory flavor of MSG, so that relatively less MSG is needed to provide the same savory flavor in comparison to MSG alone. Therefore, it is desirable that combining compounds of the invention with another savory flavoring agent such as MSG advantageously eliminates the need to add expensive nucleotides, such as IMP, as a flavor enhancer, while concomitantly reducing or eliminating the amount of a savory compound such as MSG needed to provide the same savory flavor in comparison to the savory compound or MSG alone.

A "synergistic effect" relates to the enhanced savory flavor of a combination of savory compounds or receptor activating compounds, in comparison to the sum of the taste effects or flavor associated effects associated with each individual compound. In the case of savory enhancer compounds, a synergistic effect on the effectiveness of MSG may be indicated for a compound of Formula (I) having an EC50 ratio (defined herein below) of 2.0 or more, or preferably 5.0 or more, or 10.0 or more, or 15.0 or more.

When the compounds described here include one or more chiral centers, the stereochemistry of such chiral centers can independently be in the R or S configuration, or a mixture of the two. The chiral centers can be further designated as R or S or R,S or d,D, l,L or d,l, D,L. Correspondingly, the compounds of the invention, if they can be present in optically active form, can be present in the form of a racemic mixture of enantiomers, or in the form of either of the separate enantiomers in substantially isolated and purified form, or as a mixture comprising any relative proportions of the enantiomers. Where so indicated in the claims herein, if a single enantiomer of the potentially optically active heterocyclic compounds disclosed is desired, for either health or efficacy reasons, preferably it is present in an enantiomeric excess of at least about 80%, or at least about 90%, or at least about 95%, or at least about 98%, or at least about 99%, or at least about 99.5%.

As used herein, "hydrocarbon residue" refers to a chemical sub-group or radical within a larger chemical compound which contains only carbon and hydrogen atoms. The hydrocarbon residue may be aliphatic or aromatic, straight-chain, cyclic, branched, saturated or unsaturated. In many embodiments the hydrocarbon residues are of limited dimensional size and molecular weight, and may comprise 1 to 18 carbon atoms, 1 to 16 carbon atoms, 1 to 12 carbon atoms, 1 to 10 carbon atoms, 1 to 8 carbon atoms, 1 to 6 carbon atoms, or 1 to 4 carbon atoms.

The hydrocarbon residue, when described as "substituted," contains or is substituted with one or more independently selected heteroatoms such as O, S, N, P, or the halogens (fluorine, chlorine, bromine, and iodine), or one or more substituent groups containing heteroatoms (OH, $NH_2$, $NO_2$, $SO_3H$, and the like) over and above the carbon and hydrogen atoms of the substituent residue. Substituted hydrocarbon residues may also contain carbonyl groups, amino groups, hydroxyl groups and the like, or contain heteroatoms inserted into the "backbone" of the hydrocarbon residue.

As used herein, "inorganic" group or residue refers to a neutral, cationic, or anionic radical substituents on the organic molecules disclosed or claimed herein that have from one to 16 atoms that do not include carbon, but do contain other heteroatoms from the periodic table that preferably include one or more atoms independently selected from the group consisting of H, O, N, S, one or more halogens, or alkali metal or alkaline earth metal ions. Examples of inorganic radicals include, but are not limited to H, Na+, Ca++ and K+, halogens which include fluorine, chlorine, bromine, and iodine, OH, SH, $SO_3H$, $SO_3^-$, $PO_3H$, $PO_3^-$, NO, $NO_2$ or $NH_2$, and the like.

As used herein, the term "alkyl," "alkenyl" and "alkynyl" include straight- and branched-chain and cyclic monovalent substituents that respectively are saturated, unsaturated with at least one double bond, and unsaturated with at least one triple bond.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the alkyl groups are "$C_1$ to $C_6$ alkyl" such as methyl, ethyl, propyl, isopropyl, n-butyl, iso-butyl, sec-butyl, tert-butyl, amyl, tert-amyl, hexyl and the like. Many embodiments of the invention comprise "$C_1$ to $C_4$ alkyl" groups (alternatively termed "lower alkyl" groups) that include methyl, ethyl, propyl, isopropyl n-butyl, iso-butyl, sec-butyl, and t-butyl groups. Some of the preferred alkyl groups of the invention have three or more carbon atoms preferably 3 to 16 carbon atoms, 4 to 14 carbon atoms, or 6 to 12 carbon atoms.

The term "alkenyl" is structurally analogous to an alkyl group or residue that comprises at least one carbon-carbon double bond. In some embodiments, alkenyl groups are "$C_2$ to $C_7$ alkenyls" which are exemplified by vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains. In other embodiments, alkenyls are limited to two to four carbon atoms.

The term "alkynyl" is analogous to an alkyl group or radical that comprises at least one carbon-carbon triple bond. Preferred alkynyl groups are "$C_2$ to $C_7$ alkynyl" such as ethynyl, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl as well as di- and tri-ynes of straight and branched chains including ene-ynes.

The terms "substituted alkyl," "substituted alkenyl," "substituted alkynyl," and "substituted alkylene" denote that the alkyl, alkenyl, or alkynyl groups or radicals as described herein, wherein one or more hydrogen atoms has been conceptually substituted by one or more, and preferably one or two independently selected organic or inorganic substituent groups or radicals, that can include a halogen, hydroxy, amino, SH, a $C_1$ to $C_7$ alkoxy, or alkoxy-alkyl, oxo, $C_3$ to $C_7$ cycloalkyl, naphthyl, amino, (monosubstituted)amino, (disubstituted)amino, guanidino, heterocycle, substituted heterocycle, imidazolyl, indolyl, pyrrolidinyl, $C_1$ to $C_7$ acyl, $C_1$ to $C_7$ acyloxy, nitro, carboxy, carbamoyl, carboxamide, N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted alkyl groups may be substituted once or more, and preferably once or twice, with the same or with different substituents. In many embodiments of the invention, a preferred group of substituent groups for a substantial alkyls include hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups. In many embodiments of the invention that comprise the above lists of substituent groups, an even more preferred group of substituent groups include hydroxy, SEt, $SCH_3$, methyl, ethyl, isopropyl, trifluoromethyl, methoxy, ethoxy, and trifluoromethoxy groups.

Examples of the above substituted alkyl groups include the 2-oxo-prop-1-yl, 3-oxo-but-1-yl, cyanomethyl, nitromethyl, chloromethyl, trifluoromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted double bond can be included.

Examples of substituted alkynyl groups include phenylacetylen-1-yl, 1-phenyl-2-propyn-1-yl and the like.

Haloalkyls are substituted alkyl groups or residues wherein one or more hydrogens of the corresponding alkyl group have been replaced with a halogen atom (fluorine, chlorine, bromine, and iodine). Preferred haloalkyls can have one to four carbon atoms. Examples of preferred haloalkyl groups include trifluoromethyl and pentafluoroethyl groups.

Haloalkoxy groups are alkoxy groups or residues wherein one or more hydrogens from the R group of the alkoxy group are a halogen atom (fluorine, chlorine, bromine, and iodine). Preferred haloalkoxy groups can have one to four carbon atoms. Examples of preferred haloalkoxy groups include trifluoromethyoxy and pentafluoroethoxy groups.

The term "oxo" denotes a carbon atom bonded to two additional carbon atoms substituted with an oxygen atom doubly bonded to the carbon atom, thereby forming a ketone radical or residue.

"Alkoxy" or "alkoxyl" refers to an —OR radical or group, wherein R is an alkyl radical. In some embodiments the alkoxy groups can be $C_1$ to $C_8$, and in other embodiments can be $C_1$ to $C_4$ alkoxy groups wherein R is a lower alkyl, such as a methoxy, ethoxy, n-propoxy, isopropoxy, n-butoxy, t-butoxy and like alkoxy groups. The term "substituted alkoxy" means that the R group is a substituted alkyl group or residue. Examples of substituted alkoxy groups include trifluoromethoxy, hydroxymethyl, hydroxyethyl, hydroxypropyl, and alkoxyalkyl groups such as methoxymethyl, methoxyethyl, polyoxoethylene, polyoxopropylene, and similar groups.

"Alkoxyalkyl" refers to an —R—O—R' group or radical, wherein R and R' are alkyl groups. In some embodiments the alkoxyalkyl groups can be $C_1$ to $C_8$, and in other embodiments can be $C_1$ to $C_4$. In many embodiments, both R and R' are a lower alkyl, such as a methoxy, ethoxy, n-propoxy, isopropoxy, n-butoxy, t-butoxy and like alkoxy groups. Examples of alkoxyalkyl groups include, methoxymethyl, ethoxyethyl, methoxypropyl, and methoxybutyl and similar groups.

"Acyloxy" refers to an $RCO_2$— ester group where R is an alkyl, cycloalkyl, aryl, heteroaryl, substituted alkyl, substituted cycloalkyl, substituted aryl, or substituted hetaryl group or radical wherein the R radical comprises one to seven or one to four carbon atoms. In many embodiments, R is an alkyl radical, and such acyloxy radicals are exemplified by formyloxy, acetoxy, propionyloxy, butyryloxy, pivaloyloxy, pentanoyloxy, hexanoyloxy, heptanoyloxy and the like. In other embodiments the R groups are $C_1$-$C_4$ alkyls.

As used herein, "acyl" encompasses the definitions of alkyl, alkenyl, alkynyl and the related hetero-forms which are coupled to an additional organic residue through a carbonyl group to form a ketone radical or group. Preferred acyl groups are "$C_1$ to $C_7$ acyl" such as formyl, acetyl, propionyl, butyryl, pentanoyl, pivaloyl, hexanoyl, heptanoyl, benzoyl and the like. More preferred acyl groups are acetyl and benzoyl.

The term "substituted acyl" denotes an acyl group wherein the R group substituted by one or more, and preferably one or two, halogen, hydroxy, oxo, alkyl, cycloalkyl, naphthyl, amino, (monosubstituted)amino, (disubstituted)amino, guanidino, heterocyclic ring, substituted heterocyclic ring, imidazolyl, indolyl, pyrrolidinyl, $C_1$ to $C_7$ alkoxy, alkoxyalkyl, $C_1$ to $C_7$ acyl, $C_1$ to $C_7$ acyloxy, nitro, $C_1$ to $C_6$ alkyl ester, carboxy, alkoxycarbonyl, carbamoyl, carboxamide, N—($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_7$ substituted acyl groups include 4-phenylbutyroyl, 3-phenylbutyroyl, 3 phenylpropanoyl, 2-cyclohexanylacetyl, cyclohexanecarbonyl, 2-furanoyl and 3 dimethylaminobenzoyl.

Cycloalkyl residues or groups are structurally related to cyclic monocyclic or bicyclic hydrocarbon compounds wherein one or more hydrogen atoms has been replaced with an organic or inorganic substituent group. The cycloalkyls of the current inventions comprise at least 3 up to 12, or more preferably 3 to 8 ring carbon atoms, or more preferably 4 to 6 ring carbon atoms. Examples of such cyclalkyl residues include cyclopropyl, cyclobutyl, cyclopentyl, cyclohexyl, cycloheptyl, cyclooctyl rings, and saturated bicyclic or fused polycyclic cycloalkanes such as decalin groups, polycyclic norbornyl or adamantyl groups, and the like.

Preferred cycloalkyl groups include "$C_3$ to $C_7$ cycloalkyl" such as cyclopropyl, cyclobutyl, cyclopentyl, cyclohexyl or cycloheptyl rings. Similarly, the term "$C_5$ to $C_7$ cycloalkyl" includes cyclopentyl, cyclohexyl or cycloheptyl rings.

"Substituted cycloalkyl" denote a cycloalkyl rings as defined above, substituted by 1 to four, or preferably one or two substituents independently selected from a halogen, hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_4$ alkyl, $C_1$ to $C_4$ alkoxy, $C_1$ to $C_6$ substituted alkyl, $C_1$ to $C_4$ alkoxy-alkyl, oxo (monosubstituted)amino, (disubstituted) amino, trifluoromethyl, carboxy, phenyl, substituted phenyl, phenylthio, phenylsulfoxide, phenylsulfonyl, amino. In many embodiments of substituted cycloalkyl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "cycloalkenyl" indicates preferably a 1,2, or 3-cyclopentenyl ring, a 1,2,3 or 4-cyclohexenyl ring or a 1,2,3,4 or 5-cycloheptenyl ring, while the term "substituted cycloalkenyl" denotes the above cycloalkenyl rings substituted with a substituent, preferably by a $C_1$ to $C_6$ alkyl, halogen, hydroxy, $C_1$ to $C_7$ alkoxy, alkoxy-alkyl, trifluoromethyl, carboxy, alkoxycarbonyl oxo, (monosubstituted)amino, (disubstituted)amino, phenyl, substituted phenyl, amino, or protected amino.

The term "cycloalkenylene" is a cycloalkenyl ring, as defined above, where the cycloalkenyl radical is bonded at two positions connecting together two separate additional groups. Similarly, the term "substituted cycloalkenylene" means a cycloalkenylene further substituted preferably by halogen, hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or substituted amino group.

The term "heterocycle" or "heterocyclic ring" denotes optionally substituted 3 to 8-membered rings having one or more carbon atoms connected in a ring that also comprise 1 to 5 ring heteroatoms, such as oxygen, sulfur and/or nitrogen inserted into the ring. These heterocyclic rings can be saturated, unsaturated or partially unsaturated, but are preferably saturated. Preferred unsaturated heterocyclic rings include furanyl, thiofuranyl, pyrrolyl, pyridyl, pyrimidyl, pyrazinyl, benzoxazole, benzthiazole, quinolinlyl, and like heteroaromatic rings. Preferred saturated heterocyclic rings include piperidyl, aziridinyl, piperidinyl, piperazinyl, tetrahydrofurano, pyrrolyl, and tetrahydrothiophen-yl.rings.

The term "substituted heterocycle" or "substituted heterocyclic ring" means the above-described heterocyclic ring is substituted with, for example, one or more, and preferably one or two, substituents which are the same or different which substituents preferably can be halogen, hydroxy, thio, alkylthio, cyano, nitro, $C_1$ to $C_4$ alkyl, $C_1$ to $C_4$ alkoxy, $C_1$ to $C_4$ substituted alkoxy, alkoxy-alkyl, $C_1$ to $C_4$ acyl, $C_1$ to $C_4$ acyloxy, carboxy, alkoxycarbonyl, carboxymethyl, hydroxymethyl, alkoxy-alkyl amino, monosubstituted)amino, (disubstituted)amino carboxamide, N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino groups, or substituted with a fused ring, such as benzo-ring. In many embodiments of substituted heterocyclic groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

An "aryl" group refers to a monocyclic, linked bicyclic or fused bicyclic radical or group comprising at least one six membered aromatic "benzene" ring. Aryl groups preferably comprise between 6 and 12 ring carbon atoms, and are exemplified by phenyl, biphenyl, naphthyl, indanyl, and tetrahydronapthyl groups. Aryl groups can be optionally substituted with various organic and/or inorganic substituent groups, wherein the substituted aryl group in combination with all its substituents comprise between 6 and 18, or preferably 6 and 16 total carbon atoms. Preferred optional substituent groups include 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The term "heteroaryl" means a heterocyclic aryl derivative which preferably contains a five-membered or six-membered conjugated and aromatic ring system having from 1 to 4 heteroatoms independently selected from oxygen, sulfur and/or nitrogen, inserted into the unsaturated and conjugated heterocyclic ring. Heteroaryl groups include monocyclic heteroaromatic, linked bicyclic heteroaromatic or fused bicyclic heteroaromatic moieties. Examples of heteroaryls include pyridinyl, pyrimidinyl, and pyrazinyl, pyridazinyl, pyrrolyl, furanyl, thiofuranyl, oxazoloyl, isoxazolyl, phthalimido, thiazolyl, quinolinyl, isoquinolinyl, indolyl, or a furan or thiofuran directly bonded to a phenyl, pyridyl, or pyrrolyl ring and like unsaturated and conjugated heteroaromatic rings. Any monocyclic, linked bicyclic, or fused bicyclic heteroaryl ring system which has the characteristics of aromaticity in terms of electron distribution throughout the ring system is included in this definition. Typically, the heteroaromatic ring systems contain 3-12 ring carbon atoms and 1 to 5 ring heteroatoms independently selected from oxygen, nitrogen, and sulfur atoms.

The term "substituted heteroaryl" means the above-described heteroaryl is substituted with, for example, one or more, and preferably one or two, substituents which are the same or different which substituents preferably can be halogen, hydroxy, protected hydroxy, thio, alkylthio, cyano, nitro, $C_1$ to $C_6$ alkyl, $C_1$ to $C_7$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted) amino, (disubstituted)amino, carboxamide, N—(C1 to C6 alkyl)carboxamide, N,N-di(C1 to C6 alkyl)carboxamide, trifluoromethyl, N—((C1 to C6 alkyl)sulfonyl)amino or N-(phenylsulfonyl)amino groups. In many embodiments of substituted heteroaryl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety. Preferably, arylalkyl or heteroarylalkyl is an alkyl group substituted at any position by an aryl group, substituted aryl, heteroaryl or substituted heteroaryl. Preferred groups also include benzyl, 2-phenylethyl, 3-phenylpropyl, 4-phenyl-n-butyl, 3-phenyl-n-amyl, 3-phenyl-2-butyl, 2-pyridinylmethyl, 2-(2-pyridinyl)ethyl, and the like.

The term "substituted arylalkyl" denotes an arylalkyl group substituted on the alkyl portion with one or more, and preferably one or two, groups preferably chosen from halogen, hydroxy, oxo, amino, (monosubstituted)amino, (disubstituted)amino, guanidino, heterocyclic ring, substituted heterocyclic ring, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, nitro, carboxy, alkoxycarbonyl, carbamoyl, carboxamide, N—($C_1$ to $C_6$ alkyl)carboxamide, N,N—($C_1$ to $C_6$ dialkyl)carboxamide, cyano, N—($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents preferably chosen from halogen, hydroxy, protected hydroxy, thio, alkylthio, cyano, nitro, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted)amino, (disubstituted)amino, carboxamide, N—($C_1$ to $C_6$ alkyl) carboxamide, N,N-di($C_1$ to $C_6$ alkyl)carboxamide, trifluoromethyl, N—((C1 to C6 alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "substituted arylalkyl" include groups such as 2-phenyl-1-chloroethyl, 2-(4-methoxyphenyl)ethyl, 4-(2,6-dihydroxy phenyl)-n-hexyl, 2-(5-cyano-3-methoxyphenyl)-n-pentyl, 3-(2,6-dimethylphenyl)propyl, 4-chloro-3-aminobenzyl, 6-(4-methoxyphenyl)-3-carboxy-n-hexyl, 5-(4-aminomethylphenyl)-3-(aminomethyl)-n-pentyl, 5-phenyl-3-oxo-n-pent-1-yl and the like.

The term "arylalkylene" specifies an arylalkyl, as defined above, where the arylalkyl radical is bonded at two positions connecting together two separate additional groups. The definition includes groups of the formula: -phenyl-alkyl- and alkyl-phenyl-alkyl-. Substitutions on the phenyl ring can be 1,2, 1,3 or 1,4. The term "substituted arylalkylene" is an arylalkylene as defined above that is further substituted preferably by halogen, hydroxy, protected hydroxy, $C_1$ to $C_4$ alkylthio, $C_1$ to $C_4$ alkylsulfoxide, $C_1$ to $C_4$ alkylsulfonyl, $C_1$ to $C_4$ substituted alkylthio, $C_1$ to $C_4$ substituted alkylsulfoxide, $C_1$ to $C_4$ substituted alkylsulfonyl, $C_1$ to $C_6$ alkyl, $C_1$ to $C_7$ alkoxy, $C_1$ to $C_6$ substituted alkyl, $C_1$ to $C_7$ alkoxy-alkyl, oxo, (monosubstituted)amino, (disubstituted)amino, trifluoromethyl, carboxy, alkoxycarbonyl, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties preferably chosen from the groups consisting of halogen, hydroxy, protected hydroxy, thio, alkylthio, cyano, nitro, $C_1$ to $C_6$ alkyl, $C_1$ to $C_6$ substituted alkyl, $C_1$ to $C_7$ alkoxy, $C_1$ to $C_7$ substituted alkoxy, alkoxy-alkyl, $C_1$ to $C_7$ acyl, $C_1$ to $C_7$ substituted acyl, $C_1$ to $C_7$ acyloxy, carboxy, alkoxycarbonyl, carboxymethyl, hydroxymethyl, amino, (monosubstituted)amino, (disubstituted)amino, carboxamide, N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, wherein the phenyl is substituted or unsubstituted, such that, for example, a biphenyl results. In many embodiments of substituted phenyl groups, the substituted cycloalkyl group will have 1, 2, 3, or 4 substituent groups independently selected from hydroxy, fluoro, chloro, $NH_2$, $NHCH_3$, $N(CH_3)_2$, $CO_2CH_3$, SEt, $SCH_3$, methyl, ethyl, isopropyl, vinyl, trifluoromethyl, methoxy, ethoxy, isopropoxy, and trifluoromethoxy groups.

The terms "halo" and "halogen" refer to fluoro, chloro, bromo or iodo atoms or ions. Preferred halogens are chloro and fluoro. Although many of the compounds of the invention having halogen atoms as substituents are highly effective in binding to the relevant Umami taste receptors, such halogenated organic compounds can in some cases have undesirable toxicological properties when administered to an animal in vivo. Therefore, in the various embodiments of the compounds of Formula (I), if a halogen atom (including a fluoro, chloro, bromo, or iodo atom) is listed as a possible substitutent, an alternative and preferred group of substitutents expressly contemplated hereby would NOT include the halogen groups.

The term "(monosubstituted)amino" refers to an amino (NHR) group wherein the R group is chosen from the group consisting of phenyl, $C_6$-$C_{10}$ substituted phenyl, $C_1$ to $C_6$ alkyl, $C_1$ to $C_6$ substituted alkyl, $C_1$ to $C_7$ acyl, $C_1$ to $C_7$ substituted acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino."

The term "(disubstituted)amino" refers to an amino group ($NR_2$) with two substituents independently chosen from the group consisting of phenyl, $C_6$-$C_{10}$ substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "alkylthio" refers to —SR groups wherein R is an optionally substituted $C_1$-$C_7$ or $C_1$-$C_4$ organic group, preferably an alkyl, cycloalkyl, aryl, or heterocyclic group, such as methylthio, ethylthio, n-propylthio, isopropylthio, n-butylthio, t-butylthio and like groups.

The term "alkylsulfoxide" indicates —$SO_2R$ groups wherein R is an optionally substituted $C_1$-$C_7$ or $C_1$-$C_4$ organic group, preferably an alkyl, cycloalkyl, aryl, or heterocyclic group, such as methylthio, ethylthio, n-propylthio, isopropylthio, n-butylthio, t-butylthio and like groups, such as methylsulfoxide, ethylsulfoxide, n-propylsulfoxide, isopropylsulfoxide, n-butylsulfoxide, sec-butylsulfoxide and the like.

The term "alkylsulfonyl" indicates —S(O)R groups wherein R is an optionally substituted $C_1$-$C_7$ or $C_1$-$C_4$ organic group, which include for example groups such as methylsulfonyl, ethylsulfonyl, n-propylsulfonyl, isopropylsulfonyl, n-butylsulfonyl, t-butylsulfonyl and the like.

The terms "phenylthio," "phenylsulfoxide," and "phenylsulfonyl" specify a sulfoxide (—S(O)—R), or sulfone (—SO$_2$R) wherein the R group is a phenyl group. The terms "substituted phenylthio," "substituted phenylsulfoxide," and "substituted phenylsulfonyl" means that the phenyl of these groups can be substituted as described above in relation to "substituted phenyl."

The term "alkoxycarbonyl" means an "alkoxy" group attached to a carbonyl group, (i.e. a carboxylic acid ester, —C(O)—OR, wherein R is preferably an alkyl group, preferably a C$_1$-C$_4$ alkyl group. The term "substituted alkoxycarbonyl" denotes a substituted alkoxy bonded to the carbonyl group, which alkoxy may be substituted as described above in relation to substituted alkyl.

The term "phenylene" means a phenyl group where the phenyl radical is bonded at two positions connecting together two separate additional groups. Examples of "phenylene" includes 1,2-phenylene, 1,3-phenylene, and 1,4-phenylene.

The term "substituted alkylene" means an alkyl group where the alkyl radical is bonded at two positions connecting together two separate additional groups and further bearing an additional substituent. Examples of "substituted alkylene" includes aminomethylene, 1-(amino)-1,2-ethyl, 2-(amino)-1, 2-ethyl, 1-(acetamido)-1,2-ethyl, 2-(acetamido)-1,2-ethyl, 2-hydroxy-1,1-ethyl, 1-(amino)-1,3-propyl.

One or more of the compounds of the invention, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as nitrogen containing heterocycles or amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to positively charged counter-ions for the carboxylate anion of a carboxylate salt. Inorganic positively charged counter-ions include but are not limited to the alkali and alkaline earth metals, (such as lithium, sodium, potassium, calcium, magnesium, etc.) and other divalent and trivalent metallic cations such as barium, aluminum and the like, and ammonium (NH$_4$)$^+$ cations. Organic cations include ammonium cations derived from acid treatment or alkylation of primary-, secondary, or tertiary amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge, et al., *J. Pharm. Sci.* (1977) 66:1-19, which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when R$^2$ or R$^3$ is substituted with a (quaternary ammonium)methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

A residue of a chemical species, as used in the specification and concluding claims, refers to a structural fragment, or a moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —OCH$_2$CH$_2$O— repeat units in the polyester, regardless of whether ethylene glycol is used to prepare the polyester.

The term "organic residue" or "organic radical" defines a carbon containing residue or radical, comprising at least one carbon atom. Organic residues can contain one or more heteroatoms, or be bonded to another molecule through a heteroatom, including oxygen, nitrogen, sulfur, phosphorus, or the like. Examples of organic residues include but are not limited alkyl or substituted alkyls, alkoxyls or substituted alkoxyls, hydroxyalkyls and alkoxyalkyls, cycloalkyl or substituted cycloalkyls, cycloalkenyl or substituted cycloalkyenyls, heterocycles and substituted heterocycles, aryls and substituteed aryls, heteroaryls and substituted heteroaryls, mono or di-substituted amino, amide groups, CN, CO$_2$H, CHO, COR$^6$, CO$_2$R$^6$, SR$^6$ wherein R$^6$ is an alkyl, and the like. Examples of species of organic groups or residues include but are not limited to NHCH$_3$, N(CH$_3$)$_2$, CO$_2$CH$_3$, SEt, SCH$_3$, methyl, ethyl, isopropyl, vinyl, trifluoromethyl, methoxy, ethoxy, isopropoxy, trifluoromethoxy, phenyl, phenoxyl, and pyridyl groups or residues, and the like. Organic residues can comprise 1 to 18 carbon atoms, 1 to 15, carbon atoms, 1 to 12 carbon atoms, 1 to 8 carbon atoms, or 1 to 4 carbon atoms.

By the term "effective amount" of a compound as provided herein is meant a sufficient amount of the compound to provide the desired regulation of a desired function, such as gene expression, protein function, or the induction of a particular type of taste perception. As will be pointed out below, the exact amount required will vary from subject to subject, depending on the species, age, general condition of the subject, specific identity and formulation of the comestible composition, etc. Thus, it is not possible to specify an exact "effective amount." However, an appropriate effective amount can be determined by one of ordinary skill in the art using only routine experimentation.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyls where there is substitution.

The Linked Heteroaryl Compounds of the Invention

While not wishing to be bound by theory, the linked heteroaryl compounds described herein are believed to be agonists and/or allosteric modifiers of umami taste receptor proteins. Accordingly, it is reasonable to believe that the linked heteroaryl compounds have a core of linked structural elements which when considered as a whole, and despite some possible variability in each of the individual structural elements or their peripheral substitutents, have a size, shape, and/or polarity that allows for significant and specific attractive interactions with the umami taste receptor proteins, so that the linked heteroaryl compounds can modify, improve, and/or enhance the umami taste of comestible products intended for animal and/or human consumption. Accordingly, the linked heteroaryl compounds, while they may differ in some respects, nevertheless share certain structural features that, to somewhat varying degrees, promote desirable agonistic or allosteric binding interactions with the umami taste receptor proteins.

Accordingly, the compounds of the invention all comprise at least two aromatic "aryl" or "heteroaryl" groups $hAr^1$ and $hAr^2$, and a third aryl or heteroaryl ring group Ar, all three of which aromatic ring groups can be optionally substituted by a variety of peripheral substitutents. Moreover, the $hAr^1$, $hAr^2$ and Ar ring groups are linked together by bridging or linking groups X, Y, and/or $CR_3R_4$ as further defined below, which may be present in defined but variable numbers, or in some cases optionally absent. More specifically, the compounds of the invention (the "linked heteroaryl compounds") are a genus of compounds which share a core of structural features shown in Formula (I) below:

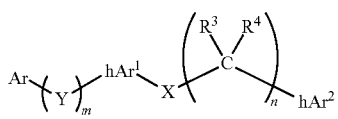

(I)

wherein the various groups can be defined, and/or selected in alternate and various ways, as shown in the Summary of the Invention section above, or below.

In some embodiments of the linked heteroaryl compounds of Formula (I):

i) Ar is a monocyclic or bicyclic aryl or heteroaryl radical comprising one or two aromatic rings independently selected from benzene rings and five or six membered heteroaryl rings, each aromatic ring optionally having one or two $R^{20}$ substituent radicals bound thereto, wherein each $R^{20}$ radical is independently selected from hydroxyl, $NH_2$, SH, halogen, or a $C_1$-$C_4$ organic radical;

ii) Y is O, S, S(O), $SO_2$, $CR^1R^2$, or $NR^5$;

iii) m is the integer zero or one;

iv) $hAr^1$ is a five or six-membered heteroaryl ring radical comprising at least two ring carbon atoms and one to three ring heteroatoms independently selected from O, N, or S, wherein any remaining members of the heteroaromatic ring are independently selected from from $CR^6$, N, $NR^7$;

v) X is O, S, S(O), $SO_2$, $CR^8R^9$, or $NR^{10}$;

vi) n is the integer zero, one, two, or three;

vii) $R^1$, $R^2$, $R^3$, $R^4$, $R^8$ and $R^9$ are independently selected from hydrogen, oxygen, hydroxyl, $NH_2$, SH, halogen, or a $C_1$-$C_4$ organic radical, and $R^5$, $R^7$ and $R^{10}$ are independently selected from hydrogen, hydroxyl, or a $C_1$-$C_4$ organic radical, and $R^6$ is hydrogen, halogen, or a $C_1$-$C_4$ organic radical;

viii) $hAr^2$ is a five or six-membered heteroaryl ring having at least two ring carbon atoms and at least one ring nitrogen atom, and wherein the remaining members of the heteroaromatic ring are independently selected from $CR^{30}$, N, $NR^{31}$, O, and S, wherein each $R^{30}$ is independently selected from hydrogen, a halogen, or a $C_1$-$C_4$ organic radical and each $R^{31}$ is independently selected from hydrogen, or a $C_1$-$C_4$ organic radical;

or a comestibly acceptable salt thereof.

In closely related embodiments of the linked heteroaryl compounds of Formula (I) wherein $hAr^2$ is an aryl ring:

i) Ar is a monocyclic or bicyclic aryl or heteroaryl radical comprising one or two aromatic rings independently selected from benzene rings and five or six membered heteroaryl rings, each aromatic ring optionally having one or two $R^{20}$ substituent radicals bound thereto, wherein each $R^{20}$ radical is independently selected from hydroxyl, $NH_2$, SH, halogen, or a $C_1$-$C_4$ organic radical;

ii) Y is O, S, S(O), $SO_2$, $CR^1R^2$, or $NR^5$;

iii) m is the integer zero or one;

iv) $hAr^1$ is a five or six-membered heteroaryl ring radical comprising at least two ring carbon atoms and one to three ring heteroatoms independently selected from O, N, or S, wherein any remaining members of the heteroaromatic ring are independently selected from from $CR^6$, N, $NR^7$;

v) X is O, S, S(O), $SO_2$, $CR^8R^9$, or $NR^{10}$ vi) n is the integer zero, one, two, or three;

vii) $R^1$, $R^2$, $R^3$, $R^4$, $R^8$ and $R^9$ are independently selected from hydrogen, oxygen, hydroxyl, $NH_2$, SH, halogen, or a $C_1$-$C_4$ organic radical, and $R^5$, $R^7$ and $R^{10}$ are independently selected from hydrogen, hydroxyl, or a $C_1$-$C_4$ organic radical, and $R^6$ is hydrogen, halogen, or a $C_1$-$C_4$ organic radical;

viii) $hAr^2$ is a phenyl ring optionally substituted with 0, 1, 2, or 3 $R^{30}$ radicals independently selected from hydrogen, a halogen, or a $C_1$-$C_4$ organic radical;

or a comestibly acceptable salt thereof.

Other related embodiments of the invention provide for taste modified comestible compositions comprising at least a savory flavor modulating amount of at least one compound of Formula I that do not comprise the "Y" groups of the compounds of Formula I and therefore have the formula:

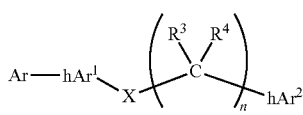

wherein i) Ar is a monocyclic or bicyclic aryl or heteroaryl radical comprising one or two aromatic rings independently selected from benzene rings and five or six membered heteroaryl rings, each aromatic ring optionally having one, two, or three $R^{20}$ substituent radicals bound thereto, wherein each $R^{20}$ radical is independently selected from hydroxyl, $NH_2$, $NO_2$, SH, $SO_3H$, $P(O)(OH)_2$, halogen, or a $C_1$-$C_4$ organic radical;

ii) $hAr^1$ is a five or six-membered heteroaryl ring radical having from 1 to 4 heteroatoms independently selected from oxygen, sulfur and/or nitrogen, wherein any remaining members of the heteroaromatic ring are independently selected from $CR^6$, N, $NR^7$;

iii) X is O, S, S(O), $SO_2$, $CR^8R^9$, or $NR^{10}$;

iv) n the integer zero, one, two, or three;

v) $R^3$, $R^4$, $R^8$ and $R^9$ are independently selected from hydrogen, oxygen, hydroxyl, $NH_2$, SH, halogen, or a $C_1$-$C_4$ organic radical, and $R^7$ and $R^{10}$ are independently selected from hydrogen, hydroxyl, or a $C_1$-$C_4$ organic radical, and $R^6$ is hydrogen, halogen, or a $C_1$-$C_4$ organic radical;

vi) $hAr^2$ is a five or six-membered heteroaryl ring having at least one ring carbon atom and at least one ring nitrogen atom, and wherein the remaining members of the heteroaryl ring are independently selected from $CR^{30}$, N, $NR^{31}$, O, and S, wherein each $R^{30}$ is independently selected from hydrogen, hydroxyl, $NH_2$, $NO_2$, SH, $SO_3H$, $P(O)(OH)_2$, a halogen, or a $C_1$-$C_4$ organic radical, and each $R^{31}$ is independently selected from hydrogen, or a $C_1$-$C_4$ organic radical;

or a comestibly acceptable salt thereof.

In other related embodiments, the compounds of Formula I include compounds having Formula (IA) shown below that comprise hAr1 radicals that are five-membered heteroaryl radicals:

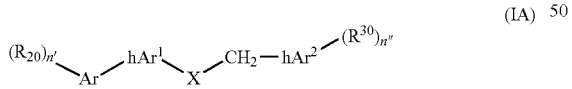

wherein i) n' is zero, one, two, or three, and each $R^{20}$ is independently selected from the group consisting of hydroxy, SH, $NH_2$, a halogen, or a $C_1$-$C_4$ organic radical, ii) n" is zero, one, two, or three, and each $R^{30}$ is independently selected from the group consisting of hydroxy, SH, $NH_2$, a halogen, or a $C_1$-$C_4$ organic radical, iii) X is NH, O, S, S(O), $SO_2$, or $CH_2$, iv) Ar is a phenyl, pyridyl, pyrazinyl, pyrimidinyl, furanyl, thiofuranyl, pyrrolyl, benzofuranyl, benzothiofuranyl, or benzopyrrolyl ring v) $hAr^1$ has the structure:

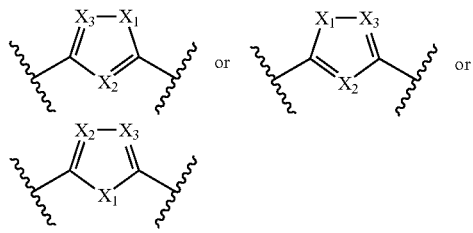

(1) $X_1$ is NH, O, or S,
(2) $X_2$ is N or $CR^6$ wherein $R^6$ is hydrogen, a halogen, or a $C_1$-$C_4$ organic radical,
(3) $X_3$ is N or $CR^6$ wherein $R^6$ is hydrogen, a halogen, or a $C_1$-$C_4$ organic radical, and vi) $hAr^2$ is a a pyridyl, pyrazinyl, or pyrimidinyl ring;
or a comestibly acceptable salt thereof.

The genera and subgenera of linked heteroaryl compounds defined above comprise many previously unknown subgenuses of compounds, and/or species of compounds, and also comprise some compounds that may have been previously reported in the prior art in connection with other uses. Nevertheless, to the knowledge and belief of the Applicants, the prior art has not recognized that the compounds shown above and their various genara and subgenera are useful for modifying, improving, and/or enhancing the umami flavor of comestible compositions at the unexpectedly low concentrations disclosed herein.

The Ar Radical and its Substitutents

The Ar radical of the compounds of Formula (I) and its various subgenuses can be an optionally substituted monocyclic or bicyclic aryl or heteroaryl radicals (as defined elsewhere herein) comprising one or two aromatic rings independently selected from benzene rings and five or six membered heteroaryl rings, with one, two, or three optional $R^{20}$ substitutents which may be attached at any of the positions of the aryl or heteroaryl ring radical other than the position which provides the link to the Y or $hAr^1$ radical.

In many embodiments of the compounds of Formula I and its subgenera, Ar is a monocyclic or bicyclic aryl radical that comprises one at least one benzene ring. When Ar is a monocyclic aryl, exemplary Ar radicals could include the following structures:

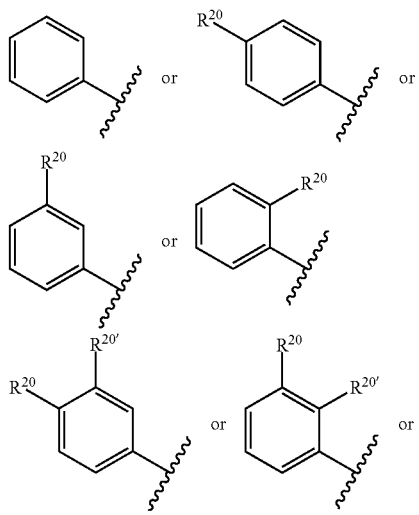

-continued

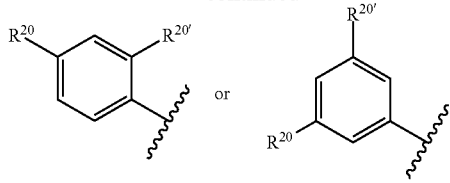

In some embodiments of the compounds of Formula I and its subgenera, Ar has the

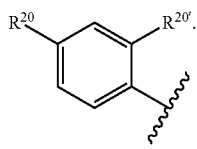

If Ar is a bicyclic aryl radical, exemplary Ar radicals could include the followings structures:

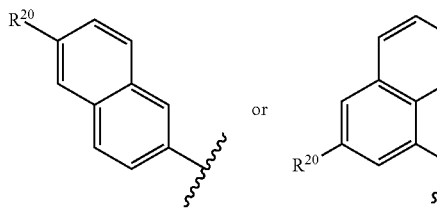

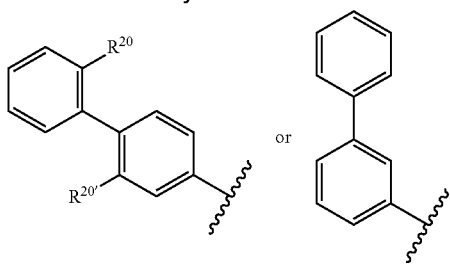

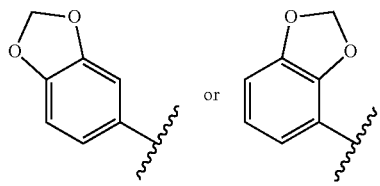

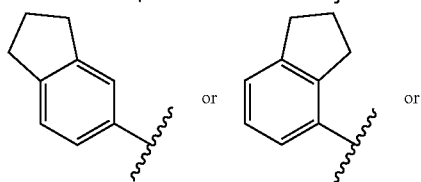

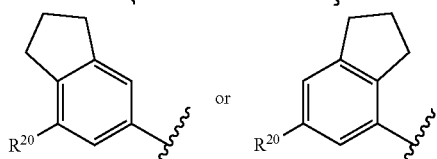

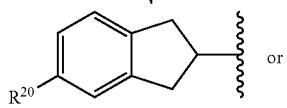

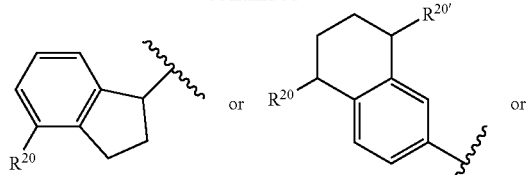

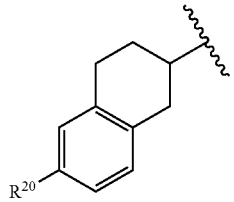

In other embodiments of the compounds of Formula (I) and its subgenera, Ar is an optionally substituted monocyclic or bicyclic heteroaryl radical comprising one or two aromatic rings independently selected from five or six membered heteroaryl rings. Monocyclic heteroaryl Ar rings with a six membered ring include optionally substituted pyridyl, pyrazinyl, or pyrimidinyl rings, which include but are not limited to the following exemplary structures:

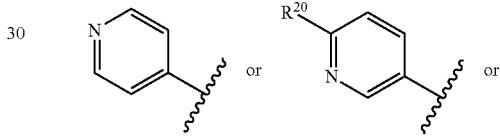

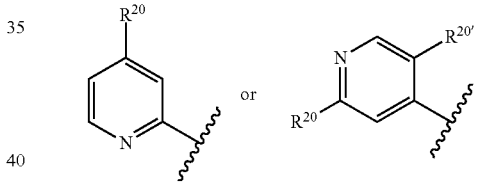

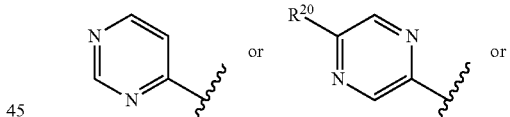

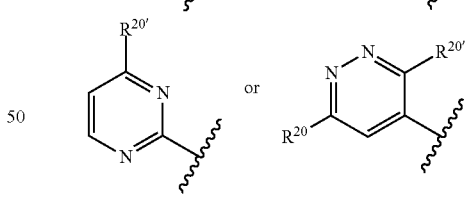

Monocyclic heteroaryl Ar rings with a five membered rings include optionally substituted furanyl, thiofuranyl, pyrrolyl, pyrazolyl, oxazolyl, or isoxazolyl ring, which include but are not limited to the following exemplary structures:

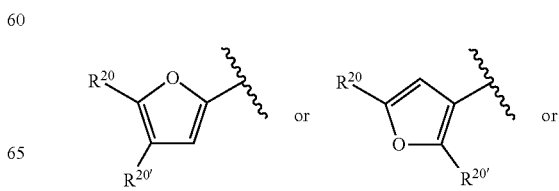

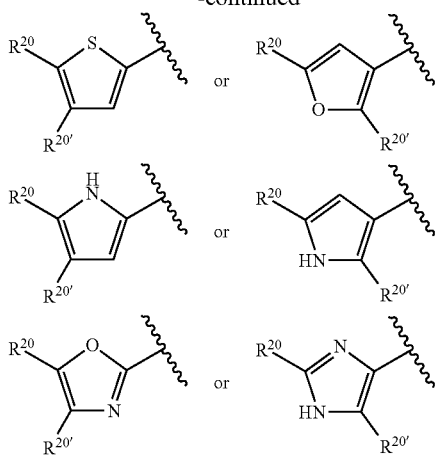

Bicyclic heteroaryl Ar ring radicals can include optionally substituted rings such as benzofuranyl, benzothiofuranyl, or benzopyrrolyl radicals, or other heteroaryl radicals such as the following:

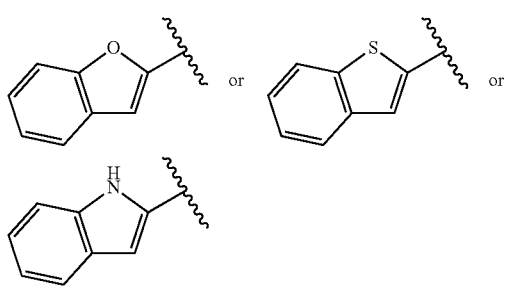

In the various embodiments of the compounds of Formula I and its various subgenera described herein, the Ar radical can be optionally substituted with one, two, or three $R^{20}$ substituent radicals, wherein each $R^{20}$ radical is independently selected from hydroxyl, $NH_2$, SH, halogen, or a $C_1$-$C_4$ organic radical. Suitable subclasses of the $C_1$-$C_4$ organic radicals include alkyl, alkoxyl, alkoxy-alkyl, hydroxyalkyl, haloalkyl, CN, $CO_2H$, CHO, $COR^{21}$, $CO_2R^{21}$, $NHR^{21}$, $NR^{21}R^{21}$, $SR^{21}$, $S(O)R^{21}$, and $SO_2R^{21}$ radicals, wherein $R^{21}$ and $R^{21'}$ are independently selected alkyls. In some embodiments of the compounds of Formula (I), the $R^{20}$ and/or $R^{20'}$ radicals are independently selected from hydroxy, fluoro, chloro, $NH_2$, $NHCH_3$, $N(CH_3)_2$, $CO_2CH_3$, SEt, $SCH_3$, methyl, ethyl, isopropyl, trifluoromethyl, methoxy, ethoxy, isopropoxy, and trifluoromethoxy groups. In yet additional embodiments, the $R^{20}$ and/or $R^{20'}$ radicals are independently selected from methyl, methoxy, and ethyl groups.

In many embodiments of the compounds of Formula (I), it is desirable that the Ar ring radical have a limited range of overall size and molecular weight. Accordingly, in some embodiments, the Ar radical comprises from 4 to 16 carbon atoms, or from 5 to 12 carbon atoms, or from 6 to 10 carbon atoms.

In many embodiments of the compounds of Formula (I), $hAr^1$ is an optionally substituted five or six-membered heteroaryl ring radical. The $hAr^1$ heteroaryl radicals comprise at least two ring carbon atoms that form bonds that link the heteroaryl ring of the $hAr^1$ radical to the other radicals of the compounds of Formula (I). The $hAr^1$ heteroaryl radicals also comprise one to three ring heteroatoms independently selected from O, N, or S, and any remaining members of the heteroaromatic ring are independently selected from $CR^6$, N, and $NR^7$, wherein the $R^6$ and $R^7$ radicals are further described below. Accordingly, the $hAr^1$ radicals could have as few as zero and as many as three $R^6$ and $R^7$ radicals. It is to be understood that all possible substitution patterns of the carbon, nitrogen, and sulfur atoms of the heteroaryl rings and their optional substituents that are reasonably chemically stable and are comestibly acceptable are within the scope of the invention.

The $hAr^1$ Radical

The $hAr^1$ radical of the compounds of Formula (I) and its various subgenuses is an optionally substituted monocyclic or bicyclic heteroaryl radical (as defined elsewhere herein) comprising one or two five or six membered heteroaryl rings, with one, two, or three optional $R^6$ or $R^7$ substitutents which may be attached at any of the positions of the $hAr^1$ heteroaryl ring radical other than those used to bond $hAr^1$ to the Ar and/or Y radicals, and also to the X radical.

In some embodiments of the compounds of Formula (I) and its subgenera, the $hAr^1$ radicals are an optionally substituted six membered heteroaryl radical such as $hAr^1$ is a pyridyl, pyrazinyl, pyridazinyl, or pyrimidinyl radical having the structure:

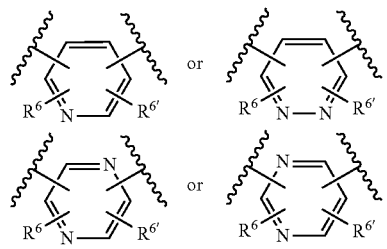

wherein the optional $R^6$ and $R^{6'}$ substituent radicals can be defined as disclosed below. In many embodiments of the compounds of Formula (I), the pyridyl, pyrazinyl, pyridazinyl, or pyrimidinyl radicals are unsubstituted, but may be bonded to the neighboring groups in any geometry, as illustrated below:

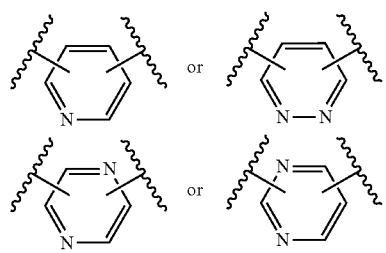

More specifically, the pyridyl, pyrazinyl, pyridazinyl or pyrimidinyl radicals include but are not limited to the following exemplary structures:

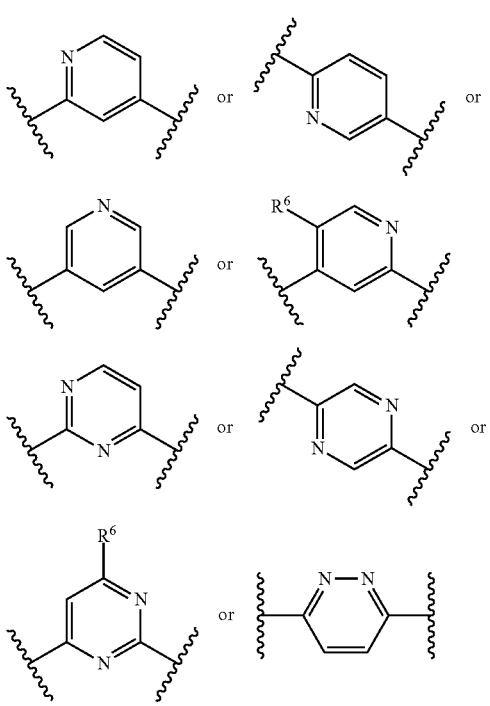

In some related embodiments of the compounds of Formula (I) and its subgenera, the hAr¹ radicals are an optionally substituted five membered heteroaryl radical such as a furanyl, thiofuranyl, or pyrrolyl radical, which include but are not limited to the following exemplary structures:

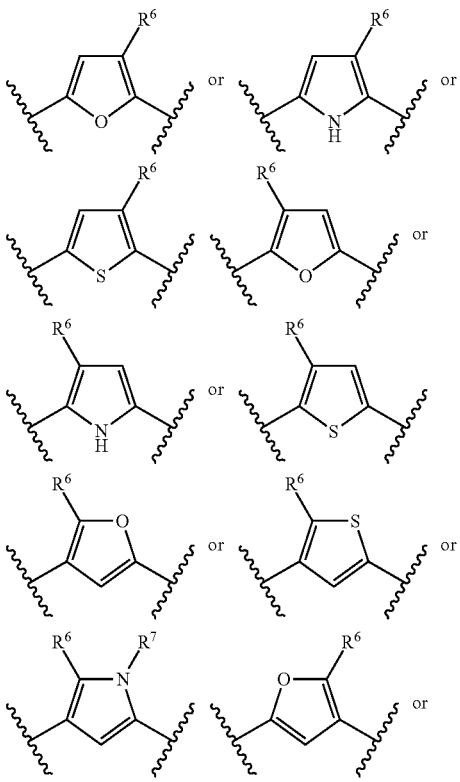

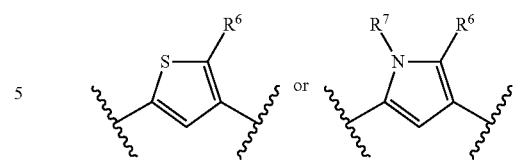

In the hAr¹ structures listed above, the $R^6$ radicals can be a halogen, or a $C_1$-$C_4$ organic radical. Suitable subclasses of the $C_1$-$C_4$ organic radicals include alkyl, alkoxyl, alkoxy-alkyl, hydroxyalkyl, haloalkyl, CN, $CO_2H$, CHO, $COR^{21}$, $CO_2R^{21}$, $NHR^{21}$, $NR^{21}R^{21'}$, $SR^{21}$, $S(O)R^{21}$, and $SO_2R^{21}$ radicals, wherein $R^{21}$ and $R^{21'}$ are independently selected alkyls. In some embodiments, $R^6$ is hydrogen or a $C_1$-$C_4$ alkyl or alkoxyl radical. In some embodiments, the $R^6$ radicals are independently selected from hydroxy, fluoro, chloro, $NH_2$, $NHCH_3$, $N(CH_3)_2$, $CO_2CH_3$, SEt, $SCH_3$, methyl, ethyl, isopropyl, trifluoromethyl, methoxy, ethoxy, isopropoxy, and trifluoromethoxy groups. In many embodiments, $R^6$ is hydrogen. In the hAr¹ structures listed above, $R^7$ can be hydrogen or a $C_1$-$C_4$ alkyl radical, and in many embodiments, $R^7$ is hydrogen.

In many embodiments of the compounds of Formula (I), hAr¹ is an optionally substituted diazole or triazole radical having the structure:

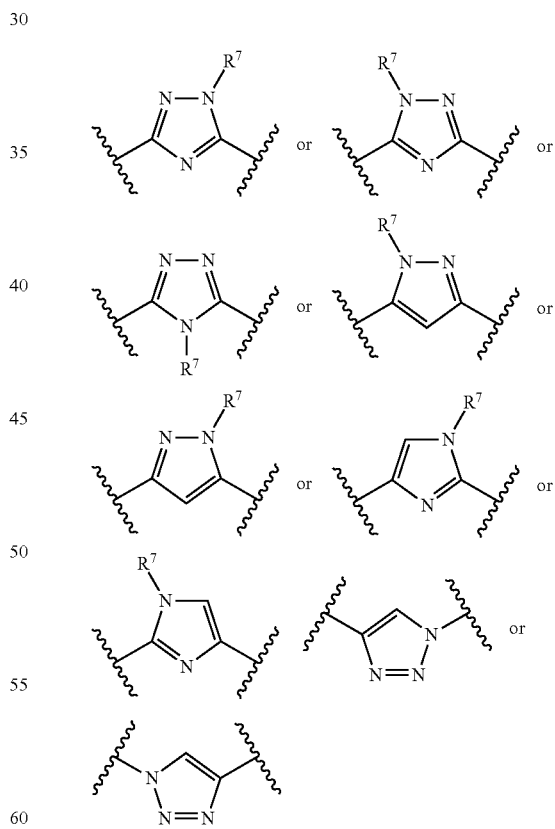

wherein $R^7$ is as is defined above. In many such embodiments, $R^7$ is hydrogen or a $C_1$-$C_4$ alkyl, or more preferably hydrogen. In certain preferred embodiments of the compounds of Formula (I), hAr¹ is an unsubstituted triazole having the structure:

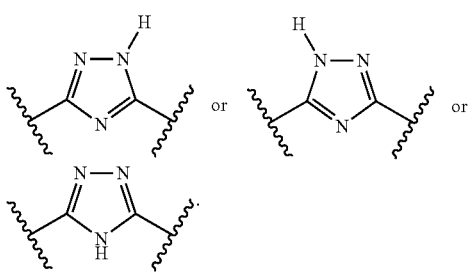

It should be understood that under some conditions of temperature, pH, and other variables, many of the heteroaryl compounds recited herein that comprise aromatic NH or OH groups, including the triazole compounds such as those listed above can and do tautomerize so as to equilibrate the three structures shown above, and that in these embodiments of the compounds of Formula (I) a real sample of the compound can and often does comprise the mixture of such tautomers. Accordingly, if only one tautomer is shown in this specification and/or the appended claims, it should be understood that the other tautomers are within the scope of such a claim unless it is clearly indicated to the contrary.

In other embodiments of the compounds of Formula I and its subgenera, the $hAr^1$ radical can be a tetrazole radical having the structure:

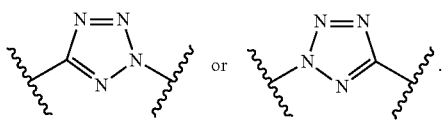 [SMILES: *c1nnn(*)n1 ; *c1nnn(*)n1]

In some embodiments of the compounds of Formula (I) and its subgenera, $hAr^1$ is an unsubstituted heteroaryl radical having one of the structures illustrated below:

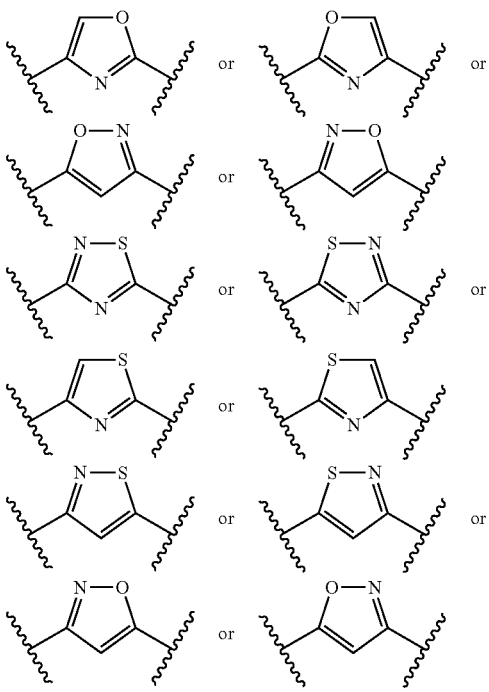

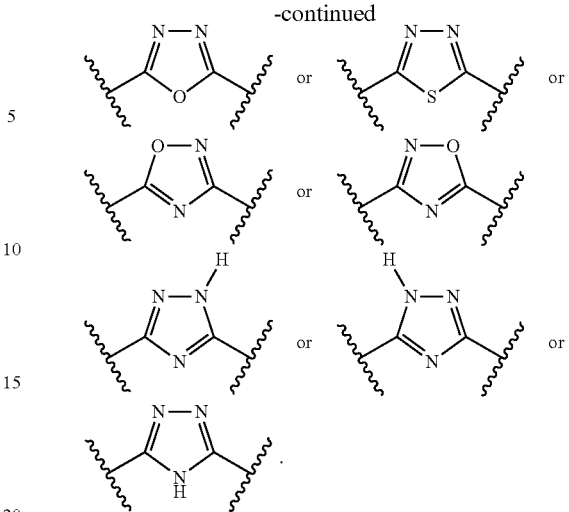

The hAr2 Radical

In many embodiments of the compounds of Formula (I), $hAr^2$ is an optionally substituted phenyl radical or and optionally substituted five or six-membered heteroaryl ring radical that is linked via the X and/or one or more $CR^3R^4$ groups to the $hAr^1$ radical described above.

In some embodiments of analogs of the compounds of Formula I, $hAr^2$ is a phenyl ring optionally substituted with 0, 1, 2, or 3 $R^{30}$ radicals independently selected from hydrogen, a halogen, or a $C_1$-$C_4$ organic radical. In some embodiments of the compounds of Formula I, the hAr2 radical is a heteroaryl radical as that term in defined elsewhere herein, and the $hAr^2$ heteroaryl radical has at least one ring carbon atom that is bonded to the X and optional $CR^3R^4$ groups, and at least one additional ring carbon atom, and at least one ring nitrogen atom. The remaining ring members of the five or six membered heteroaryl ring can be independently selected from $CR^{30}$, N, $NR^{31}$, O, and S, so long as the valences of the $CR^{30}$, N, $NR^{31}$, O, and S radicals are selected in a combination that results in the formation of a fully conjugated aromatic and delocalized heteroaryl ring having 4n+2 "π" electrons, a selection and/or condition that can be readily ascertained by those of ordinary skill in the art of organic chemistry.

In such embodiments of $hAr^2$, each $R^{30}$ can be independently selected from hydrogen, a halogen, or a $C_1$-$C_4$ organic radical and each $R^{31}$ can be independently selected from hydrogen, or a $C_1$-$C_4$ organic radical. Suitable subclasses of the $C_1$-$C_4$ organic radicals include alkyl, alkoxyl, alkoxyalkyl, hydroxyalkyl, haloalkyl, CN, $CO_2H$, CHO, $COR^{21}$, $CO_2R^{21}$, $NHR^{21}$, $NR^{21}R^{21'}$, $SR^{21}$, $S(O)R^{21}$, and $SO_2R^{21}$ radicals, wherein $R^{21}$ and $R^{21'}$ are independently selected alkyls. In some embodiments, each $R^{30}$ is independently selected from hydrogen or a $C_1$-$C_4$ alkyl or alkoxyl radical. In some embodiments, each $R^{30}$ radical can be independently selected from hydroxy, fluoro, chloro, $NH_2$, $NHCH_3$, $N(CH_3)_2$, $CO_2CH_3$, SEt, $SCH_3$, methyl, ethyl, isopropyl, trifluoromethyl, methoxy, ethoxy, isopropoxy, and trifluoromethoxy groups. In some embodiments, each $R^{30}$ is group is hydrogen. In the $hAr^2$ structures listed above, $R^{31}$ can be hydrogen or a $C_1$-$C_4$ alkyl radical, and in many embodiments, $R^{30}$ is hydrogen.

In some embodiments of the invention, $hAr^2$ is a five membered heteroaryl radical having one of the exemplary structures shown below:

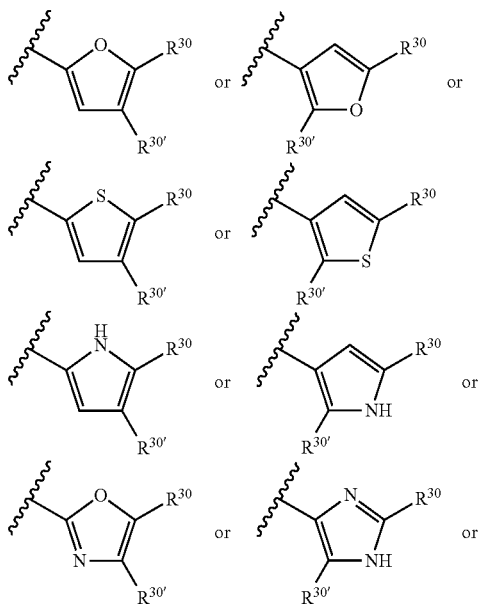

In many preferred embodiments of the invention, hAr² is a six membered heteroaryl radical such as a pyridyl, pyrazinyl, or pyrimidinyl radical, wherein the optional $R^{30}$ radicals are independently selected from hydroxy, SH, $NH_2$, a halogen an alkyl, alkoxyl, alkoxy-alkyl, hydroxyalkyl, haloalkyl, CN, $CO_2H$, CHO, $COR^{32}$, $CO_2R^{32}$, $NHR^{32}$, $NR^{32}R^{32'}$ or $SR^{32}$ radical, wherein $R^{32}$ and $R^{32'}$ are independently selected alkyls. Exemplary structures for the pyridyl, pyrazinyl, or pyrimidinyl radicals are shown below:

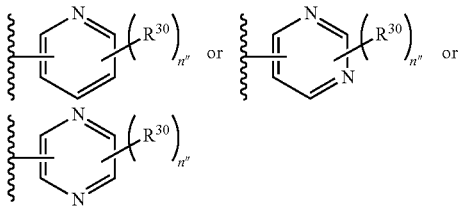

In certain preferred embodiments, hAr² is a 2-pyridyl, 2-pyrazinyl, or 2-pyrimidinyl radical, as shown below:

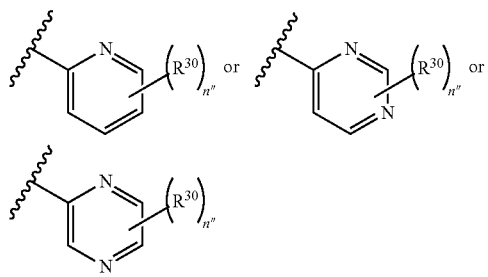

In some embodiments, each $R^{30}$ and/or $R^{30'}$ radical of the hAr² radical is independently selected from hydroxy, fluoro, chloro, $NH_2$, $NHCH_3$, $N(CH_3)_2$, $CO_2CH_3$, SEt, $SCH_3$, methyl, ethyl, isopropyl, trifluoromethyl, methoxy, ethoxy, isopropoxy, and trifluoromethoxy groups. In many embodiments, each $R^{30}$ is hydrogen (i.e. n" is zero).

In many preferred embodiments, hAr² is an unsubstituted 2-pyridyl radical, as shown below:

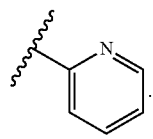

The Linker Groups X, Y, and $(CR_3R_4)$

As stated above, the hAr¹, hAr² and Ar ring groups can be linked together by bridging or linking groups X, Y, and/or $CR_3R_4$ as will now be further described. The Ar and hAr¹ groups can be optionally linked (when m=1) by a divalent "Y" atom or group that bridges Ar and hAr¹. The Y group generally consists of an atom with one bond to the Ar ring and another bond to the hAr¹ radical, and optionally other substituent groups, and can have many structures that include but are not limited to O, S, S(O), $SO_2$, $CR^1R^2$, or $NR^5$, so as to form compounds of Formula (I) having the following structures:

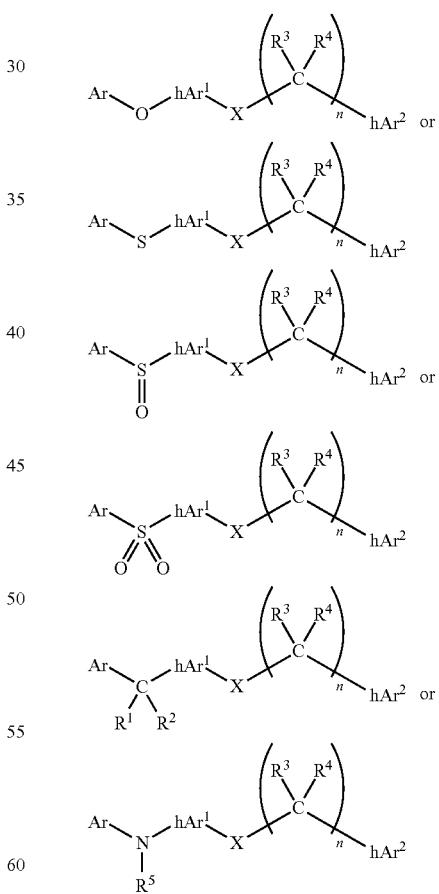

Alternatively, in many embodiments of the compounds of the invention, m=0, so that the Y group is absent and the Ar and hAr¹ rings are directly bonded/linked to each other as shown below:

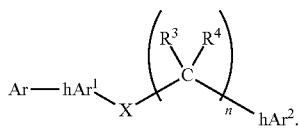

Unlike the "Y" group, the "X" group is typically present in the compounds of Formula (I), and is bonded to the hAr$^1$ group, and at least forms a bond or a link to the CR$^3$R$^4$ and/or hAr$^2$ heteroaryl ring group. Again, the X group generally comprises of a divalent atom or group with one bond to the hAr$^1$ ring and another bond to the CR$^3$R$^4$ and/or hAr$^2$ heteroaryl ring groups, and optionally other substituent groups, so as to form a link or bridge between hAr$^1$ and CR$^3$R$^4$ and/or hAr$^2$ heteroaryl ring groups. The X group can have many structures that include but are not limited to O, S, S(O), SO$_2$, CR$^8$R$^9$, or NR$^{10}$, so as to form compounds of Formula (I) having the following structures:

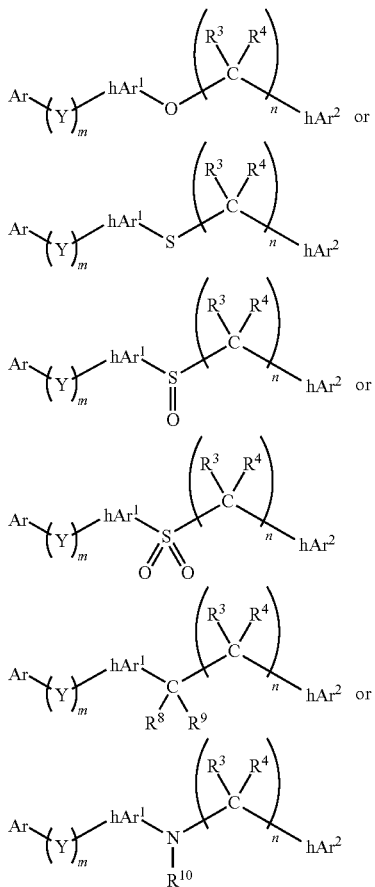

In some embodiments, is X is S, NH, or O, and in many preferred embodiments, X is S.

Lastly, the CR$^3$R$^4$ groups are optional (i.e. n can be zero, one, two, or three) bridging groups that are bonded to the X group and bond or link it to the hAr$^2$ heteroaryl ring. It is to be understood that unless there is a clear and contrary indication in the claims, if there is more than one CR$^3$R$^4$ group in a given molecule, the R$^3$ and R$^4$ substitutents can be independently chosen for each CR$^3$R$^4$ group present. In some embodiments, n is two, and would result in compounds having the following structure:

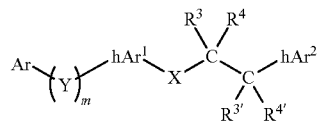

In many embodiments, n is one, so as to produce a subgenus of the compounds of Formula (I) having the structure:

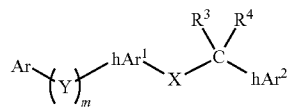

In many embodiments, m is zero and n is one, so as to produce a subgenus of the compounds of Formula (I) having the structure:

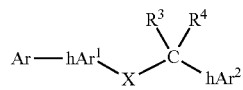

In the foregoing discussion, certain R$^1$-R$^{10}$ substituent groups have been defined in connection with other features of the linked heteroaryl compounds of Formula (I). In general, each of substitutent groups can be selected independently from the other groups. More specifically R$^1$, R$^2$, R$^3$, R$^4$, R$^8$ and R$^9$ can be independently selected from inorganic radicals or groups that include hydrogen, oxygen, hydroxyl, NH$_2$, SH, or a halogen (fluorine, chlorine, bromine, or iodine), or a C$_1$-C$_4$ organic radical. R$^7$ and R$^{10}$ can be independently selected from hydrogen, hydroxyl, or a C$_1$-C$_4$ organic radical, and R$^6$ can be hydrogen, halogen, or a C$_1$-C$_4$ organic radical. Suitable C$_1$-C$_4$ organic radicals include but are not limited to certain subgenuses of organic radicals such as an alkyl, alkoxyl, alkoxy-alkyl, hydroxyalkyl, haloalkyl, CN, CO$_2$H, CHO, COR$^x$, CO$_2$R$^x$, NHR$^x$, NR$^x$R$^{x'}$, SR$^x$, S(O)R$^x$, and SO$_2$R$^x$ wherein R$^x$ is an alkyl. In some embodiments, the C$_1$-C$_4$ organic radicals are selected from NHCH$_3$, N(CH$_3$)$_2$, CO$_2$CH$_3$, SEt, SCH$_3$, methyl, ethyl, isopropyl, trifluoromethyl, methoxy, ethoxy, isopropoxy, and trifluoromethoxy groups. In many embodiments, one or all of R$^1$-R$^{10}$ are hydrogen.

In certain preferred embodiments of the linked heteroaryl compounds of Formula (I), m=0 (i.e. the Y group is absent), n=1 and the R$^3$ and R$^4$ groups are hydrogen so as to form a single methylene group that links the X and hAr$^2$ rings, and Ar, hAr$^1$ and hAr$^2$ are limited to certain preferred aromatic ring systems, to form a preferred subgenus of linked heteroaryl compound having Formula (IA) as shown below:

(IA)

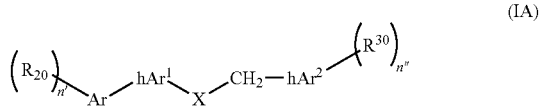

wherein
i) n' is zero, one, two, or three, and each R$_{20}$ is independently selected from the group consisting of hydroxy, SH, NH$_2$, a halogen, or a C$_1$-C$_4$ organic radical, ii) n" is zero, one, two, or three, and each $R_{30}$ is independently selected from the group consisting of hydroxy, SH, $NH_2$, a halogen, or a $C_1$-$C_4$ organic radical, iii) X is NH, O, S, S(O), $SO_2$, or $CH_2$, iv) Ar is a phenyl, pyridyl, pyrazinyl, pyrimidinyl, furanyl, thiofuranyl, pyrrolyl, benzofuranyl, benzothiofuranyl, or benzopyrrolyl ring v) $hAr^1$ has the structure

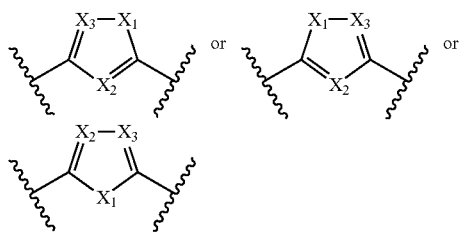

(1) $X_1$ is NH, O, or S,
(2) $X_2$ is N or $CR^6$ wherein $R^6$ is hydrogen, a halogen, or a $C_1$-$C_4$ organic radical,
(3) $X_3$ is N or $CR^6$ wherein $R^6$ is hydrogen, a halogen, or a $C_1$-$C_4$ organic radical, and vi) $hAr^2$ is a pyridyl, pyrazinyl, or pyrimidinyl ring.

As is apparent from the disclosure of the compounds of Formula (IA) above, the $hAr^1$ ring radical a subgenus of five-membered heteroaryls, as defined by the selection/identity of the $X_1$, $X_2$, and $X_3$ atoms, radicals, or groups. In certain narrower subgenuses, $X_1$ is NH. In other narrower subgenuses, $X_2$ can be N or CH, while $X_3$ is independently N or CH. In some preferred subgenuses, $X_2$ and $X_3$ are N.

In other preferred subgenuses, $X_1$ is NH, and $X_2$ and $X_3$ are N, so that the resulting $hAr^1$ ring is a triazole ring radical having the structure shown below:

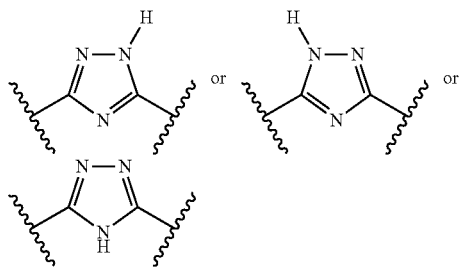

wherein it is to be recognized that tautomerism may, at least under some conditions, result in a mixture of the three triazole groups in the compounds of Formula (IA).

Additionally, in some embodiments of the compounds of Formula (IA), Ar is preferably a phenyl or furanyl radical, and the X group is S, NH, or O, or more preferably S or O. In some preferred embodiments of the compounds of Formula (IA), $hAr^2$ is a 2-pyridinyl radical having the structure:

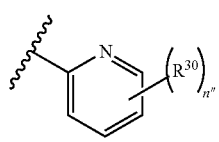

wherein n" is preferably 1 or 0.

In many embodiments of the compounds of Formula (IA), the $R^{20}$ and/or $R^{30}$ radicals are independently selected from hydroxy, SH, $NH_2$, a halogen, alkyl, alkoxyl, alkoxy-alkyl, hydroxyalkyl, haloalkyl, CN, $CO_2H$, CHO, $COR^x$, $CO_2R^x$, $NHR^x$, $NR^xR^{x'}$, or $SR^1$ radical, wherein $R^x$ is an alkyl, or even more preferably, the $R^{20}$ and/or $R^{30}$ radicals are independently selected from the group consisting of a hydroxy, fluoro, chloro, $NH_2$, $NHCH_3$, $N(CH_3)_2$, $CO_2CH_3$, SEt, $SCH_3$, methyl, ethyl, isopropyl, trifluoromethyl, methoxy, ethoxy, isopropoxy, and trifluoromethoxy group.

Another preferred subgenus of the compounds of Formula (I) are the triazole compounds of Formula (IB) shown below:

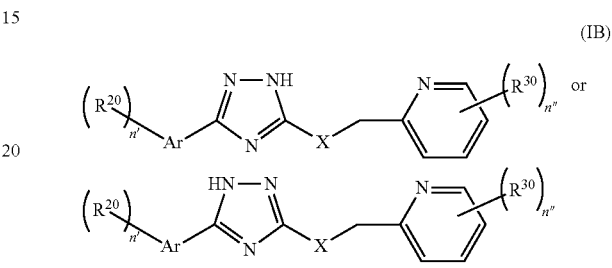

(IB)

wherein i) n' is zero, one, two, or three, and each $R^{20}$ is independently selected from hydroxy, SH, $NH_2$, a halogen, and a $C_1$-$C_4$ radical selected from an alkyl, alkoxyl, alkoxy-alkyl, hydroxyalkyl, haloalkyl, CN, $CO_2H$, CHO, $COR^{21}$, $CO_2R^{21}$, $NHR^{21}$, $NR^{21}R^{21'}$, or $SR^{21}$ radical, wherein $R^{21}$ and $R^{21'}$ is an alkyl, ii) n" is zero, one, two, or three, and each $R^{30}$ is independently selected from hydroxy, SH, $NH_2$, a halogen, and a $C_1$-$C_4$ radical selected from an alkyl, alkoxyl, alkoxy-alkyl, hydroxyalkyl, haloalkyl, CN, $CO_2H$, CHO, $COR^{32}$, $CO_2R^{32}$, or $SR^{32}$ radical, wherein $R^{32}$ and $R^{32'}$ is an alkyl, iii) X is NH, O, S, S(O), $SO_2$, or $CH_2$, iv) Ar is a phenyl, pyridyl, pyrazinyl, pyrimidinyl, furanyl, thiofuranyl, or pyrrolyl ring, or a comestibly acceptable salt thereof.

In yet other embodiments, the invention relates to a subgenus of the compounds of Formula (I) wherein $hAr^1$ is a triazole ring, but both the X and Y linker groups are present, as illustrated by the compounds of Formula (IC) shown below:

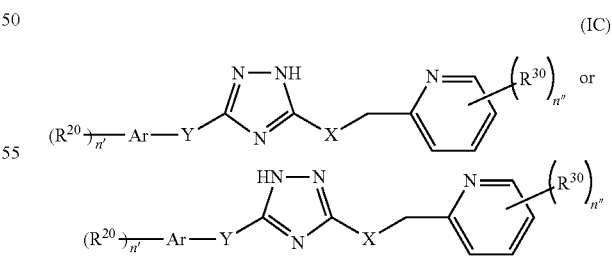

(IC)

wherein i) n' is zero, one, two, or three, and each $R^{20}$ is independently selected from the group consisting of hydroxyl, SH, $NH_2$, a halogen, or a $C_1$-$C_4$ organic radical, ii) n" is zero, one, two, or three, and each $R^{30}$ is independently selected from the group consisting of OH, SH, $NH_2$, a halogen, or a $C_1$-$C_4$ organic radical, iii) X is NH, O, S, S(O), SO$_2$, or CR$^8$R$^9$, wherein R$^8$ and R$^9$ are independently selected from hydrogen, oxygen, hydroxyl, NH$_2$, a halogen, or a C$_1$-C$_4$ organic radical,
iv) Y is NH, O, S, S(O), SO$_2$, or CR$^8$R$^9$, wherein R$^8$ and R$^9$ are independently selected from hydrogen, oxygen, hydroxyl, NH$_2$, a halogen, or a C$_1$-C$_4$ organic radical,
v) Ar is a phenyl, pyridyl, pyrazinyl, pyrimidinyl, furanyl, thiofuranyl, or pyrrolyl ring, or a comestibly acceptable salt thereof.

In additional embodiments, the invention relates to a subgenus of the compounds of Formula (I) wherein hAr$^1$ is a six membered heteroaryl comprising one or two nitrogen atoms, as illustrated by the compounds of Formula (ID) shown below:

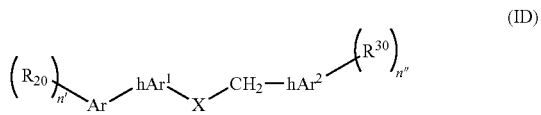

(ID)

and wherein
i) n' is zero, one, two, or three, and each R$^{20}$ is independently selected from the group consisting of hydroxy, SH, NH$_2$, a halogen, or a C$_1$-C$_4$ organic radical,
ii) n'' is zero, one, two, or three, and each R$^{30}$ is independently selected from the group consisting of hydroxy, SH, NH$_2$, a halogen, or a C$_1$-C$_4$ organic radical,
iii) X is NH, O, S, S(O), SO$_2$, or CH$_2$,
iv) Ar is a phenyl, pyridyl, pyrazinyl, pyrimidinyl, furanyl, thiofuranyl, pyrrolyl, benzofuranyl, benzothiofuranyl, or benzopyrrolyl ring
v) hAr$^1$ has the structure:

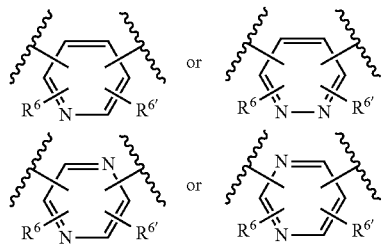

wherein R$^6$ and R$^{6'}$ are independently selected from hydrogen, a halogen, or a C$_1$-C$_4$ organic radical, and
vi) hAr$^2$ is a a pyridyl, pyrazinyl, or pyrimidinyl ring.

In some embodiments of the compounds Formula (ID), Ar is a phenyl ring, n' is one or two, and each R$_{20}$ is independently selected from the group consisting of methyl, ethyl, isopropyl, trifluoromethyl, methoxy, trifluoromethoxy, and ethoxy. In other embodiments of the compounds Formula (ID), Ar is a phenyl ring comprising an alkylene dioxy ring fused thereto, such as Ar groups having the structure:

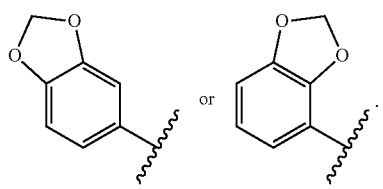 [SMILES: *c1ccc2c(c1)OCO2 ; *c1cccc2c1OCO2]

In some embodiments of the compounds Formula (ID), Ar is a furanyl ring, n' is one or two, and each R$_{20}$ is independently selected from the group consisting of methyl, ethyl, isopropyl, trifluoromethyl, methoxy, trifluoromethoxy, and ethoxy.

In some embodiments of the compounds Formula (ID), hAr$^1$ is an unsubstituted pyridyl, pyrazinyl, pyridazinyl, or pyrimidinyl radical having the structure:

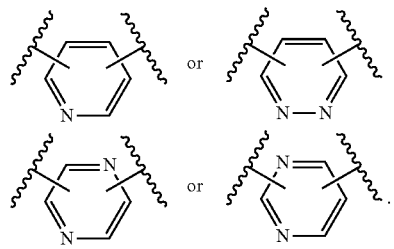

In some embodiments of the compounds of Formula (ID), hAr$^2$ is an optionally substituted pyridyl radical having the structure:

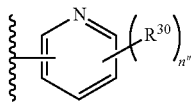

wherein each R$_{30}$, if present, is independently selected from the group consisting of a hydroxy, fluoro, chloro, NH$_2$, NHCH$_3$, N(CH$_3$)$_2$, CO$_2$CH$_3$, SEt, SCH$_3$, methyl, ethyl, isopropyl, trifluoromethyl, methoxy, ethoxy, isopropoxy, and trifluoromethoxy.

Preferably, the pyridinyl radical is a 2-pyridinyl radical having the structure:

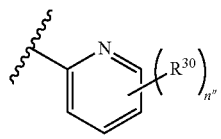

wherein n'' is 0 or 1, and more preferably n'' is 0.

In many embodiments of the compounds of Formula (I) and its subgenuses (IA), (IB), (IC), and (ID) disclosed above, the linked heteroaryl compounds are preferably formulated as "small molecules" as compared to many biological molecules, and can have a variety of limitations on their overall absolute physical size, molecular weight, and physical characteristics, so that they can be at least somewhat soluble in aqueous media, and are of appropriate size to effectively bind to the relevant heterodimeric T1R1/T1R3 taste receptors.

Therefore, in many embodiments of the compounds of Formula (I) and/or it's various subgenuses, the molecular weight of the compounds of Formula (I) should be less than about 800 grams per mole, or in further related embodiments less than or equal to about 700 grams per mole, 600 grams per mole, 500 grams per mole, 450 grams per mole, 400 grams per mole, 350 grams per mole, or 300 grams per mole. Similarly, the compounds of Formula (I) can have preferred ranges of molecular weight, such as for example from about 175 to about 500 grams per mole, from about 200 to about 450 grams per mole, from about 225 to about 400 grams per mole, from about 250 to about 350 grams per mole.

The molecular weight and/or hydrophilic character of the compounds can also be modified by placing limits on the number of carbon atoms in the compounds of the invention. Accordingly, in some embodiments, the compounds of Formula (I) have between 10 and 22 carbon atoms, or alternatively between 12 and 20 carbon atoms.

Moreover, it is desirable that the compounds of Formula (I) and its subgenuses and species have sufficient polarity and/or polar functional groups so that they are at least somewhat soluble in aqueous biological fluids, such as saliva. A well known indicator of such water solubility is the $\log^{10}$ of the partition coefficient of a given compound between n-octanol and water, a parameter which can be readily and quickly estimated by computer-based calculations from the structure of the compound by many modern chemical software packages, so that "designing" compounds with sufficient estimated water solubility does not in this modern age typically require actual synthesis of the compounds, though experimental confirmation of the water solubility of the compounds is desirable once promising candidate compounds have been synthesized. Accordingly, in some embodiments of the invention, the $\log^{10}$ of the partition coefficient of the compound between n-octanol and water is less than 5.5, preferably less than 5.0, or less than 4.5.

For the various embodiments and/or subgenuses of the compounds of Formula (I), it is hereby specifically contemplated that any of subgenuses and/or species of compounds of Formula (I) described below can, either in their specified form or as a comestibly acceptable salt, be combined in an effective amount with a comestible product or precursor thereof by the processes and/or methods described elsewhere herein, or by any such other processes as would be apparent to those of ordinary skill in preparing comestible or medicinal products or precursor thereof, to form a savory flavor modified comestible product, or a precursor thereof.

Comestibly Acceptable Compounds, Salts Thereof, and/or Comestible Compositions

Many of the linked heteroaryl compounds of Formula (I) or its various enumerated subgenuses comprise acidic or basic groups, with the result that those acidic or basic groups can be neutralized by corresponding commestibly acceptable acids or bases to form comestibly acceptable salts, and the compounds of Formula (I) can be administered in the form of the comestibly acceptable salts, many of which have been recognized as GRAS (generally recognized as safe).

Additionally, depending on the acidic or basic character ("pH") of the comestible compositions in which the compounds of Formula (I) are formulated, they may be present as salts which preferably are comestibly acceptable salts. The compounds of Formula (I) having acidic substituent groups, such as carboxylic acids, will tend (at near neutral physiological pH) to be present in solution in the form of anionic carboxylates, and therefore will in preferred embodiments have an associated comestibly and/or pharmaceutically acceptable cation, many of which are known to those of ordinary skill in the art. Such comestibly acceptable cations include alkali metal cations (lithium, sodium, and potassium cations), alkaline earth metal cations (magnesium, calcium, and the like), or ammonium $(NH_4)^+$ or organically substituted ammonium cations such as $(R-NH_3)^+$ cations.

The compounds of Formula (I) having basic substituent groups, such as amino groups or heterocyclic rings comprising nitrogen atoms, will tend (at near neutral physiological pH, or at the acidic pH common in many foods) to be actually present in solution in the form of cationic ammonium groups, and therefore will in preferred embodiments have an associated comestibly acceptable anion, many of which are known to those of ordinary skill in the art. Such comestibly acceptable anionic groups include the anionic form of a variety of carboxylic acids (acetates, citrates, tartrates, anionic salts of fatty acids, etc.), halides (especially fluorides or chlorides), nitrates, phosphates, sulfates, and the like.

The linked heteroaryl compounds of Formula (I) and its various subgenuses, and their salts, should preferably be comestibly acceptable, i.e. deemed suitable for consumption in food or drink from the perspective of giving unmodified comestible compositions an improved and/or pleasing savory taste, and would not be significantly toxic or causes unpleasant or undesirable pharmacological or toxicological effects on an animal or human at the typically low concentrations they are employed as flavoring agents for the comestible compositions.

The typical method of demonstrating that a flavorant compound is comestibly acceptable is to have the compound tested and/or evaluated by an Expert Panel of the Flavor and Extract Manufacturers Association and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference.

When being evaluated in the FEMA/GRAS process, a new flavorant compound is typically tested for any adverse toxic effects on laboratory rats when fed to such rats for at least about 90 days at a concentration at least 100-fold higher, or 1000-fold, or higher concentrations than the proposed maximum allowable concentration of the compound in a particular category of food products being considered for approval. For example, such testing of the compounds of Formula (I) might involve combining the compound with rat chow and feeding it to laboratory rats such as Crl:CD(SD)IGS BR rats, at a concentration of about 100 milligrams/kilogram body weight/day for 90 days, and then sacrificing and evaluating the rats, and using various known medical testing procedures to show that the compound of Formula (I) causes no adverse toxic effects on the rats.

The compounds of Formula (I) are not, at least in most embodiments, currently known to have independent pharmaceutical or biological activity for the treatment of diseases in animals or humans, or intended to be administered or marketed as pharmaceutically active agents. The linked heteroaryl compounds of Formula (I) and its various subgenuses might nevertheless, in some embodiments, be used and marketed as flavorants to modify or improve the taste of certain types of "pharmaceutical" or "nutraceutical" compositions, such as vitamin enriched comestible compositions, such as soups, and in many such embodiments the compounds of the present invention would often be formulated in combination with MSG or other savory tastant compounds, in order to enhance the savory flavor of such neutraceutical compositions.

In view of the discussion above, if it has already been discovered or is later discovered that one or more of the compounds of Formula (I) or a pharmaceutical composition thereof is known and/or has pharmaceutical or biological activity for the treatment of diseases, then in connection with claims to methods of modifying the savory taste of comestible compositions that encompass the use of such known compounds, and in connection with claims to comestible compositions derived from the aforementioned methods, additional embodiments of such methods or comestible compositions in connection with the current invention can include a recitation that the methods and compositions claimed herein must also comprise MSG.

The Compounds of the Invention as Savory Taste Enhancers

The linked heteroaryl compounds of Formula (I) and its various compound sub-genuses and species, as described above are intended to be savory flavorant compounds or flavor modifiers for comestible products. As is apparent from the teachings and Examples herein, many compounds of Formula (I) are agonists of an hT1R1/hT1R3 "savory" receptor, at least at concentrations of about 100 μM or less. Accordingly many of the amide compounds of Formula (I) have a significant savory flavor independent of the presence or absence of MSG, and therefore can have utility as independent savory flavorants or flavor enhancers.

Nevertheless, it is preferable to use as little of such artificial flavorants as possible, so as to minimize both cost and any undesirable health side effects of administration of the compounds of Formula (I) at high concentration levels. Accordingly, it is desirable to test the compounds of Formula (I) for their effectiveness as taste receptor agonists at lower concentration levels, so as to identify the best and most effective linked heteroaryl compounds of Formula (I). As was disclosed in WO 03/001876, and U.S. Patent Publication US 2003-0232407 A1, hereby incorporated herein by reference and as described hereinbelow, laboratory procedures now exist for measuring the agonist activities of compounds for an hT1R1/hT1R3 "savory" receptor. Such measurement methods typically measure an "$EC_{50}$", i.e. the concentration at which the compound causes 50% activation of the relevant receptor.

Preferably, the linked heteroaryl compounds of Formula (I) that are savory flavor modifiers have an $EC_{50}$ for the hT1R1/hT1R3 receptor of less than about 10 μM. More preferably, such compounds have an $EC_{50}$ for the hT1R1/hT1R3 receptor of less than about 5 μM, 3 μM, 2 μM, 1 μM, or 0.5 μM.

In some embodiments, the compounds of Formula (I) are savory flavor modulators or enhancers of the agonist activity of monosodium glutamate for an hT1R1/hT1R3 receptor. Hereinbelow is described an assay procedure for so-called $EC_{50}$ ratios, i.e. for dissolving a compound of Formula (I) in water containing MSG, and measuring the degree to which the amide compound lowers the amount of MSG required to activate 50% of the available hT1R1/hT1R3 receptors. Preferably, the compounds of Formula (I), when dissolved in an aqueous solution comprising about 1 μM of the linked heteroaryl compound will decrease the observed $EC_{50}$ of monosodium glutamate for an hT1R1/hT1R3 receptor expressed in an HEK293-Gα15 cell line by at least 50%, i.e. the compound will have an EC50 ratio of at least 2.0, or preferably 3.0, 5.0, or 7.0.

The above identified assays are useful in identifying the most potent of the compounds of Formula (I) for savory taste modifier or enhancer properties, and the results of such assays are believed to correlate well with actual savory taste perception in animals and humans, but ultimately the results of the assays can be confirmed, at least for the most potent of the compounds of Formula (I), by human taste testing. Such human taste testing experiments can be well quantified and controlled by tasting the candidate compounds in aqueous solutions, as compared to control aqueous solution, or alternatively by tasting the compounds of the inventions in actual food compositions.

Accordingly, in order to identify the more potent of the savory taste modifiers or agents, a water solution comprising a savory flavor modifying amount of any particular linked heteroaryl compound of Formula (I) or one of its subgenuses should have a savory taste as judged by the majority of a panel of at least eight human taste testers.

Correspondingly, in order to identify the more potent of the savory taste enhancers, a water solution, comprising a savory flavor modifying amount of a compound of Formula (I) and 12 mM monosodium glutamate, would have an increased savory taste as compared to a control water solution comprising 12 mM monosodium glutamate, as determined by the majority of a panel of at least eight human taste testers. Preferably, in order to identify the more potent of the savory taste enhancers, a water solution comprising a savory flavor modifying amount (preferably about 30, 10, 5, or 2 ppm) of the compound of Formula (I) and 12 mM monosodium glutamate will have an increased savory taste as compared to a control water solution comprising 12 mM monosodium glutamate and 100 μM inosine monophosphate, as determined by the majority of a panel of at least eight human taste testers.

Using the Compounds of Formula (I) to Prepare Comestible Compositions

Flavors, flavor modifiers, flavoring agents, flavor enhancers, savory ("umami") flavoring agents and/or flavor enhancers, prepared from the compounds of Formula I and its various subgenera and species compounds herein, and their commestibly acceptable salts, and compositions thereof, have application in foods, beverages and other comestible compositions wherein savory compounds, especially MSG, IMP, or GMP are conventionally utilized. These compositions include compositions for human and animal consumption. This includes food or drinks (liquids) for consumption by agricultural animals, pets and zoo animals.

Those of ordinary skill in the art of preparing and selling comestible compositions (i.e edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those comestible compositions. Such a list of terms of art is enumerated below, and it is specifically contemplated hereby that the various subgenuses and species of the compounds of Formula (I) could be used to modify or enhance the savory flavors of the following list comestible compositions, either singly or in all reasonable combinations or mixtures thereof:

One or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurised milk, full fat fresh/pasteurised milk, semi skimmed fresh/pasteurised milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavoured fromage frais and quark, savoury fromage frais and quark, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and Seed oil, cooking fats, butter, margarine, spreadable oils and fats, functional spreadable oils and fats, sauces, dressings and condiments, tomato pastes and purées, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Preferably, the compounds of Formula (I) can be used to modify or enhance the savory flavor of one or more of the following sub-genuses of comestible compositions: confectioneries, bakery products, ice creams, dairy products, savory snacks, snack bars, meal replacement products, ready meals, soups, pastas, noodles, canned foods, frozen foods, dried foods, chilled foods, oils and fats, baby foods, or spreads, or a mixture thereof.

In general an ingestible composition will be produced that contains a sufficient amount of at least one compound within the scope of Formula (I) or its various subgenuses described hereinabove to produce a composition having the desired flavor or taste characteristics such as "savory" taste characteristics.

Typically at least a savory flavor modulating amount, of one or more of the compounds of Formula (I) will be added to the comestible product, so that the savory flavor modified comestible product has an increased savory taste as compared to the comestible product prepared without the compound of Formula (I), as judged by human beings or animals in general, or in the case of formulations testing, as judged by a majority of a panel of at least eight human taste testers, via procedures described elsewhere herein.

The concentration of savory flavoring agent needed to modulate or improve the flavor of the comestible product or composition will of course vary dependent on many variables, including the specific type of ingestible composition, what savory compounds are already present and the concentrations thereof, the amount of MSG already present, and the enhancer effect of the particular compound on such savory compounds. As noted, a significant application of the compounds of Formula (I) is for modulating (inducing, enhancing or inhibiting) the savory tastes or other taste properties of other natural or synthetic savory tastants, especially MSG. A broad range of concentrations of the compounds of Formula (I) can be employed to provide such savory taste enhancement, i.e. from about 0.001 ppm to 100 ppm, or narrower alternative ranges from about 0.1 ppm to about 10 ppm, from about 0.01 ppm to about 30 ppm, from about 0.05 ppm to about 15 ppm, from about 0.1 ppm to about 5 ppm, or from about 0.1 ppm to about 3 ppm.

Examples of foods and beverages wherein compounds according to the invention may be incorporated included by way of example the Wet Soup Category, the Dehydrated and Culinary Food Category, the Beverage Category, the Frozen Food Category, the Snack Food Category, and seasonings or seasoning blends.

"Wet Soup Category" means wet/liquid soups regardless of concentration or container, including frozen Soups. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrées including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

"Beverage Category" means beverages, beverage mixes and concentrates, including but not limited to, alcoholic and non-alcoholic ready to drink and dry powdered beverages.

Other examples of foods and beverages wherein compounds according to the invention may be incorporated included by way of example carbonated and non-carbonated beverages, e.g., sodas, fruit or vegetable juices, alcoholic and non-alcoholic beverages, confectionary products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like.

Additionally, the subject compounds can be used in flavor preparations to be added to foods and beverages. In preferred instances the composition will comprise another flavor or taste modifier such as a savory tastant.

Accordingly, in some embodiments, the inventions relate to methods for modulating the savory taste of a comestible product comprising:

a) providing at least one comestible product, or a precursor thereof, and
  i. combining the comestible product or precursor thereof with at least a savory flavor modulating amount of at least one compound of Formula (I) or any of its subgenuses, or a comestibly acceptable salt thereof, so as to form a modified comestible product.

The invention also relates to the modified comestible products produced by such processes, and similar processes for producing comestible products well known to those of ordinary skill in the art, especially if such compositions comprise MSG, and the compound is employed as a savory taste enhancer for the MSG also present in the composition.

The amide compounds of Formula (I) and its various subgenuses can be combined with or applied to the comestible or medicinal products or precursor thereof in any of innumerable ways known to cooks the world over, or producers of comestible or medicinal products. For example, the compounds of Formula (I) could be dissolved in or dispersed in or one one of many known comestibly acceptable liquids, solids, or other carriers, such as water at neutral, acidic, or basic pH, fruit or vegetable juices, vinegar, marinades, beer, wine, natural water/fat emulsions such as milk or condensed milk, edible oils and shortenings, fatty acids, certain low molecular weight oligomers of propylene glycol, glyceryl esters of fatty acids, and dispersions or emulsions of such hydrophobic substances in aqueous media, salts such as sodium chloride, vegetable flours, solvents such as ethanol, solid edible diluents such as vegetable powders or flours, and the like, and then combined with precursors of the comestible or medicinal products, or applied directly to the comestible or medicinal products.

Making the Linked Heteroaryl Compounds of Formula (I)

The starting materials used in preparing the compounds of the invention, i.e. the various structural subclasses and species of the compounds of the synthetic precursors of the linked heteroaryl compounds of Formula (I), especially the organic carboxylic acids and benzoic acids, isocyanates, and the various amines, anilines, amino acids, etc., are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haën, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive amination and the like. These manipulations are discussed in standard texts such as March's *Advanced Organic Chemistry* (3d Edition, 1985, Wiley-Interscience, New York), Feiser and Feiser's *Reagents for Organic Synthesis*, and in the various volumes and editions of *Methoden der Organischen Chemie* (Houben-Weyl), and the like. Many general methods for preparation of starting materials comprising variously substituted heterocyclic, hetereoaryl, and aryl rings (the precursors of Ar, hAr$^1$, and/or hAr$^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, *Protecting Groups in Organic Synthesis*, 3$^{rd}$ Ed., John Wiley & Sons (1999).

The following abbreviations used in the examples and elsewhere herein have the indicated meanings:
 CH$_3$CN=Acetonitrile
 CHCl$_3$=Chloroform
 DIC=N,N'-Diisopropylcarbodiimide
 DIPEA=Diisopropylethylamine
 DMAP=4-(dimethylamino)-pyridine
 DMF=N,N-dimethylformamide
 EDCI=1-(3-Dimethylaminopropyl)-3-ethylcarbodiimide hydrochloride
 DCM=Dichloromethane
  ESIMS=electron spray mass spectrometry
 E t$_3$N=triethylamine EtOAc=ethyl acetate
EtOH=Ethyl Alcohol
Fmoc=N-(9-fluorenylmethoxycarbonyl-
HCl=Hydrochloric acid
$H_2SO_4$=Sulfuric acid
HOBt=1-Hydroxybenzotriazole
MeOH=Methyl Alcohol
$MgSO_4$=magnesium sulfate
$NaHCO_3$=sodium bicarbonate
NaOH=Sodium Hydroxide
$Na_2SO_4$=Sodium Sulfate
Ph=phenyl
r.t.=room temperature
SPOS=solid phase organic synthesis
THF=tetrahydrofuran
TLC=thin layer chromatography
Alkyl Group Abbreviations
Me=methyl
Et=ethyl
n-Pr=normal propyl
i-Pr=isopropyl
n-Bu=normal butyl
i-Bu=isobutyl
t-Bu=tertiary butyl
s-Bu=secondary butyl
n-Pen=normal pentyl
i-Pen=isopentyl
n-Hex=normal hexyl
i-Hex=isohexyl
Polymer Supported Reagent Abbreviations
PS-Trisamine=Tris-(2-aminoethyl)amine polystyrene
PS-NCO=methylisocyanate polystyrene
PS-TsNHNH$_2$=toluensulfonylhydrazone polystyrene Example Procedures for Making the Heteroaryl Compounds of Formula (I)

Scheme 1A - Methods for Preparing 3,5-Disubstituted 1H-1,2,4-triazoles

METHOD A ($X_a$ = Cl):
1. thiosemicarbazide pyridine
2. aq. $NaHCO_3$

METHOD B ($X_a$ = OH)
1. Carbodiimide,
2. thiosemicarbazide pyridine
3. aq. $NaHCO_3$ As shown in Scheme 1A, carboxylic acid derivatives of the Ar radical can be activated by conversion to acid chlorides (METHOD A) or carbodiimide esters (METHOD B), which react with thiosemicarbazide providing intermediate triazolethiones that can reacts with alkyl substituted derivatives of $hAr^2$ comprising suitable leaving groups ("LG" such as chlorides, bromides, iodides, tosylates, and the like) to providing triazole derivatives having structures that are within the scope of Formula (I).

Scheme 1B- Alternative Method for Preparing 3,5-Disubstituted 1H-1,2,4-triazoles As shown in scheme 1B, 1,2,4-triazole derivatives (I) can be alternatively prepared in two steps from amide precursors of the Ar ring via treatment with strong bases, carbon disulfide and an electrophilic precursor of the $hAr^2$ radical to form an acylcarbonodithioimidate intermediate, which in presence of hydrazine is converted to the desired triazole product. (See M Sato et al., Synthesis, 7, 1981, 554-557).

Scheme 1C-Method for Preparing 3,4,5-trisubstituted-4H-1,2,4-triazoles

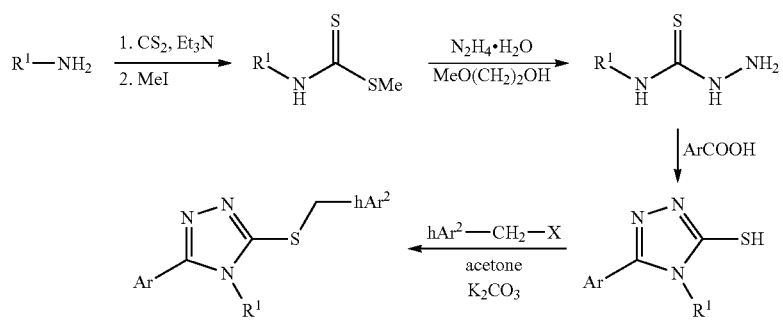

As shown in scheme 1C, an N-substituted triazole within the scope of Formula (I) can be obtained in multistep process starting from an amine precursor of the N-substituent for the triazole, by treatment with carbon disulfide and methyl iodide to provide a dithiocarbamate, which can be reacted with hydrazine to provide a thiosemicarbazide, which can be condensed with a carboxylic acid precursor of Ar, to give cyclic mercaptotriazole that can be alkylated using appropriate electrophilic precursors of hAr$^2$, such as an alkyl iodide. (See Ashton et al., J. Med. Chem. 1992, 35, 2103-2112).

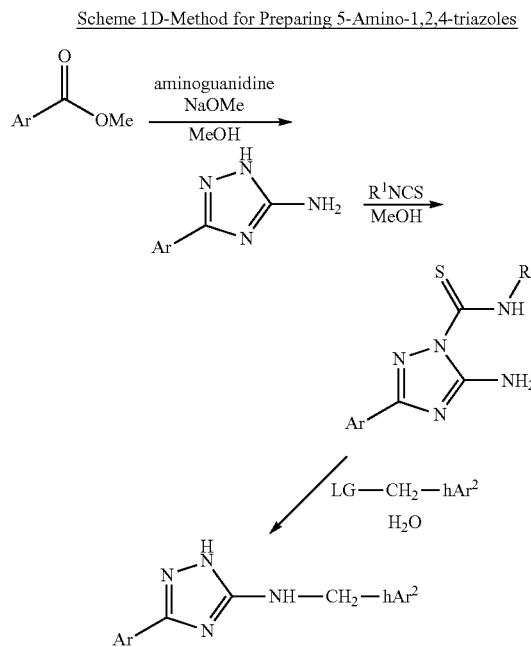

Scheme 1D-Method for Preparing 5-Amino-1,2,4-triazoles

As shown on scheme 1D, 1,2,4-triazol-5-aminoderivatives can be prepared in two steps from methylester precursors of Ar, by reaction with guanidine under basic conditions providing a 5-amino-triazole intermediate that reacts with electrophiles such as isothiocyanates to provide an N-thioacyl triazole compound, which can then be condensed with an electrophillic precursor of hAr$^2$ and hydrolyzed. (See Y. Naito et al., J. Med. Chem. 39, 15, 1996, 3019-3029).

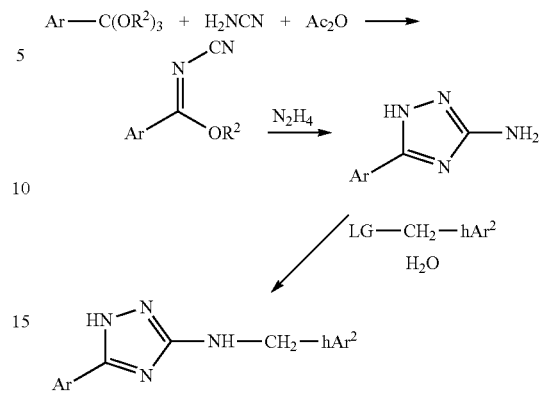

Scheme 1E-Alternative Method for Preparing 2 H-1,2,4-triazol-3-amines

As shown on scheme 1E, 1,2,4-triazol-5-aminoderivatives (I) can be alternatively prepared by reacting orthoester precursors of Ar with cyanoamine and acetic anhydride to provide an N-cyanomidate which is then reacted with hydrazine to provide the 3-amino-tetrazole, which can be reacted with electrophillic precursors of hAr$^2$. (See K. R. Husfmann et al., J. Org. Chem. 28, 1963, 1816-1821).

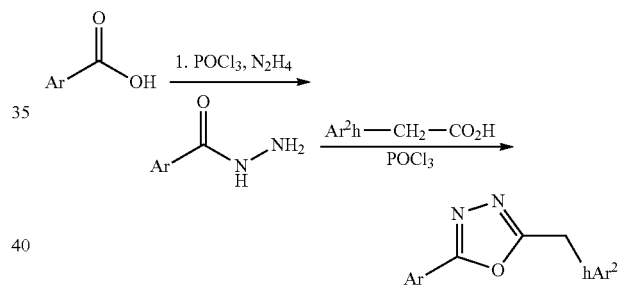

Scheme 2A-Method of Preparing 2,5-disubstituted-1,3,4-oxadiazoles

As shown in scheme 2A, 1,3,4-oxadiazoles (I) can be prepared from hydrazide precursors of Ar and acid chlorides precursors of hAr$^2$. (See B. G. Szczepankiewicz et al., J. Med. Chem. 2001, 44, 4416-4430).

Scheme 2B-Method of Preparing N,3-disubstituted 1-1,2,4-oxadiazol-5-amines

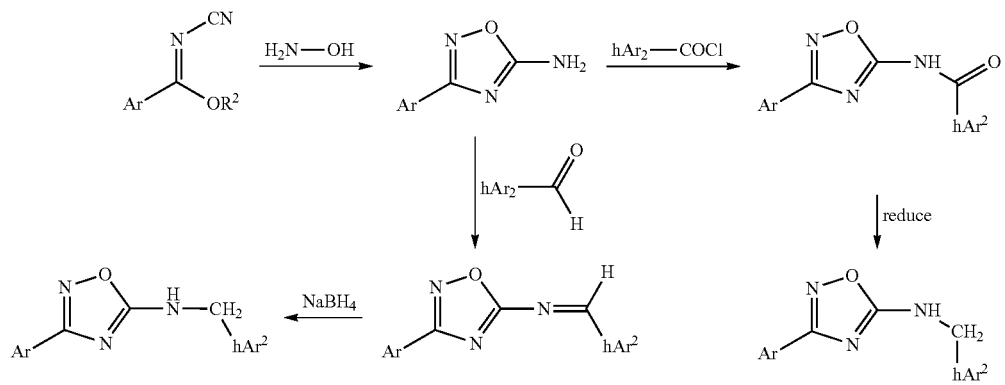

As shown in scheme 2B N-cyanomidates (prepared as shown above in Scheme 1E) react with hydroxylamine providing 5-amino-1,2,4-oxadiazoles (II) that can be alkylated or acylated to give N,3-disubstituted 1-1,2,4-oxadiazol-5-amines. (See K. R. Husfmann et al., J. Org. Chem. 28, 1963, 1816-1821).

As shown in scheme 3A oxadiazole intermediate (See preparation in Scheme 2B) can rearrange with sulphur nucleophiles under UV irradiation to provide 1,2,4-thiadiazol-5-amines. (See N. Vivona et. al., Tetrahedron 53, 37, 1997, 12629-12636).

Scheme 2C-Method of Preparing N,3-disubstituted 1-1,2,4-oxadiazol-5-amines

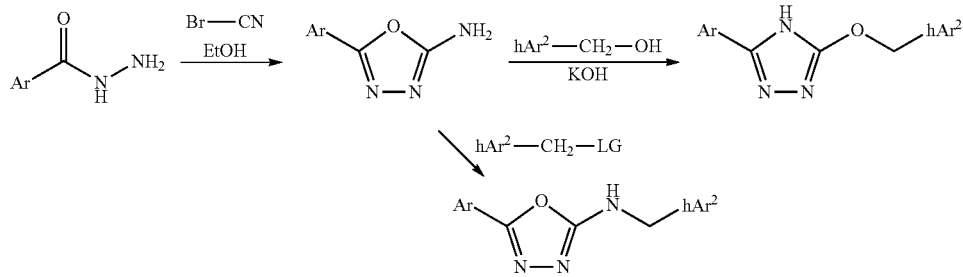

As shown in scheme 2C, hydrazide precursors of Ar can be treated with cyanogen bromide in EtOH to provide 1,3,4-oxadizolylamines that can be converted to substituted triazoles or oxadiazoles within the scope of the compounds of Formula (I). See PCT Patent Publication WO 02/078696 to Marino et al., page 14, published Oct. 10, 2002.

Scheme 3A-Method of Preparing N,3-disubstituted-1,2,4-thiadiazol-5-amines

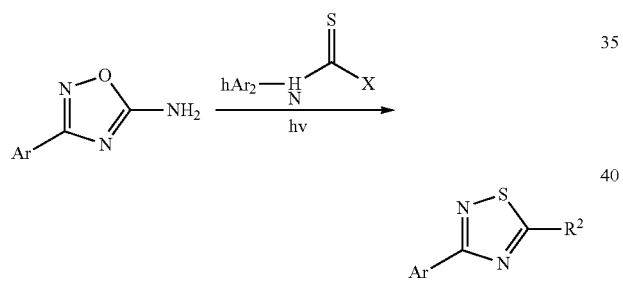

$X = NH_2, OMe$
$R^2 = NH—hAr^2$ for $X = NH_2$
$R^2 = O—hAr^2$ for $X = OMe$

Scheme 3B-Method of Preparing 2,5-disubstituted-1,3,4-thiadiazoles

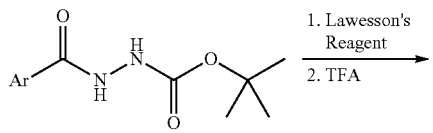

As shown in scheme 3B 1,3,4-thiadiazoles can be prepared by reacting BOC protected hydrazides with Lawesson's Reagent in the presence of trifluoroacetic acid, to form thiohydrazides, which react with substituted aldehydes by spontaneous cyclization. (See B. G. Szczepankiewicz et al., J. Med. Chem. 2001, 44, 4416-4430).

Scheme 4A-Making Compounds of Formula (I) Comprising Aminopyridine, Pyrimidine and Pyrazine $hAr^1$ Rings:

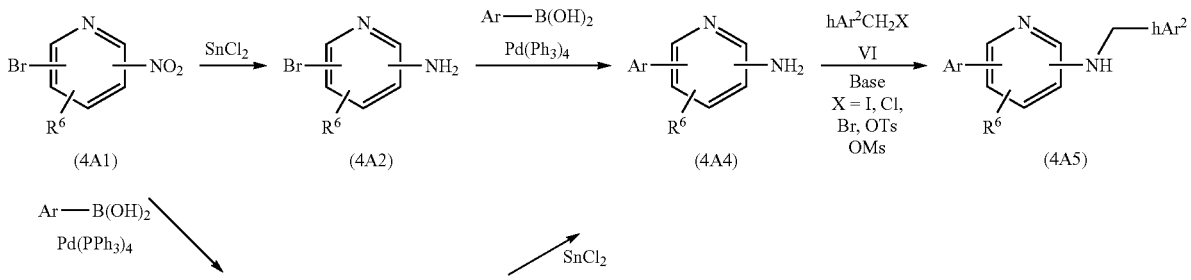

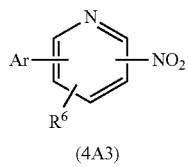

(4A3)

Many substituted and unsubstituted bromo-nitro pyridines, such as compound (4A1) in Scheme 4A, are commercially available, or are readily synthesized by methods well known to those of ordinary skill in the art. Reduction of the nitro groups of compounds (4A1) by various methods, including treatment with $SnCl_2$, can provide the aminopyridines (4A2). Alternatively, many amino pyridines (4A2) are also commercially available.

Bromopyridines such as (4A2), or (similar pyridines comprising triflate substituents) can be used for palladium catalyzed Suzuki coupling with arylboronic acid precursors of the Ar ring of the compounds of Formula (I), to afford the coupled-aromatic pyridine (4A4). The preparation of the required aryl boronic acids and procedures for Suzuki Coupling are well known in the art, and are disclosed for example by Suzuki, *Pure & Applied Chem.*, 66:213-222 (1994), Miyaura and Suzuki, *Chem. Rev.* 95:2457-2483 (1995), Watanabe, Miyaura and Suzuki, *Synlett.* 207-210 (1992), Littke and Fu, *Angew. Chem. Int. Ed.*, 37:3387-3388 (1998), Indolese, *Tetrahedron Letters*, 38:3513-3516 (1997), Firooznia, et al., *Tetrahedron Letters* 40:213-216 (1999), and Darses, et al., *Bull. Soc. Chim. Fr.* 133:1095-1102 (1996); all incorporated herein by reference.

The coupled-aromatic pyridine (4A4) can be treated with a base and an alkylating agent such as for example VI to provide the electrophillic pyridine derivative precursor of $hAr^2$, to yield compounds of Formula (I).

Alternatively, the amino intermediate (4A4) can be prepared by first Suzuki coupling of the bromo-nitro-pyridine (4A1) with an Aryl boronic acid, and then reduction of the nitro group, to provide the amine compound (4A3). An analogous series of reactions wherein the $NH_2$ group of compound (4A2) is replaced by a hydroxyl or sulfhydril group, or a protected derivative thereof, then subjected to Suzuki coupling and alkylation, and optional oxidation of the sulfur analogs with organic peracids, provides a ready synthetic route to compounds of Formula (I) wherein X is O, S, SO, or $SO_2$.

Similarly, synthesis of pyrimidine and pyrazine derivatives starting from commercially available bromo amino pyrimidines or pyridines can be accomplished analogously to the reactions described above, or in accordance with Scheme 4B as shown below:

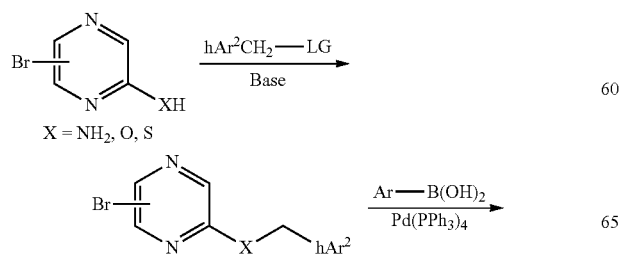

Scheme 4B

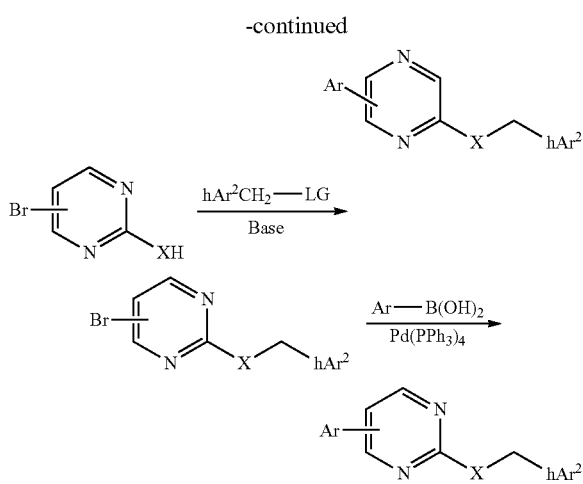

Bromo pyrimidine or pyrazine starting materials that are readily available can be alkylated by electrophillic precursors of $hAr^2$ and a base to provide synthetic intermediates with linked $hAr^1$ and $hAr^2$ radicals, which in turn can undergo Suzuki coupling with an arylboronic acid precursor of Ar to provide the desired pyrimidine and pyrazine compounds of Formula (I).

Scheme 5-Method of Preparing 3-(arylthio)-Optionally Substituted Pyridazines

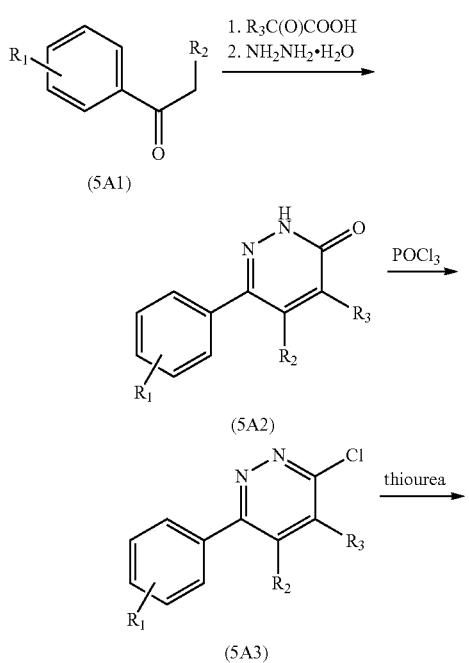

Scheme 6—Method of Preparing 3-(aryloxy) or 3 (arylamino)-Optionally Substituted Pyridazines

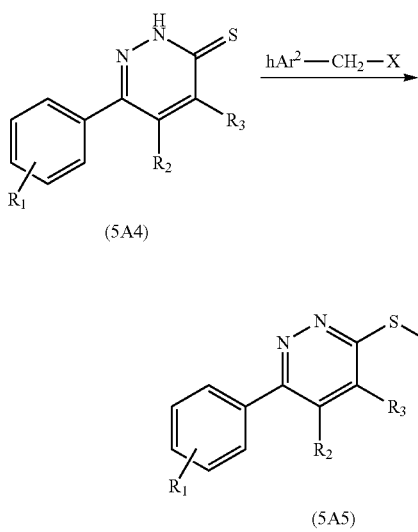

(5A4)

(5A5)

As shown in Scheme 5,3-(arylthio)-pyridazines (5A5) can be prepared in several steps by condensing desirably substituted acetophenone precursors of the Ar group (5A1) with α-ketoacids to give an acyclic keto-acid intermediate, which is then condensed with hydrazine to yield a cyclization product (5A2), that is precursor to hAr[1]. (5A2) can be treated with POCl$_3$ to yield the cyclic monochloride intermediate (5A3), which can react with thiourea to providing cyclic thiones of Formula (5A4), which are then alkylating agent precursors of hAr2, such as halides, tosylates, and the like, giving the desired 3-(arylthio)-pyridazines (5A5). See *J. Med. Chem.* 2001, 44, 2707-2718 (J.-M. Contreras); and *Molecules*, 2003, 8, 322-332 (G. H. Sayed).

Scheme 6A: Preparation of optionally substituted pyridazines:

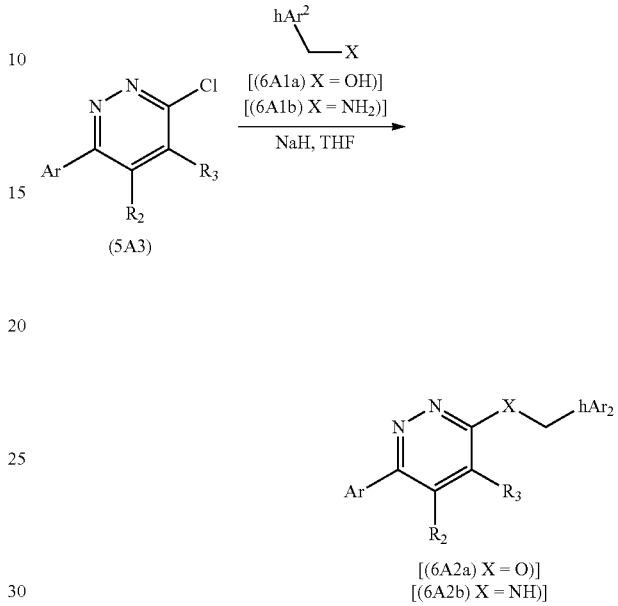

As shown in scheme 6A, chloropyridazine (5A3) (see scheme 5) can be converted to the optionally substituted (6A2a) or (6A2b) by reacting with the corresponding primary alcohol (6A1a) or amine (6A1b), see *J. Med. Chem.* 2001, 44, 2707-2718 (J.-M. Contreras);

Scheme 6B: Preparation of unsubstituted pyridazines:

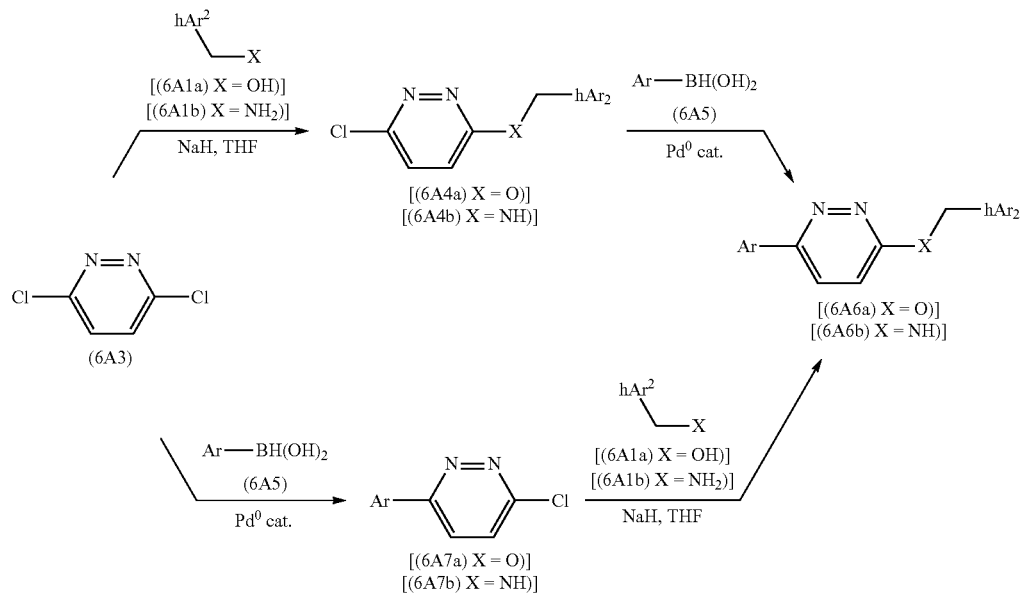

As shown in scheme 6B, unsubstituted pyridazines (6A6a) and (6A6b) can be prepared starting from the symmetrical dichloropyridazine (6A3) by treatment with the corresponding alcohol (6A1a) or amine (6A1b) followed by Suzuki coupling in presence of the boronic acid (6A5). Alternatively unsubstituted pyridazines (6A6a) and (6A6b) can be first coupled to the boronic acid (6A5) to provide the chloropyridazines (6A7a) and (6A7b) that can be treated with the alcohol (6A1a) or amine (6A1b) to provide the corresponding pyridazines (6A6a) and (6A6b).

Scheme 7-Method of Preparing 1,4-disubstituted-1,2,3-triazoles

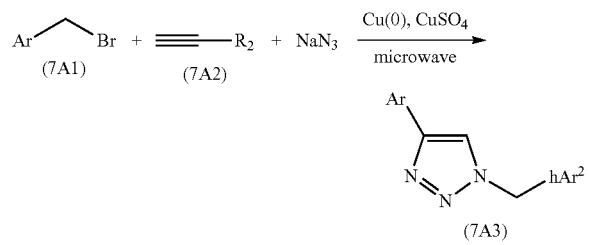

As shown in scheme 7, 1,4-disubstituted-1,2,3-triazoles (7A3) can be prepared using a microwave assisted three-component reaction from alkyl halide (7A1), sodium azide and alkyne (7A2), see P. Appukkuttan et al Org. Lett. 2004, 6, 23, 4223-4225.

Scheme 8-Method of Preparing 2,5-disubstituted-2H-tetrazoles

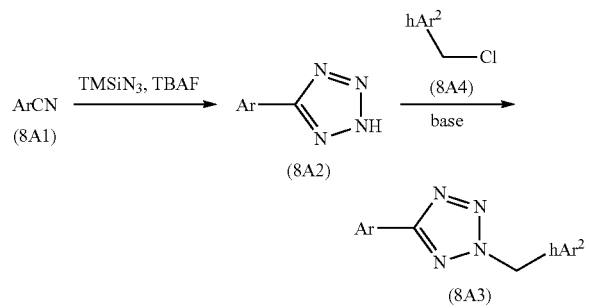

As shown in scheme 8, 2,5-disubstituted-2H-tetrazole (8A3) can be prepared from the nitrile (8A1) by reacting with trimethylsilyl azide (TMSiN$_3$) and tetrabutylammonium bromide (TBAF) See D. Amantini J. Org. Chem. 2004, 69,8, 2896-2898), providing the tetrazole intermediate (8A2) that can be alkylated with the alkyl halides (8A4), see J. R. Maxwell, J. Med. Chem. 1984, 27, 1565-1570.

The foregoing example schemes and cited prior art are provided for the guidance of the reader, and represent exemplary methods for making the compounds of Formula (I) disclosed herein. The prior art articles and patents cited in the example schemes are hereby incorporated by reference for the purpose of describing the relevant synthetic strategies and experimental methods. The methods cited above are not limiting, and it will be apparent to one of ordinary skill in the art that other synthetic strategies and/or modifications of the schemes disclosed above can be employed to prepare compounds of Formula (I). Such methods specifically include solid phase based chemistries, including combinatorial chemistry. The skilled artisan is therefore thoroughly equipped to prepare the necessary and/or claimed compounds by the methods given the cited treatises and literature, and this disclosure. The skilled artisan given the literature and this disclosure is well equipped to prepare any of the necessary starting materials and/or claimed compounds. Nevertheless, in some of the Examples cited below, starting materials were not readily available, and therefore were synthesized, and the synthesis of the starting materials is therefore exemplified.

Measuring the Biological Activity of the Compounds of the Invention

Cell based technologies and assays, such as those disclosed in WO 02/064631, and WO 03/001876, and U.S. Patent Publication US 2003-0232407 A1 were used both to initially screen a wide variety of classes of compounds for agonist or antagonist activity for T1R1/T1R3 "savory" taste receptors, that had been expressed in appropriate cell lines. Once initial "hits" were obtained for compounds screened with such cell lines, the same assays and also certain cell and/or receptor-based assays were used as analytical tools to measure the quantitative ability of the compounds of Formula (I) to enhance the savory taste of MSG, and were used to provide empirical data to guide an iterative process of synthesizing and testing structural variants of the initial compounds, in combination with occasional human testing of high interest species compounds, so as to design, test, and identify genuses of compounds and species therein having increased and optimized levels of the desired biological activities.

Many embodiments of the inventions relate to the identification of specific compounds and classes of the amide compounds of Formula (I) that modulate (increase or decrease) the activity of the T1R1/T1R3 (preferably hT1R1/hT1R3) savory taste receptor (umami receptor), alone or in combination with another compound that activates hT1R1/hT1R3, especially MSG. Particularly, many embodiments the invention relate to the linked heteroaryl compounds of Formula (I) that modulate the activity of hT1R1/hT1R3 (human umami receptor) in vitro and/or in vivo. In another aspect, the invention relates to compounds of Formula (I) that modulate the human perception of savory (umami) taste, alone or in combination with another compound or flavorant, such as MSG, when (1) one or more of the compounds of Formula (I) and (2) MSG are added to a comestible composition, with the result that the savory flavor of the MSG is enhanced or multiplied, so that it is necessary to add less MSG to the modified comestible compositions in order to produce the desired level of Umami/savory flavor.

In Vitro hT1R1/hT1R3 Umami Taste Receptor Activation Assay

In order to identify new savory flavoring agents and enhancers, including compounds with savory agonist and enhancer activities (dual activity), the compounds of Formula (I) were screened in primary assays and secondary assays including compound dose response and enhancement assay. In a primary assay for potential ability to modulate umami taste, compounds of Formula (I) that can be either savory flavoring agents in their own right or flavor enhancers of MSG are identified and scores of their activities are given as percentage of the maximum MSG intensity (%). In compound dose response, an EC$_{50}$ is calculated to reflect the potency of the compound as a savory agonist or enhancer.

An HEK293 cell line derivative (See e.g., Chandrashekar, et al., Cell (2000) 100: 703-711) which stably expresses Gα15 and hT1R1/hT1R3 under an inducible promoter (See WO 03/001876 A2) was used to identify compounds with savory tasting properties.

Compounds covered in this document were initially selected based on their activity on the hT1R1/hT1R3-HEK293-Gα15 cell line. Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated clone 1-17) were seeded into 384-well plates (at approximately 48,000 cells per well) in a medium containing Dulbecco's modified Eagle's medium (DMEM) supplemented with GlutaMAX (Invitrogen, Carlsbad, Calif.), 10% dialyzed fetal bovine serum (Invitrogen, Carlsbad, Calif.), 100 Units/ml Penicillin G, 100 µg/ml Streptomycin (Invitrogen, Carlsbad, Calif.), and 60 pM mifepristone (to induce expression of hT1R1/hT1R3, (See WO 03/001876 A2). I-17 cells were grown for 48 hours at 37° C. I-17 cells were then loaded with the calcium dye Fluo-3AM (Molecular Probes, Eugene, Oreg.), 4 µM in a phosphate buffered saline (D-PBS) (Invitrogen, Carlsbad, Calif.), for 1.5 hours at room temperature. After replacement with 25 µl D-PBS, stimulation was performed in the FLIPR instrument and at room temperature by the addition of 25 µl D-PBS supplemented with different stimuli at concentrations corresponding to twice the desired final level. Receptor activity was quantified by determining the maximal fluorescence increases (using a 480 nm excitation and 535 nm emission) after normalization to basal fluorescence intensity measured before stimulation.

For dose-responses analysis, stimuli were presented in duplicates at 10 different concentrations ranging from 1.5 nM to 30 µM. Activities were normalized to the response obtained with 60 mM monosodium glutamate, a concentration that elicits maximum receptor response. $EC_{50}$s (concentration of compound that causes 50% activation of receptor) were determined using a non-linear regression algorithm, where the Hill slope, bottom asymptotes and top asymptotes were allow to vary. Identical results were obtained when analyzing the dose-response data using commercially available software for non-linear regression analysis such as GraphPad PRISM (San Diego, Calif.).

In order to determine the dependency of hT1R1/hT1R3 for the cell response to different stimuli, selected compounds were subjected to a similar analysis on I-17 cells that had not been induced for receptor expression with mifepristone (designated as un-induced I-17 cells). The un-induced I-17 cells do not show any functional response in the FLIPR assay to monosodium glutamate or other savory-tasting substances. Compounds were presented to un-induced umami cells at 10 µM—or three times the maximum stimulation used in the dose-response analysis. Compounds covered in this document do not show any functional response when using un-induced umami cells in the FLIPR assay.

In some aspects of the present invention, an $EC_{50}$ of lower than about 10 mM is indicative of compounds that induce T1R1/T1R3 activity and is considered a savory agonist. Preferably a savory agonist will have $EC_{50}$ values of less than about 1 mM; and more preferably will have $EC_{50}$ values of less than about 20 µM, 15 µM, 10 µM, 5 µM, 3 µM, 2 µM, 1 µM, 0.8 µM or 0.5 µM.

In umami taste enhancement activity assay experiments, also produce an "$EC_{50}$ ratio" measurement of how effectively the amide compounds of the invention enhance the savory flavorant (typically MSG) already in a test solution. A series of measurements of the dose response is run in solutions comprising MSG alone, then a second dose response is run with MSG in combination with predetermined amounts of a candidate compound of Formula (I) at the same time.

In this assay, increasing concentrations of monosodium glutamate (ranging from 12 µM to 81 mM) were presented, in duplicates, in the presence or absence of a fixed concentration of the test compound. Typical compound concentrations tested were 30 µM, 10 µM, 3 µM, 1 µM, 0.3 µM, 0.1 µM and 0.03 µM. The relative efficacy of compounds of Formula (I) at enhancing the receptor was determined by calculating the magnitude of a shift in the $EC_{50}$ for monosodium glutamate. Enhancement was defined as a ratio ($EC_{50}R$) corresponding to the $EC_{50}$ of monosodium glutamate, determined in the absence of the test compound, divided by the $EC_{50}$ of monosodium glutamate, determined in the presence of the test compound. Compounds exhibiting $EC_{50}R>2.0$ were considered enhancers.

Stated alternatively, "$EC_{50}$ ratio" as compared to MSG is calculated based on the following definitions:

$$EC_{50} \text{ Ratio vs. MSG} = EC_{50}(\text{MSG})/EC_{50}(\text{MSG}+[\text{Compound}])$$

wherein "[compound]" refers to the concentration of the compound of Formula (I) used to elicit (or enhance or potentiate) the MSG dose response.

It should be noted that the $EC_{50}$ ratio measured can depend somewhat on the concentration of the compound itself. Preferred savory enhancers would have a high $EC_{50}$ Ratio vs. MSG at a low concentration of the compound used. Preferably the $EC_{50}$ ratio experiments to measure umami enhancement are run at a concentration of a compound of Formula (I) between about 10 µM to about 0.1 µM, or preferably at 1.0 µM or 3.0 µM.

An $EC_{50}$ ratio of greater than 1 is indicative of a compound that modulates (potentiates) hT1R1/hT1R3 activity and is a savory enhancer. More preferably, the savory taste enhancer compounds of Formula (I) will have $EC_{50}$ ratio values of at least 1.2, 1.5, 2.0, 3.0, 4.0, 5.0, 8.0, or 10.0, or even higher.

In one aspect, the extent of savory modulation of a particular compound is assessed based on its effect on MSG activation of T1R1/T1R3 in vitro. It is anticipated that similar assays can be designed using other compounds known to activate the T1R1/T1R3 receptor.

Specific compounds and generic classes of compounds that been shown to modulate hT1R1/hT1R3 based on their $EC_{50}$ ratios evaluated according to the above formula are identified in the detailed description of the invention, the examples, and the claims.

The procedures used for human taste testing of the umami/savory compounds of Formula (I) are reported hereinbelow. Comparable $EC_{50}$ assays for activity of the compounds of Formula (I) for sweet receptor agonism and/or sweet taste perception in humans are also reported hereinbelow.

EXAMPLES

The following examples are given to illustrate a variety of exemplary embodiments of the invention and are not intended to be limiting in any manner.

For the purpose of this document, the compounds individually disclosed in the following Examples 1-12 and corresponding Tables A and B can be referred in shorthand by the number of the example. For example, as shown immediately bellow, Example 1 discloses a synthesis of a particular compound 2-((5-(2-methoxy-4-methylphenyl)-1H-1,2,4-triazol-3-ylthio)methyl)pyridine, and the results of experimental assays of its biological effectiveness, which compound is and can be referred to herein in shorthand form as Compound 1. Similarly, the first compound illustrated in Table A can be referred to elsewhere herein as Compound A1.

Example 1

2-((5-(2-methoxy-4-methylphenyl)-1H-1,2,4-triazol-3-ylthio)methyl)pyridine

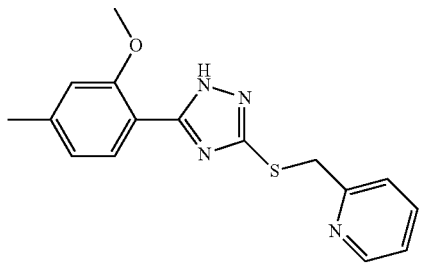 [SMILES: COc1cc(C)ccc1-c1nc(SCc2ccccn2)n[nH]1]

To a solution of 5-(2-methoxy-4-methylphenyl)-2H-1,2,4-triazole-3(4H)-thione (Example 1a) (110 mg, 0.5 mmol) in 2 ml of EtOH was added 2-(bromomethyl)pyridine hydrobromide (152 mg, 0.6 mmol). The suspension was heated at 60° C. for 22 h. The reaction was diluted with EtOAc and washed with water, brine, dried over MgSO$_4$ filtered and evaporated to produce an oil. The oil was purified on a preparative TLC plate to produce the desired product (72%). $^1$H NMR (500 MHz, CDCl$_3$): δ 2.40 (s, 3H), 3.99 (s, 3H), 4.55 (s, 2H), 6.84 (s, 1H), 6.92-6.93 (d, 1H), 7.16-7.19 (dd, 1H), 7.53-7.55 (d, 1H), 7.62-7.65 (m, 1H), 8.15-8.17 (d, 1H), 8.56-8.57 (d, 1H). MS (M+H, 313).

The compound had EC$_{50}$ for activation of a hT1R1/hT1R3 umami receptor expressed in an HEK293 cell line of 0.08 μM, and when present at 0.03 μM enhanced the effectiveness of monosodium glutamate with an EC$_{50}$ ratio of 5.9.

Example 1a 5-(2-methoxy-4-methylphenyl)-2H-1,2,4-triazole-3(4H)-thione

To a solution of 2-methoxy-4-methylbenzoic acid (1.81 g, 9.22 mmol) in 9 ml of pyridine was added EDCI (1.9 g, 9.3 mmol) and the suspension was stirred at r.t. for 1 h. Then thiosemicarbazide (800 mg, 8.8 mmol) was added and the reaction was stirred at r.t. for 21 h. The mixture was evaporated to dryness and then diluted with water. The white solid was then filtered, washed with water and suspended in 20 ml 1 M aq. NaHCO$_3$ and then heated at reflux for 2 days. The suspension was filtered hot and the aqueous solution was cooled in ice and acidified to pH 3 with conc. HCl. The solid was filtered and washed with water and dried to give a white powder (47%).

Example 2

2-((5-(2-methoxy-4-methylphenyl)-1H-1,2,4-triazol-3-ylthio)methyl)-5-methylpyridine

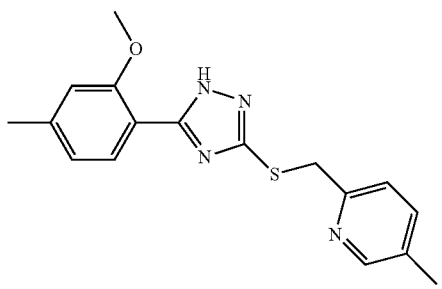

Prepared in a similar manner to example 1 using 5-(2-methoxy-4-methylphenyl)-2H-1,2,4-triazole-3(4H)-thione (example 1a) and 2-(chloromethyl)-5-methylpyridine (example 2a). Yield 14%. $^1$H NMR (500 MHz, CDCl$_3$): δ 2.29 (s, 3H), 2.41 (s, 3H), 4.00 (s, 3H), 4.51 (s, 2H), 6.75 (s, 1H), 6.90 (s, 1H), 7.40 (s, 1H), 8.1 (d, 1H), 8.4 (s, 1H), 11.5-11.7 (bs, 1H). MS (M+H, 327.1).

The compound had EC$_{50}$ for activation of a hT1R1/hT1R3 umami receptor expressed in an HEK293 cell line of 0.49 μM.

Example 2a 2-(chloromethyl)-5-methylpyridine 2,5-Dimethylpyridine (5.18 ml, 44.8 mmol) was mixed with DCM (100 mL) and cooled in an ice bath. MCPBA (15.5 g, 2 eq.) was then added in portions over 30 min. The solution was stirred at r.t. overnight. The reaction mixture was then washed with aq. NaHCO$_3$, brine, dried and evaporated to produce an N-oxide that was used without further purification. A solution of the N-oxide (2.22 g, 18 mmol), p-TsCl (5.15 g, 27 mmol) in DCM (3 mL) was heated at 40° C. under argon for 2 h. The solution was then added dropwise to a solution of triethylamine (3.8 mL, 27 mL) in DCM (18 mL) while heating at 40° C. under argon. The orange solution was heated at 40° C. for an additional 3 h. Then the mixture was cooled, neutralized with solid NaHCO$_3$ (2 g) and evaporated under vacuum. The crude material was dissolved in MeOH (24 mL) to give an estimated product in 0.75 M solution. The crude solution of 2-(chloromethyl)-5-methylpyridine was used in the next step without further purification.

Example 3

2-((5-(2,4-dimethylphenyl)-1H-1,2,4-triazol-3-ylthio)methyl)pyridine

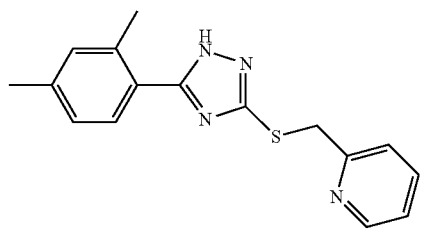 [SMILES: Cc1ccc(-c2nc(SCc3ccccn3)n[nH]2)c(C)c1]

Prepared in a similar manner to example 1 using 5-(2,4 dimethylphenyl)-2H-1,2,4-triazole-3(4H)-thione (example 3a) and 2-(bromomethyl)pyridine hydrobromide. Yield 64%. $^1$H NMR (500 MHz, CDCl$_3$): δ 2.34 (s, 3H), 2.57 (s, 3H), 4.37 (s, 2H), 4.51 (s, 2H), 7.04-7.08 (m, 2H), 7.28-7.31 (m, 1H), 7.41-7.43 (d, 1H), 7.74-7.77 (m, 2H), 8.63-8.64 (d, 1H). MS (M+H, 297); mp=112-114° C.

The compound had EC$_{50}$ for activation of a hT1R1/hT1R3 umami receptor expressed in an HEK293 cell line of 0.09 μM, and when present at 0.01 μM enhanced the effectiveness of monosodium glutamate with an EC$_{50}$ ratio of 4.3.

Example 3a 5-(2,4 dimethylphenyl)-2H-1,2,4-triazole-3(4H)-thione

A suspension of thiosemicarbazide (800 mg, 8.78 mmol) in 9 mL of pyridine was added 2,4-dimethylbenzoyl chloride (1.68 g, 10 mmol). The reaction was heated at 150° C. for 10 min using a microwave synthesizer. The yellow solution was evaporated to dryness and then diluted with water. The white solid was then collected and washed with water. The solid was suspended in 20 mL of 1 M aq. NaHCO₃. The suspension was heated at 180° C. for 1 h using a microwave synthesizer. Then the mixture was filtered hot and the aqueous solution was cooled in ice and acidified to pH 3 with conc. HCl. The solid was filtered and washed with water and dried to give white powder (43%).

Example 4

2-((5-(4-Ethylphenyl)-1H-1,2,4-triazol-3-ylthio)methyl)pyridine

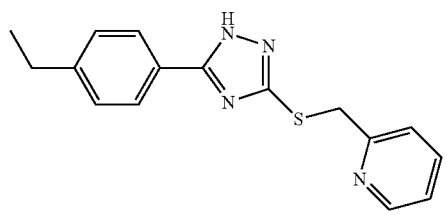 [SMILES: CCc1ccc(-c2nc(SCc3ccccn3)n[nH]2)cc1]

Prepared in a similar manner to example 1 using 5-(4-ethylphenyl)-2H-1,2,4-triazole-3(4H)-thione (example 4a) and 2-(bromomethyl)pyridine hydrobromide. Yield 71%. $^1$H NMR (500 MHz, dMSO): δ 1.18-1.22 (t, 3H), 2.64-2.66 (t, 2H), 4.52 (s, 2H), 7.30-7.88 (m, 8H), 14.3 (bs, 1H). MS (M+H, 297).

The compound had $EC_{50}$ for activation of a hT1R1/hT1R3 umami receptor expressed in an HEK293 cell line of 0.14 μM, and when present at 0.03 μM enhanced the effectiveness of monosodium glutamate with an $EC_{50}$ ratio of 4.4.

Example 4a 5-(4-Ethylphenyl)-2H-1,2,4-triazole-3(4H)-thione

Prepared in a similar manner to example 3a using 4-ethylbenzoyl chloride (yield 65%).

Example 5

2-((5-(4,5-dimethylfuran-2-yl)-1H-1,2,4-triazol-3-ylthio)methyl)pyridine

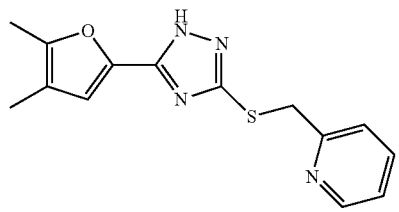 [SMILES: Cc1cc(-c2nc(SCc3ccccn3)n[nH]2)oc1C]

Prepared in a similar manner to example 1 using 5-(4,5-dimethylfuran-2-yl)-2H-1,2,4-triazole-3(4H)-thione (example 5a) and 2-(bromomethyl)pyridine hydrobromide. Yield 27%. $^1$H NMR (500 MHz, dMSO): δ 1.98 (s, 3H), 2.28 (s, 3H), 4.37 (s, 2H), 6.76 (s, 1H), 7.3 (m, 1H), 7.45 (d, 1H), 7.75 (t, 1H), 8.6 (s, 1H). MS (M+H, 287).

The compound had $EC_{50}$ for activation of a hT1R1/hT1R3 umami receptor expressed in an HEK293 cell line of 0.58 μM, and when present at 0.1 μM enhanced the effectiveness of monosodium glutamate with an $EC_{50}$ ratio of 4.4.

Example 5a 5-(4,5-dimethylfuran-2-yl)-2H-1,2,4-triazole-3(4H)-thione

Prepared in a similar manner to example 1a using 4,5-dimethylfuran-2-carboxylic acid (yield 25%).

Example 6

2-((5-(4,5-dimethylfuran-2-yl)-1H-1,2,4-triazol-3-ylthio)methyl)pyridine

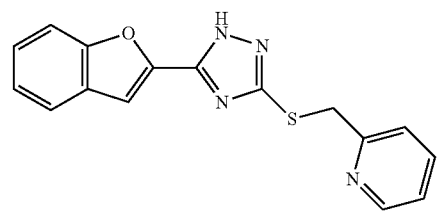 [SMILES: c1ccc(CSc2n[nH]c(-c3cc4ccccc4o3)n2)nc1]

Prepared in a similar manner to example 1 using 5-(benzofuran-2-yl)-2H-1,2,4-triazole-3(4H)-thione (example 6a) and 2-(bromomethyl)pyridine hydrobromide. Yield 59%. $^1$H NMR (500 MHz, CDCl₃): δ 4.37 (s, 2H), 7.26-7.34 (m, 5H), 7.4-7.42 (d, 1H), 7.55-7.57 (d, 1H), 7.65-7.67 (d, 1H), 7.75 (t, 1H), 8.62 (s, 1H). MS (M+H, 309).

The compound had $EC_{50}$ for activation of a hT1R1/hT1R3 umami receptor expressed in an HEK293 cell line of 2.58 μM, and when present at 0.1 μM enhanced the effectiveness of monosodium glutamate with an $EC_{50}$ ratio of 2.88.

Example 6a 5-(benzofuran-2-yl)-2H-1,2,4-triazole-3(4H)-thione

Prepared in a similar manner to example 3a using benzofuran-2-carbonyl chloride (yield 73%).

Example 7

2-((5-(2,5-dimethylfuran-3-yl)-1H-1,2,4-triazol-3-ylthio)methyl)pyridine

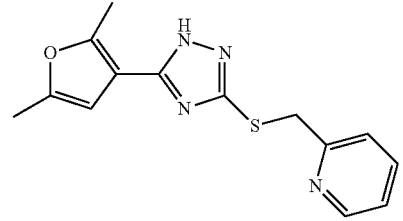 [SMILES: Cc1cc(-c2nc(SCc3ccccn3)n[nH]2)c(C)o1]

Prepared in a similar manner to example 1 using 5-(2,5-dimethylfuran-3-yl)-2H-1,2,4-triazole-3(4H)-thione (example 7a) and 2-(bromomethyl)pyridine hydrobromide. Yield 70%. $^1$H NMR (500 MHz, CDCl₃): δ 2.27 (s, 3H), 2.59 (s, 3H), 4.32 (s, 2H), 6.35 (s, 1H), 7.28-7.29 (d, 1H), 7.35-7.36 (d, 1H), 7.75 (t, 1H) 8.62 (s, 1H). MS (M+H, 287).

The compound had EC$_{50}$ for activation of a hT1R1/hT1R3 umami receptor expressed in an HEK293 cell line of 2.07 µM, and when present at 0.1 µM enhanced the effectiveness of monosodium glutamate with an EC$_{50}$ ratio of 2.1.

Example 7a 5-(2,5-dimethylfuran-3-yl)-2H-1,2,4-triazole-3(4H)-thione

Prepared in a similar manner to example 3a using 2,5-dimethylfuran-3-carbonyl chloride (yield 72%).

Example 8

2-(2-(5-(4,5-dimethylfuran-2-yl)-1H-1,2,4-triazol-3-ylthio)ethyl)pyridine

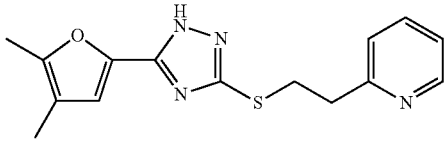 [SMILES: Cc1cc(-c2nc(SCCc3ccccn3)n[nH]2)oc1C]

Prepared in a similar manner to example 1 using 5-(4,5-dimethylfuran-2-yl)-2H-1,2,4-triazole-3(4H)-thione (example 5a) and 2-(2-bromoethyl)pyridinium bromide (example 8a). Yield 55%. $^1$H NMR (500 MHz, CDCl$_3$): δ 1.96 (s, 3H), 2.24 (s, 3H), 3.28 (t, 2H), 3.49 (t, 2H), 6.77 (s, 1H), 7.13-7.23 (m, 2H), 7.65 (t, 1H) 8.58 (s, 1H). MS (M+H, 301).

The compound had EC$_{50}$ for activation of a hT1R1/hT1R3 umami receptor expressed in an HEK293 cell line of 1.87 µM, and when present at 0.1 µM enhanced the effectiveness of monosodium glutamate with an EC$_{50}$ ratio of 2.66.

Example 8a 2-(2-bromoethyl)pyridinium bromide

To a solution of 2-(2-hydroxyethyl)pyridine (3 ml, 26.6 mmol) was added 30 ml of 33% HBr in acetic acid. The yellow solution was heated in the capped vial at 78° C. for 2 days. The reaction was evaporated under high vacuum to produce a brown solid. The solid was re-crystallized from hot isopropanol to produce a light tan solid (73%). $^1$H NMR (500 MHz, dMSO): δ 3.62-3.65 (t, 2H), 3.95-3.98 (t, 2H), 7.95 (t, 1H), 8.09-8.10 (d, 1H), 8.58 (t, 1H), 8.90 (d, 1H).

Example 9

2-((5-(2,4-dimethoxybenzyl)-1H-1,2,4-triazol-3-ylthio)methyl)pyridine

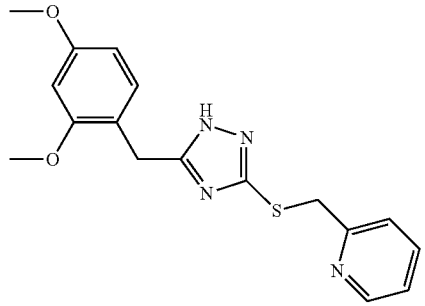 [SMILES: COc1ccc(Cc2nc(SCc3ccccn3)n[nH]2)c(OC)c1]

Prepared in a similar manner to example 1 using 5-(2,4-dimethoxybenzyl)-2H-1,2,4-triazole-3(4H)-thione (example 9a) and 2-(bromomethyl)pyridine hydrobromide. Yield 34%. $^1$H NMR (500 MHz, CDCl$_3$): δ 3.77 (s, 3H), 3.79 (s, 3H), 4.0 (s, 2H), 4.34 (s, 2H), 6.35-6.45 (m, 2H), 7.1 (d, 1H), 7.15 (t, 1H), 7.3 (d, 1H), 7.7 (t, 1H), 8.5 (s, 1H). MS (M+H, 343).

The compound had EC$_{50}$ for activation of a hT1R1/hT1R3 umami receptor expressed in an HEK293 cell line of 1.2 µM, and when present at 0.1 µM enhanced the effectiveness of monosodium glutamate with an EC$_{50}$ ratio of 2.66.

Example 9a 5-(2,4-dimethoxybenzyl)-2H-1,2,4-triazole-3(4H)-thione

Prepared in a similar manner to example 1a using 2,4-dimethoxyphenyl acetic acid. $^1$H NMR (500 MHz, CDCl$_3$): δ 3.80 (s, 3H), 3.90 (s, 3H), 6.4-6.5 (m, 2H), 7.1 (bs, 1H), 9.8 (bs, 1H), 10.2 (bs, 1H).

Example 10

2-((5-(4-Ethyl-2-methylphenyl)-1H-1,2,4-triazol-3-ylthio)methyl)pyridine

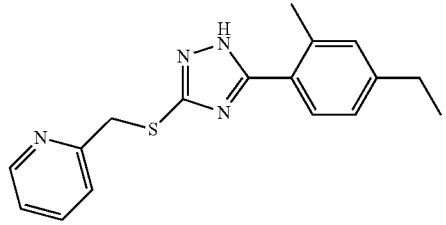 [SMILES: CCc1ccc(-c2nc(SCc3ccccn3)n[nH]2)c(C)c1]

Prepared in a similar manner to example 1 using 5-(4-ethyl-2-methylphenyl)-2H-1,2,4-triazole-3(4H)-thione (example 10a) and 2-(bromomethyl)pyridine hydrobromide. Yield 39%. $^1$H NMR (300 MHz, dMSO): δ 1.17-1.22 (t, 3H), 2.46 (s, 3H), 2.60-2.64 (dd, 2H), 4.50 (s, 2H), 7.14-7.18 (m, 2H), 7.27-7.29 (m, 1H), 7.47-7.49 (d, 1H), 7.58 (bd, 1H), 7.72-7.77 (m, 1H), 8.50-8.51 (d, 1H). MS (M+H, 311).

The compound had EC$_{50}$ for activation of a hT1R1/hT1R3 umami receptor expressed in an HEK293 cell line of 0.02 µM.

Example 10a 5-(4-Ethyl-2-methylphenyl)-2H-1,2,4-triazole-3(4H)-thione

Prepared in a similar manner to example 1a using 4-ethyl-2-methylbenzoic acid (example 10b). Yield 59%. MS (M+H, 220).

Example 10b

4-Ethyl-2-methylbenzoic acid

Methyl 4-ethyl-2-methylbenzoate (example 10c) (2.37 g) was dissolved in aq. NaOH (1M, 40 mL) and the solution heated at 60° C. overnight. The mixture was washed with hexanes and the aqueous layer was acidified with 6N HCl to pH 2. The title product was obtained as a white precipitate, following filtration and drying (2.17 g, 80%).

Example 10c

Methyl 4-ethyl-2-methylbenzoate

4-Chloro-2-methylbenzoic acid (3 g, 17.6 mmol) was suspended in 12 ml of MeOH with 1 ml of concentrated H$_2$SO$_4$.

The mixture was refluxed overnight, MeOH was evaporated and the residue was extracted with EtOAc, dried over MgSO$_4$ filtered and evaporated to give methyl 4-chloro-2-methylbenzoate as a colorless viscous liquid (2.96 g, 92%) that was used in the next step without further purification. The ester (2.96 g, 16 mmol) was, under inert atmosphere, dissolved in THF (100 mL) and NMP (9 mL) and Iron(III) acetylacetonate (318 mg, 0.9 mmol) was added giving a red solution. Then EtMgBr (7 ml of 1M solution in ether) was added dropwise under vigorous stirring. The mixture turned dark brown and then violet and then was stirred for 15 more min. The reaction was diluted with ether and quenched upon the addition of aq. HCl (1M, 10 ml). The crude product was extracted with ether. The combined organic layers were washed with water and brine, dried over MgSO$_4$ and evaporated. The residue was purified on silica gel (30% EtOAc/hexanes) to give methyl 4-ethyl-2-methylbenzoate as an oil (2.37 g, 83%). ($^1$H NMR (500 MHz, CDCl$_3$): δ 1.26 (t, 3H), 2.63 (dd, 2H), 3.9 (s, 3H), 7.1 (b, 2H), 7.85 (d, 1H)).

Example 11

2-((4-p-Tolyl-1H-1,2,3-triazol-1-yl)methyl)pyridine

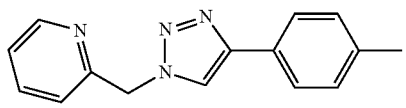 [SMILES: Cc1ccc(-c2cn(Cc3ccccn3)nn2)cc1]

A mixture of tBuOH (1.5 mL), water (1.5 mL), 2-(bromomethyl)pyridine (253 mg, 1 mmol), 1-ethynyl-4-methylbenzene (122 mg, 1.05 mmol) and NaN$_3$ (68 mg, 1.05 mmol) was added to a microwaveable vial. A cooper wire (50 mg) and CuSO$_4$ (200 μl of 1M aq. solution) was added to the stirred suspension. The vial was sealed and the mixture was irradiated (Microwave, Personnal Chemistry, Biotage from Upsala sweeden) at 125° C. for 5 min. The mixture was then diluted with water and the product was extracted to EtOAc, washed with 1M ammonium citrate, 0.25 M aq. HCl and brine, dried over MgSO$_4$, filtered and evaporated. The crude product was purified on silica gel (Eluent: 10% MeOH in DCM) to give 2-((4-p-Tolyl-1H-1,2,3-triazol-1-yl) methyl) pyridine (88 mg, 35%). $^1$H NMR (300 MHz, dMSO): δ 2.30 (s, 3H), 5.72 (s, 2H), 7.30-7.45 (m, 4H), 7.77-7.89 (m, 3H), 8.60 (s, 1H); MS (M+H, 251).

The compound had EC$_{50}$ for activation of umami receptor expressed in an HEK293 cell line of 4.66 μM.

Example 12

2-(2-(4-p-Tolyl-1H-1,2,3-triazol-1-yl)ethyl)pyridine

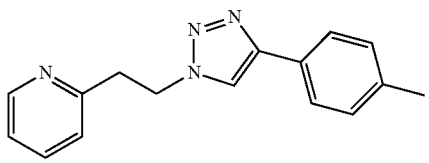 [SMILES: Cc1ccc(-c2cn(CCc3ccccn3)nn2)cc1]

Prepared in a similar manner to example 11 using 2-(2-bromoethyl)pyridine hydrobromide. Yield 74 mg, 28%. $^1$H NMR (300 MHz, dMSO): δ 2.30 (s, 3H), 3.99 (s, 3H), 3.36- 3.38 (m, 2H), 4.76-4.79 (m, 2H), 7.21-7.23 (m, 4H), 7.65-7.67 (m, 3H), 7.53-7.55 (d, 1H), 8.46 (s, 1H); MS (M+H, 265).

The compound had EC$_{50}$ for activation of umami receptor expressed in an HEK293 cell line of 16.35 μM.

Example 13

3-(2,4-Dimethylphenyl)-6-(pyridin-2-ylmethylthio) pyridazine

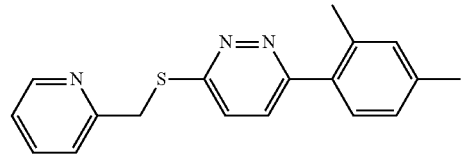

To a mixture of 2-(bromomethyl)pyridine hydrobromide (116 mg; 0.46 mmol) and 6-(2,4-dimethylphenyl)pyridazine-3(2H)-thione (Example 13a) (100 mg, 0.46 mmol) in EtOH (3 mL) was added EtONa (20% in EtOH, 25 μl) and the reaction was irradiated in a microwave at 140° C. for 4 min. The crude mixture was dried down and purified on silica gel (Eluent: 5% MeOH in DCM) to give 3-(2,4-Dimethylphenyl)-6-(pyridin-2-ylmethylthio)pyridazine (49 mg, 35%) as a white solid solid. $^1$H NMR (300 MHz, dMSO: δ 2.49 (s, 3H), 2.54 (s, 3H), 4.09 (s, 2H), 6.32-6.37 (m, 2H), 6.45-6.52 (m, 2H), 6.75-6.78 (d, 1H), 6.84-6.87 (m, 2H), 6.95-6.98 (t, 1H), 7.67-7.68 (d, 1H); MS (M+H, 308).

The compound had EC$_{50}$ for activation of umami receptor expressed in an HEK293 cell line of 1.5 μM.

Example 13a 6-(2,4-Dimethylphenyl)pyridazine-3(2H)-thione 3-chloro-6-(2,4-dimethylphenyl)pyridazine (example 13b) (1.36 g) was refluxed with thiourea (473 mg, 6.2 mmol) in EtOH (25 mL) for 5 hrs. The mixture was evaporated, and water (45 mL) was added to the residue, followed by Na$_2$CO$_3$ (318 mg, 3 mmol). The precipitate that formed was collected by filtration, washed with diethylether and dried to give 6-(2, 4-Dimethylphenyl)pyridazine-3(2H)-thione (1.12 g, 52%). $^1$H NMR (300 MHz, dMSO): δ 2.29 (s, 3H), 2.32 (s, 3H), 7.12-7.30 (m, 2H), 7.29-7.31 (d, 1H), 7.46-7.49 (d, 1H), 7.65-7.68 (dd, 1H); MS (M+H, 217).

Example 13b 3-chloro-6-(2,4-dimethylphenyl)pyridazine 6-(2,4-dimethylphenyl)pyridazin-3(2H)-one (example 13c) was heated with POCl$_3$ (5.15 ml, 55 mmol) at 85° C. for 4 hours. Following cooling and treating with crushed ice a white solid obtained and was collected to give 1.36 g of the 3-chloro-6-(2,4-dimethylphenyl)pyridazine. $^1$H NMR (300 MHz, dMSO): δ 2.29 (s, 3H), 2.34 (s, 3H), 7.16-7.19 (m, 2H), 7.35-7.37 (d, 1H), 7.93-8.00 (dd, 2H); (M+H, 313).

Example 13c 6-(2,4-dimethylphenyl)pyridazin-3(2H)-one

A mixture of glyoxylic acid monohydrate (920 mg, 10 mmol) and 2',4'-dimethylacetophenone (4.45 mL, 30 mmol)

was stirred at 150° C. for 2 hr. Then the mixture was cooled down to room temperature and water (4 mL) was added followed by conc. aq. NH$_4$OH (1 mL). The mixture was washed with DCM. To the ammoniac solution was added hydrazine (314 µL, 10 mmol) and the solution was refluxed for 3 hours. After cooling to room temperature the precipitate was collected by filtration to give the desired product as a white powder (1.1 g, 55%), $^1$H NMR (300 MHz, dMSO): δ 2.22 (s, 3H), 2.25 (s, 3H), 6.93-6.95 (d, 1H), 7.15 (m, 3H), 7.21-7.23 (d, 1H), 7.57-7.61 (d, 1H), 13.1 (bs, 1H); (M+H, 201).

Example 14

3-(Benzylthio)-6-(2,4-dimethylphenyl)pyridazine

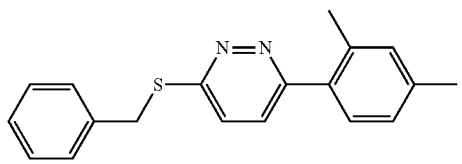

Prepared in a similar manner to example 13 using benzyl bromide and 6-(2,4-dimethylphenyl)pyridazine-3(2H)-thione (Example 13a). Yield 53.5 mg (38%). $^1$H NMR (300 MHz, dMSO): δ 2.29 (s, 3H), 2.34 (s, 3H), 4.60 (s, 2H), 7.16-7.17 (m, 2H), 7.30-7.34 (m, 4H), 7.47-7.49 (d, 2H), 7.64-7.72 (m, 2H); MS (M+H, 307).

The compound had EC$_{50}$ for activation of umami receptor expressed in an HEK293 cell line of 2.7 µM.

Example 15

3-(2,4-Dimethylphenyl)-6-(pyridin-2-ylmethoxy) pyridazine

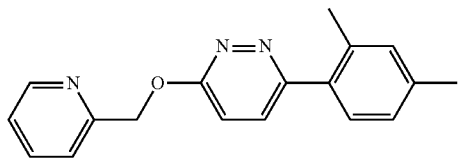 [SMILES: Cc1ccc(-c2ccc(OCc3ccccn3)nn2)c(C)c1]

3-Chloro-6-(pyridin-2-ylmethoxy)pyridazine (Example 15a) (221 mg, 1 mmol) was dissolved in toluene (10 mL), EtOH (2 mL), and water (1.5 mL). Then 2,4-dimethylphenylboronic acid (150 mg, 1 mmol) was added, followed by K$_2$CO$_3$ (276 mg, 2 mmol) and the mixture was degassed using argon stream. Tetrakis(triphenylphosphine)palladium (232 mg, 0.2 mmol) was added under argon and the mixture was refluxed overnight. The solvents were removed under vacuum and a residual solid was extracted with EtOAc, and successively washed with water and brine dried over MgSO$_4$ filtered and evaporated. The crude material was purified on silica gel (Eluent: 50% EtOAc in hexanes) to give 3-(2,4-Dimethylphenyl)-6-(pyridin-2-ylmethoxy)pyridazine (169 mg, 58%) as a white solid. $^1$H NMR (300 MHz, dMSO): δ 2.26 (s, 3H), 2.32 (s, 3H), 5.62 (s, 2H), 7.13-7.15 (m, 2H), 7.28-7.40 (m, 2H), 7.55-7.56 (d, 1H), 7.78-7.84 (m, 2H), 8.58-8.60 (d, 1H); MS (M+H, 292).

The compound had EC$_{50}$ for activation of umami receptor expressed in an HEK293 cell line of 6.9 µM.

Example 15a

3-Chloro-6-(pyridin-2-ylmethoxy)pyridazine

To a solution of NaH (1.44 g, 36 mmol, 60% in mineral oil) in THF (15 mL) was added pyridin-2-ylmethanol (1.16 ml, 12 mmol) and the mixture was stirred for 30 min at rt. Then 3,6-dichloropyridazine (1.79 g, 14 mmol) was added and the mixture was stirred at 55° C. for 4 hours. The reaction was quenched with water and sat. NaHCO$_3$ was added. The product was then extracted with EtOAc, dried over MgSO$_4$ filtered and evaporated. The residue was purified on silica gel (Eluent: 80% EtOAc in hexanes) to give 3-chloro-6-(pyridin-2-ylmethoxy)pyridazine as a white solid (1.64 g, 62%). $^1$H NMR (300 MHz, dMSO): δ 5.57 (s, 2H), 7.35-7.38 (m, 1H), 7.48-7.54 (m, 2H), 7.82-7.88 (m, 2H), 8.57-8.59 (dd, 1H); MS (M+H, 222).

Example 16

5-(2,4-Dimethylphenyl)-N-(pyridin-2-ylmethyl)-1,3,4-oxadiazol-2-amine

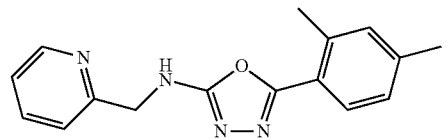 [SMILES: Cc1ccc(-c2nnc(NCc3ccccn3)o2)c(C)c1]

To a solution of 5-(2,4-dimethylphenyl)-1,3,4-oxadiazol-2-amine (Example 16a) (94.5 mg, 0.5 mmol) in 5 ml of dry acetonitrile was added K$_2$CO$_3$ (207 mg, 1.5 mmol). To the suspension was added 2-(bromomethyl)pyridine hydrobromide (127 mg, 0.5 mmol) and the mixture was stirred at 90° C. overnight. The solvent was removed under vacuum and the solid was dissolved in EtOAc, washed successively with aq. NaHCO$_3$ and brine, dried over MgSO$_4$ filtered and evaporated. The residue was purified on silica gel to give 5-(2,4-Dimethylphenyl)-N-(pyridin-2-ylmethyl)-1,3,4-oxadiazol-2-amine (136 mg, 97%) as a white solid. $^1$H NMR (300 MHz, CdCl$_3$): δ 2.34 (s, 3H), 2.5 (s, 3H), 5.1 (s, 2H), 7.07-7.08 (m, 2H), 7.21-7.33 (m, 2H), 7.64-7.68 (m, 2H), 8.59-8.60 (d, 1H); MS (M+H, 281).

The compound had EC$_{50}$ for activation of umami receptor expressed in an HEK293 cell line of 10.3 µM.

Example 16a 5-(2,4-Dimethylphenyl)-1,3,4-oxadiazol-2-amine

To a solution of 2,4-dimethylbenzohydrazide (example 16b) (2 g) in dry dioxane (12 mL) was added cyanic bromide (1.28 g, 12.2 mmol) followed by a solution of NaHCO$_3$ (1.02 g, 12.2 mmol) in water (12 mL). The resulting mixture was stirred 2 hours at rt. The solution was concentrated to ½ volume on vacuum and diluted with water (20 mL). The resulting solid was collected and dried on vacuum to give 5-(2,4-Dimethylphenyl)-1,3,4-oxadiazol-2-amine (1.88 g, 82%) as a white solid. $^1$H NMR (300 MHz, dMSO): δ 2.29 (s, 3H), 2.52 (d, 3H), 7.13 (d, 1H), 7.16 (s, 3H), 7.54-7.56 (d, 1H); MS (M+H, 190).

Example 16b

2,4-dimethylbenzohydrazide

To a solution of methyl 2,4-dimethylbenzoate (2 g, 12.2 mmol) in MeOH (10 mL) was added anhydrous hydrazine (1.95 mL, 61 mmol) and the mixture was heated under reflux for 40 hours. Then the mixture was evaporated and dried under vacuum to give 2,4-dimethylbenzohydrazide as a white solid (2 g, 100%; MS (M+H, 165).

Example 17

3-(Benzylthio)-6-(2,4-dimethylphenyl)pyridazine

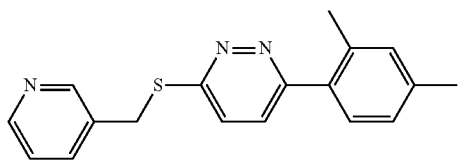 [SMILES: Cc1ccc(-c2ccc(SCc3cccnc3)nn2)c(C)c1]

Prepared in a similar manner to example 13 using 3-(bromomethyl)pyridine hydrobromide 6-(2,4-dimethylphenyl)pyridazine-3(2H)-thione (Example 13a). Yield 39.5 mg (28%). $^1$H NMR (300 MHz, dMSO): δ 2.29 (s, 3H), 2.34 (s, 3H), 4.62 (s, 2H), 7.13-7.17 (m, 2H), 7.31-7.37 (m, 2H), 7.65-7.71 (m, 2H), 7.89-7.90 (d, 1H), 8.45-8.46 (m, 1H), 8.69-8.70 (d, 1H); MS (M+H, 308).

The compound had $EC_{50}$ for activation of umami receptor expressed in an HEK293 cell line of 15.17 μM.

Example 18

2-((5-(4-ethyl-2-methoxyphenyl)-1H-1,2,4-triazol-3-ylthio)methyl)pyridine

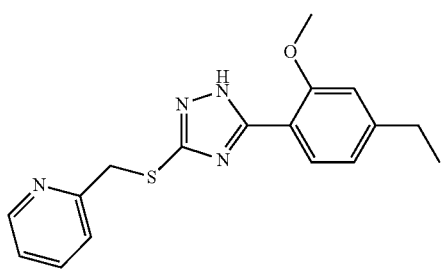 [SMILES: CCc1ccc(-c2nc(SCc3ccccn3)n[nH]2)c(OC)c1]

To a solution of 5-(4-ethyl-2-methoxyphenyl)-2H-1,2,4-triazole-3(4H)-thione (example 18a) (100 mg, 0.43 mmol) in EtOH (2 mL) was added 2-(bromomethyl)pyridine hydrobromide (129 mg, 0.51 mmol). The suspension was heated at 60° C. for 22 h. The reaction mixture was diluted with EtOAc and washed successively with water and brine, dried over MgSO$_4$, filtered and evaporated. The residue was purified on silica gel (Eluent: 5% MeOH in DCM) to give 2-((5-(4-ethyl-2-methoxyphenyl)-1H-1,2,4-triazol-3-ylthio)methyl)pyridine (95 mg) as a white powder (68%). $^1$H NMR (300 MHz, dMSO): δ 1.19-1.22 (t, 3H), 2.63-2.69 (dd, 2H), 3.93 (s, 3H), 4.48 (s, 2H), 6.93-7.03 (m, 2H), 7.25-7.29 (m, 1H), 7.49-7.5 (m, 1H), 7.71-7.75 (m, 1H), 7.93-7.95 (d, 1H), 8.50-8.51 (d, 1H), 13.65 (bs, 1H). MS (M+H, 327).

The compound had $EC_{50}$ for activation of a hT1R1/hT1R3 umami receptor expressed in an HEK293 cell line of 0.05 μM.

Example 18a

5-(4-ethyl-2-methoxyphenyl)-2H-1,2,4-triazole-3(4H)-thione

To a solution of 4-ethyl-2-methoxybenzoic acid (example 18b)(1 g, 6.1 mmol) in pyridine (6 mL) was added EDCI (1.2 g, 6.3 mmol) and the suspension was stirred at r.t. for 2 h. Then thiosemicarbazide (547 mg, 6 mmol) was added and the reaction was stirred at r.t. for 24 h. The mixture was evaporated to dryness and then diluted with water. A white solid was collected and washed with water. The solid was suspended in aq. NaHCO$_3$ (1M, 20 mL) and heated at reflux for 2 days. The suspension was filtered hot and the aqueous solution was cooled in ice and acidified to pH 3 with conc. HCl. The solid was collected washed with water and dried to give 5-(4-ethyl-2-methoxyphenyl)-2H-1,2,4-triazole-3(4H)-thione as a white powder (55%). MS (M+H, 236).

Example 18b

4-Ethyl-2-methoxybenzoic acid

Methyl 4-ethyl-2-methoxybenzoate (example 18c) (2.01 g, 10.3 mmol) was suspended in 1M aq. NaOH (40 mL) and the mixture was stirred at 60° C. overnight. The reaction mixture was cooled to rt and washed with hexanes. The aqueous layer was then separated and acidified with 6N HCl to pH 2. A white precipitate was collected washed with water and dried to give 4-ethyl-2-methoxybenzoic acid (1.8 g, 97%) as a white solid. $^1$H NMR (300 MHz, dMSO): δ 1.16-1.20 (t, 3H), 2.60-2.65 (dd, 2H), 3.80 (s, 3H), 6.82-6.84 (d, 1H), 6.95 (s, 1H), 7.57-7.59 (d, 1H).

Example 18c

Methyl 4-ethyl-2-methoxybenzoate

To a solution of methyl 4-chloro-2-methoxybenzoate (example 18d) (4.16 g, 20.8 mmol) in THF (120 mL) and NMP (12 mL) was added under inert atmosphere Iron(III) acetylacetonate (398 mg, 1.17 mmol) giving a red color. Then EtMgBr (29 ml of 1M solution in ether) was added dropwise under vigorous stirring. The mixture turned dark brown and then violet and then was stirred for 15 more min. The reaction was diluted with ether and quenched upon the addition of aq. HCl (1M, 50 mL). The crude product was extracted with ether and the combined organic layers were successively washed with water and brine, dried over MgSO$_4$, filtered and evaporated. The residue was purified on silica gel (Eluent: 30% EtOAc in hexanes) to give methyl 4-ethyl-2-methoxybenzoate (2.01 g, 50%) as an oil. $^1$H NMR (300 MHz, dMSO): δ 1.20-1.22 (t, 3H), 2.65-2.7 (dd, 2H), 3.9 (s, 3H), 6.8 (s, 1H), 6.97 (m, 1H), 7.7 (m, 1H).

Example 18d

Methyl 4-chloro-2-methoxybenzoate

A suspension of 4-chloro-2-methoxybenzoic acid (5 g, 27 mmol) in MeOH (18 mL) and conc. H$_2$SO$_4$ (1.5 mL) was refluxed overnight. MeOH was evaporated and the residue was extracted to EtOAc and successively washed with water and brine, dried over MgSO$_4$, filtered and evaporated to give methyl 4-chloro-2-methoxybenzoate as a white solid (5.17 g, 96%).

Additional "Triazole" compounds were synthesized (A1-22) or purchased (A23-26 from Asinex, Russia; A27 from Maybridge, England, -) were experimentally tested and found to have a relatively high level of effectiveness as an activator of a hT1R1/hT1R3 umami receptor expressed in an HEK293 cell line. The results of that testing are shown below in Table A.

TABLE A

| | Triazoles | | | |
|---|---|---|---|---|
| Compound No. | Compound | Umami EC$_{50}$ (μM) | Ec$_{50}$ ratio (vs. MSG) | @ (μM) |
| A1 | 2-((5-p-tolyl-2H-1,2,4-triazol-3-ylthio)methyl)pyridine | 0.17 | 2.19 | 0.01 |
| A2 | 2-((5-(2,3-dimethoxyphenyl)-2H-1,2,4-triazol-3-ylthio)methyl)pyridine | 0.18 | 1.9 | 0.01 |
| A3 | 2-((5-(4-methoxy-2-methylphenyl)-2H-1,2,4-triazol-3-ylthio)methyl)pyridine | 0.24 | 2.01 | 0.3 |
| A4 | 2-((5-(2,4-dimethoxyphenyl)-2H-1,2,4-triazol-3-ylthio)methyl)pyridine | 0.37 | 6.22 | 0.1 |

TABLE A-continued

Triazoles

| Compound No. | Compound | Umami EC$_{50}$ (μM) | Ec$_{50}$ ratio (vs. MSG) | @ (μM) |
|---|---|---|---|---|
| A5 | 2-((5-(4-isopropylphenyl)-2H-1,2,4-triazol-3-ylthio)methyl)pyridine | 0.42 | 1.5 | 0.03 |
| A6 | 2-((5-(4-methoxyphenyl)-2H-1,2,4-triazol-3-ylthio)methyl)pyridine | 0.52 | | |
| A7 | 2-((5-(4-ethoxyphenyl)-2H-1,2,4-triazol-3-ylthio)methyl)pyridine | 0.74 | 2.33 | 0.03 |
| A8 | 2-((5-m-tolyl-2H-1,2,4-triazol-3-ylthio)methyl)pyridine | 0.94 | | |
| A9 | 2-((5-(2,4-dimethoxyphenyl)-2H-1,2,4-triazol-3-ylthio)methyl)-5-methylpyridine | 1.07 | | |

TABLE A-continued

Triazoles

| Compound No. | Compound | Umami EC$_{50}$ (μM) | Ec$_{50}$ ratio (vs. MSG) | @ (μM) |
|---|---|---|---|---|
| A10 | 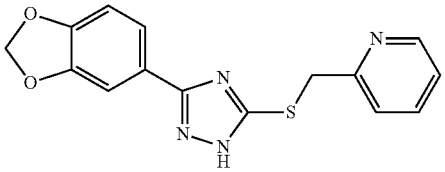 [SMILES: c1ccc(CSc2nc(-c3ccc4c(c3)OCO4)n[nH]2)nc1]<br>2-((5-(benzo[d][1,3]dioxol-5-yl)-2H-1,2,4-triazol-3-ylthio)methyl)pyridine | 1.18 | 6.01 | 0.3 |
| A11 | 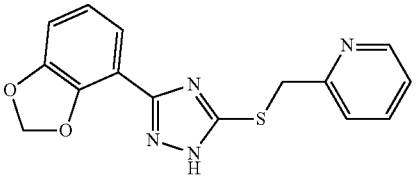 [SMILES: c1ccc(CSc2nc(-c3cccc4c3OCO4)n[nH]2)nc1]<br>2-((5-(benzo[d][1,3]dioxol-4-yl)-2H-1,2,4-triazol-3-ylthio)methyl)pyridine | 1.35 | | |
| A12 | 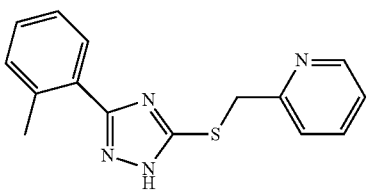 [SMILES: Cc1ccccc1-c1n[nH]c(SCc2ccccn2)n1]<br>2-((5-o-tolyl-2H-1,2,4-triazol-3-ylthio)methyl)pyridine | 1.86 | 1.97 | 0.1 |
| A13 | 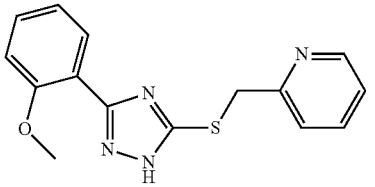 [SMILES: COc1ccccc1-c1n[nH]c(SCc2ccccn2)n1]<br>2-((5-(2-methoxyphenyl)-2H-1,2,4-triazol-3-ylthio)methyl)pyridine | 2.12 | 7.36 | 0.3 |
| A14 | 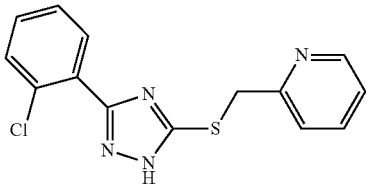 [SMILES: Clc1ccccc1-c1n[nH]c(SCc2ccccn2)n1]<br>2-((5-(2-chlorophenyl)-2H-1,2,4-triazol-3-ylthio)methyl)pyridine | 2.48 | | |
| A15 | 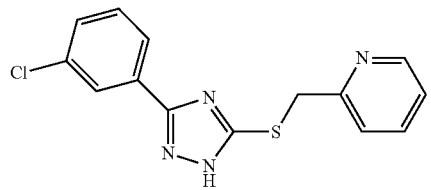 [SMILES: Clc1cccc(-c2n[nH]c(SCc3ccccn3)n2)c1]<br>2-((5-(3-chlorophenyl)-2H-1,2,4-triazol-3-ylthio)methyl)pyridine | 2.54 | 2 | 0.1 |

TABLE A-continued

Triazoles

| Compound No. | Compound | Umami EC$_{50}$ (μM) | Ec$_{50}$ ratio (vs. MSG) | @ (μM) |
|---|---|---|---|---|
| A16 | 2-((5-(3,5-dimethoxyphenyl)-2H-1,2,4-triazol-3-ylthio)methyl)pyridine | 2.58 | 3.16 | 0.3 |
| A17 | 2-((5-phenyl-2H-1,2,4-triazol-3-ylthio)methyl)pyridine | 2.89 | 3.02 | 0.3 |
| A18 | 2-((5-(3,4-dimethoxyphenyl)-2H-1,2,4-triazol-3-ylthio)methyl)pyridine | 4.08 | 2.13 | 0.3 |
| A19 | 2-((5-(2-ethoxyphenyl)-2H-1,2,4-triazol-3-ylthio)methyl)pyridine | 6.49 | 2.01 | 0.3 |
| A20 | 2-(2-(5-(3,5-dimethoxyphenyl)-2H-1,2,4-triazol-3-ylthio)ethyl)pyridine | 7.37 | 4.84 | 0.3 |

TABLE A-continued
Triazoles
| Compound No. | Compound | Umami EC$_{50}$ (μM) | Ec$_{50}$ ratio (vs. MSG) | @ (μM) |
|---|---|---|---|---|
| A21 | 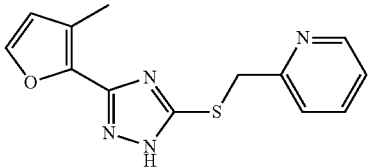 [SMILES: Cc1ccoc1-c1n[nH]c(SCc2ccccn2)n1] 2-((5-(3-methylfuran-2-yl)-2H-1,2,4-triazol-3-ylthio)methyl)pyridine | 9.41 | | |
| A22 | 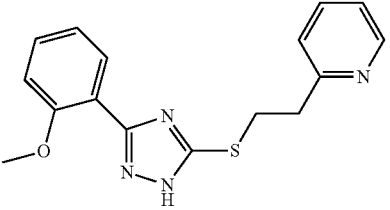 [SMILES: COc1ccccc1-c1n[nH]c(SCCc2ccccn2)n1] 2-(2-(5-(2-methoxyphenyl)-2H-1,2,4-triazol-3-ylthio)ethyl)pyridine | 7.38 | | |
| A23 | 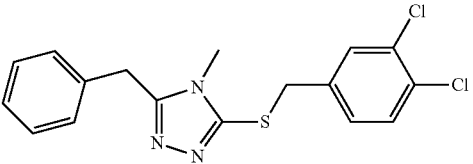 [SMILES: Cn1c(Cc2ccccc2)nnc1SCc1ccc(Cl)c(Cl)c1] 3-benzyl-5-(3,4-dichlorobenzylthio)-4-methyl-4H-1,2,4-triazole | 12.95 | | |
| A24 | 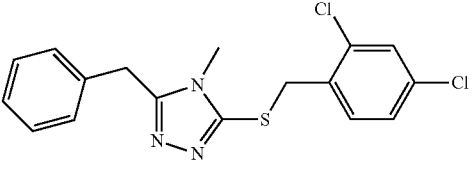 [SMILES: Cn1c(Cc2ccccc2)nnc1SCc1ccc(Cl)cc1Cl] 3-benzyl-5-(2,4-dichlorobenzylthio)-4-methyl-4H-1,2,4-triazole | 6.05 | | |
| A25 | 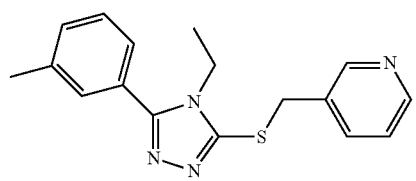 [SMILES: CCn1c(SCc2cccnc2)nnc1-c1cccc(C)c1] 3-((4-ethyl-5-m-tolyl-4H-1,2,4-triazol-3-ylthio)methyl)pyridine | 13.06 | | |

TABLE A-continued

Triazoles

| Compound No. | Compound | Umami EC$_{50}$ (μM) | EC$_{50}$ ratio (vs. MSG) | @ (μM) |
|---|---|---|---|---|
| A26 | 3-(4-ethyl-5-(pyridin-3-ylmethylthio)-4H-1,2,4-triazol-3-yl)naphthalen-2-ol | 1.89 | | |
| A27 | 3-(4-chlorobenzylthio)-4-methyl-5-(thiophen-3-ylmethyl)-4H-1,2,4-triazole | 7.92 | | |

Additional "pyridazine" compounds were purchased (B1-2 from Asinex of Moscow, Russia; B3 from ICN biomedical research of Irvine, Calif.; B4 from Life Chemicals of Burlington, Canada) and experimentally tested and found to have good effectiveness as an activator of a hT1R1/hT1R3 umami receptor expressed in an HEK293 cell line. The results of that testing are shown below in Table B.

TABLE B

Pyridazines

| Compound No. | Compound | Umami EC$_{50}$ (μM) | EC$_{50}$ ratio (vs. MSG) | @ (μM) |
|---|---|---|---|---|
| B1 | 3-(2,3-dihydrobenzo[b][1,4]dioxin-yl)-6-(pyridin-2-ylmethylthio)pyridazine | 0.6 | | |
| B2 | 3-(3,4-dimethoxyphenyl)-6-(pyridin-2-ylmethylthio)pyridazine | 1.7 | | |

TABLE B-continued

Pyridazines

| Compound No. | Compound | Umami EC$_{50}$ (μM) | Ec$_{50}$ ratio (vs. MSG) | @ (μM) |
|---|---|---|---|---|
| B3 | 3-(2,3-dihydrobenzo[b][1,4]dioxin-6-yl)-6-(pyridin-3-ylmethylthio)pyridazine | 8.4 | | |
| B4 | 3-(2,3-dihydrobenzo[b][1,4]dioxin-6-yl)-6-(pyridin-3-ylmethylthio)pyridazine | 3.61 | | |

Additionally a "tetrazole" compound purchased from Ryan Scientific of Isle of Palms, S.C., was experimentally tested and found to have good effectiveness as an activator of a hT1R1/hT1R3 umami receptor expressed in an HEK293 cell line. The result of that testing is shown below in Table C.

TABLE C

Tetrazole

| Compound No. | Compound | Umami EC$_{50}$ (μM) | Ec$_{50}$ ratio (vs. MSG) | @ (μM) |
|---|---|---|---|---|
| C1 | 2-((5-(4-(methylthio)phenyl)-2H-tetrazol-2-yl)methyl)pyridine | 5.91 | | |

Umami/Savory Flavor Experiments Using Human Panelists:

General Panelist Selection: Basic screening of sensory taste testers. Potential panelists were tested for their abilities to rank and rate intensities of solutions representing the five basic tastes. Panelists ranked and rated intensity of five different concentrations of each of the five following compounds: sucrose (sweet), sodium chloride (salty), citric acid (sour), caffeine (bitter), and monosodium glutamate (savory). In order to be selected for participation in testing, panelists needed to correctly rank and rate samples for intensity, with a reasonable number of errors.

Preliminary Taste Tests:

The panelists selected in the above procedure were deemed qualified for performing Preliminary Taste Testing procedures. The preliminary taste tests are used to evaluate new compounds for intensity of basic tastes and off-tastes. A small group of panelists (n=5) taste approximately 5 concentrations of the compound (range typically between 1-100 μM, in half-log cycles, e.g., 1, 3, 10, 30, and 100 μM) in water and in a solution of 12 mM MSG to evaluate enhancement. Panelists rate the five basic tastes (sweet, salty, sour, bitter, and savory) as well as off-tastes (such as chemical, metallic, sulfur) on a labeled magnitude scale. Samples are served in 10 mL portions at room temperature. The purpose of the test is to determine the highest concentration at which there is no objectionable off-taste, and determine if obvious savory taste or enhancement of savory taste exists at any of the concentrations tested.

If the compound is effective and does not have objectionable off-tastes, it is tested with a trained (expert panel) in a larger study.

Trained Panelist Selection:

A trained expert panel was used to further evaluate compounds that had been tested with the preliminary taste test.

Panelists for the trained panel were selected from the larger group of qualifying taste panelists. Panelists were further trained on savory taste by ranking and rating experiments using MSG and IMP combinations. Panelists completed a series of ranking, rating, and difference from reference tests with savory solutions. In ranking and rating experiments, panelists evaluated easy MSG concentrations (0, 6, 18, 36 mM) and more difficult MSG concentrations (3, 6, 12, 18 mM MSG) in water.

Compound testing with Trained Panel: Compounds tested by the trained panel were evaluated in difference from reference experiments. Panelists were given a reference sample (12 mM MSG+100 µM IMP) and asked to rate samples on a scale of −5 to +5 in terms of difference in savory taste from the reference (score: −5=much less savory taste than the reference; 0=same savory taste as the reference; +5=much more savory taste than the reference). Test samples were solutions with varying amounts of MSG, IMP, and the compound. Typically, each session compares the reference sample to numerous test samples. Tests typically included various samples with varying concentrations of MSG and IMP, as well as one blind sample of the reference itself, to evaluate panel accuracy. Results of the taste tests are describe in table 3 and shows that compounds of the invention have been found to provide savory taste or enhancement of the savory taste at 1 uM+MSG when compared to 100 µM IMP+MSG. Compounds were tested against the reference in samples with and without 12 mM MSG. All samples were presented in 10 ml volumes at room temperature. Two sessions were completed for each compound tested to evaluate panel reproducibility.

Taste Test in Product Prototype: could be done similarly as described above.

TABLE D

Savory Taste Test Results

| Compound No. | Chemical Name | Taste Data |
|---|---|---|
| Example 1 | 2-((5-(2-methoxy-4-methylphenyl)-1H-1,2,4-triazol-3-ylthio)methyl)pyridine | 12 mM MSG + 1 µM cpd 1 as strong as 12 mM MSG + 100 µM IMP |
| Example 1 | 2-((5-(2-methoxy-4-methylphenyl)-1H-1,2,4-triazol-3-ylthio)methyl)pyridine | 1 µM cpd 1 (in the absence of MSG) as strong as 12 mM MSG |
| Example 3 | 2-((5-(2,4-dimethylphenyl)-1H-1,2,4-triazol-3-ylthio)methyl)pyridine | 12 mM MSG + 0.3 µM cpd as strong as 12 mM MSG + 100 µM IMP |
| Example 4 | 2-((5-(4-Ethylphenyl)-1H-1,2,4-triazol-3-ylthio)methyl)pyridine | 12 mM MSG + 1 µM cpd as strong as 12 mM MSG + 100 µM IMP |
| Example 4 | 2-((5-(4-Ethylphenyl)-1H-1,2,4-triazol-3-ylthio)methyl)pyridine | 1 µM cpd 4 (in the absence of MSG) as strong as 12 mM MSG |

Example 19

Soup Preparation Using an Ethanol Stock Solution

A compound of the invention is diluted using 200 proof ethanol to 1000× the desired concentration in soup. The compound can be sonicated and/or heated to acheive complete solubility in ethanol. The soup is made by adding 6 g of vegetable bouillon base in 500 mL of hot water in a glass or stoneware bowl. The water is heated to 80° C. The concentration of MSG in the dissolved bouillon is 2.2 g/L and no IMP added. After the bouillon base is dissolved, the ethanol stock solution is added to the soup base. For 500 mL of soup, 0.5 mL of the 1000× ethanol stock is added for a final ethanol concentration of 0.1%. If the ethanol interferes with the taste of the soup, a higher concentration of ethanol stock solution can be prepared provided the compound is soluble.

Example 20

Chip Preparation

A comestibly acceptable carrier composition comprising a compound of Formula (I) is made by mixing the compound of Formula (I) with a salt mixture (typically a mixture of sodium chloride and monosodium glutamate) so that a 1.4% of the salt mixture added w/w to chips would result in the desired concentration of MSG and the compound of Formula (I). For 1 ppm final of the compound on chips, 7 mg of the compound is mixed with 10 g of salt and/or MSG. The mixture is ground using a mortar and pestle until mixed well. The chips are broken into uniform small pieces by using a blender. For each 98.6 g of chips, 1.4 g of the salt mixture is weighed out. The chip pieces are first heated in a microwave for 50 seconds or until warm. The pieces are spread out on a large piece of aluminum foil. The salt mixture is spread evenly over the chips. The chips are then placed in a plastic bag making sure that all the salt is place in the bag as well. The salt mixture and chips are then shaken to ensure that the salt is spread evenly over the chips.

Example 21

Juice Preparation

A compound of Formula (I) is diluted using 200 proof ethanol to 1000 times the desired concentration in a vegetable juice. The alcohol solution of the compound is further blended with natural and/or artificial flavors (including MSG) to make a "key". The flavor key is blended with a portion of vegetable juice concentrate to assure homogeneity. The remainder of the juice concentrate is diluted with water and mixed. Sweeteners, such as HFCS (High Fructose Corn Syrup), aspartame, or sucralose, can be mixed in and blended. The flavor/compound portion is added as a final step, and blended.

Example 22

Spicy Tomato Juice or Bloody Mary Mix

A compound of Formula (I) is added as a dry ingredient to a spice blend that may include MSG, and mixed thoroughly. Spice blend is dispersed into a portion of the tomato paste, blended, and that blended paste is further blended into the remaining paste. The paste is then diluted with water. It may be processed at high temperature for a short time.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of some of the embodiments of the invention being indicated by the following claims.

We claim:

1. A method for modulating the savory taste of a comestible composition comprising combining the comestible composition with a savory flavor modulating amount of at least one compound having the formula:

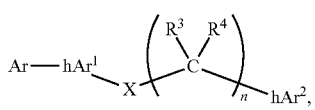

or a comestibly acceptable salt thereof, so as to form a modified comestible composition; wherein i) Ar is a monocyclic or bicyclic aryl or heteroaryl radical comprising one or two aromatic rings independently selected from benzene rings and five or six membered heteroaryl rings, each aromatic ring optionally having one, two, or three $R^{20}$ substituent radicals bound thereto, wherein each $R^{20}$ radical is independently selected from hydroxyl, $NH_2$, SH, halogen, or a $C_1$-$C_4$ organic radical;

ii) $hAr^1$ is a five or six-membered heteroaryl ring radical comprising at least two ring carbon atoms and one to three ring heteroatoms independently selected from O, N, or S, wherein any remaining members of the heteroaromatic ring are independently selected from $CR^6$, N, $NR^7$;

iii) X is O, S, S(O), $SO_2$, $CR^8R^9$, or $NR^{10}$;

iv) n is the integers zero, one, two, or three;

v) $R^3$, $R^4$, $R^8$ and $R^9$ are independently selected from hydrogen, oxygen, hydroxyl, $NH_2$, SH, halogen, or a $C_1$-$C_4$ organic radical, and $R^7$ and $R^{10}$ are independently selected from hydrogen, hydroxyl, or a $C_1$-$C_4$ organic radical, and $R^6$ is hydrogen, halogen, or a $C_1$-$C_4$ organic radical; and vi) $hAr^2$ is a five or six-membered heteroaryl ring having at least one ring carbon atom and at least one ring nitrogen atom, and wherein the remaining members of the heteroaryl ring are independently selected from $CR^{30}$, CH, N, $NR^{31}$, O, and S, wherein the number of $CR^{30}$ is zero, one or two, and each $R^{30}$ is independently selected from hydroxyl, $NH_2$, $NO_2$, SH, $SO_3H$, $P(O)(OH)_2$, a halogen, or a $C_1$-$C_4$ organic radical, and each $R^{31}$ is independently selected from hydrogen, or a $C_1$-$C_4$ organic radical.

2. The method of claim 1, wherein the $R^{20}$ and $R^{30}$ radicals are independently selected from the group consisting of hydroxy, SH, $NH_2$, halogen, alkyl, alkoxyl, alkoxy-alkyl, hydroxyalkyl, haloalkyl, CN, $CO_2H$, CHO, $COR^{21}$, $CO_2R^{21}$, amide, $NHR^{21}$, $NR^{21}R^{21'}$, $R^{21}$, $S(O)R^{21}$, and $SO_2R^{21}$, wherein $R^{21}$ is an alkyl.

3. The method of claim 1, wherein the $R^{20}$ and $R^{30}$ radicals are independently selected from the group consisting of hydrogen, hydroxy, fluoro, chloro, $NH_2$, $NHCH_3$, $N(CH_3)_2$, $CO_2CH_3$, amide, SEt, $SCH_3$, methyl, ethyl, isopropyl, trifluoromethyl, methoxy, ethoxy, isopropoxy, and trifluoromethoxy groups.

4. The method of claim 1, wherein Ar comprises a benzene, pyridyl, pyrazinyl, pyridazinyl, pyrimidinyl, furanyl, thiofuranyl, pyrrolyl, pyrazolyl, oxazolyl, isoxazolyl, benzofuranyl, benzothiofuranyl, or benzopyrrolyl ring.

5. The method of claim 1, wherein $hAr^1$ has the structure:

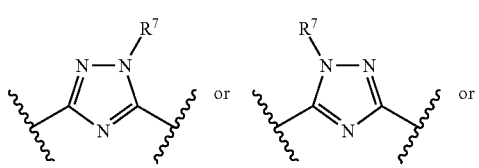

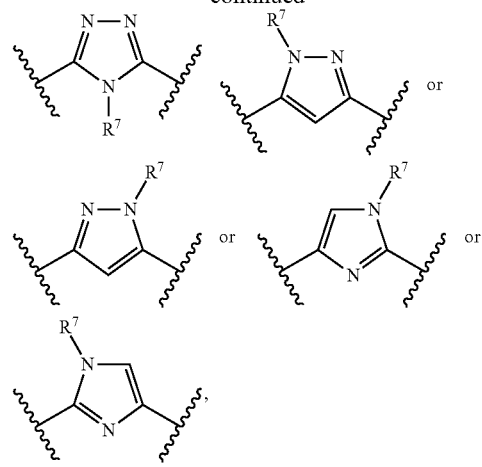

wherein $R^7$ is hydrogen or a $C_1$-$C_4$ organic radical,

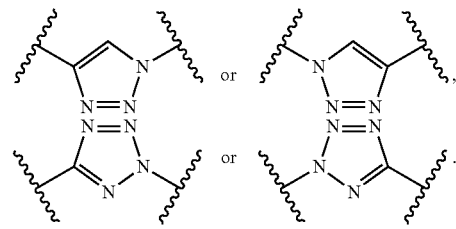

6. The method of claim 1, wherein n is one.
7. The method of claim 1, wherein X is S, NH, or O.
8. The method of claim 1, wherein $R^3$, $R^4$, $R^6$, $R^7$, $R^8$, $R^9$, and $R^{10}$ are hydrogen.
9. The method of claim 1, wherein $hAr^2$ comprises a pyridyl, pyrazinyl, or pyrimidinyl ring.
10. The method of claim 1, wherein the compound has structural Formula (IA):

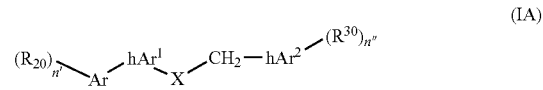

and wherein i) n' is zero, one, two, or three, and each $R^{20}$ is independently selected from the group consisting of hydroxy, SH, $NH_2$, a halogen, or a $C_1$-$C_4$ organic radical, ii) n" is zero, one, or two, and each $R^{30}$ is independently selected from the group consisting of hydroxy, SH, $NH_2$, a halogen, or a $C_1$-$C_4$ organic radical, iii) X is NH, O, S, S(O), $SO_2$, or $CH_2$, iv) Ar is a phenyl, pyridyl, pyrazinyl, pyrimidinyl, furanyl, thiofuranyl, pyrrolyl, benzofuranyl, benzothiofuranyl, or benzopyrrolyl ring, v) $hAr^1$ has the structure:

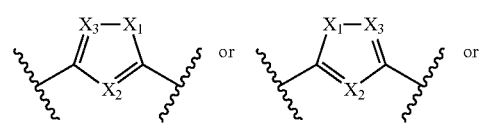

-continued

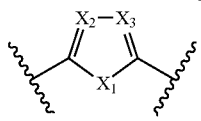

(1) $X_1$ is NH, O, or S,
(2) $X_2$ is N or $CR^6$ wherein $R^6$ is hydrogen, a halogen, or a $C_1$-$C_4$ organic radical,
(3) $X_3$ is N or $CR^6$ wherein $R^6$ is hydrogen, a halogen, or a $C_1$-$C_4$ organic radical, and vi) $hAr^2$ is a a pyridyl, pyrazinyl, or pyrimidinyl ring.

11. The method of claim 10, wherein the $R^{20}$ and $R^{30}$ radicals are independently selected from hydroxy, SH, $NH_2$, a halogen, alkyl, alkoxyl, alkoxy-alkyl, hydroxyalkyl, haloalkyl, CN, $CO_2H$, CHO, $COR^{32}$, $CO_2R^{32}$, amide, $NHR^{32}$, $NR^{32}R^{32'}$ or $SR^{32}$ radical, wherein $R^{32}$ and $R^{32'}$ are independently selected alkyls.

12. The method of claim 10, wherein the $R^{20}$ and $R^{30}$ radicals are independently selected from the group consisting of a hydroxy, fluoro, chloro, $NH_2$, $NHCH_3$, $N(CH_3)_2$, $CO_2CH_3$, amide, SEt, $SCH_3$, methyl, ethyl, isopropyl, trifluoromethyl, methoxy, ethoxy, isopropoxy, and trifluoromethoxy group.

13. The method of claim 10, wherein Ar is a phenyl ring, n' is one or two, and each $R_{20}$ is independently selected from the group consisting of methyl, ethyl, isopropyl, trifluoromethyl, methoxy, trifluoromethoxy, and ethoxy.

14. The method of claim 10, wherein X is S, NH, or O.
15. The method of claim 10, wherein $X_1$ is NH.
16. The method of claim 10, wherein $X_2$ is N or CH.
17. The method of claim 10, wherein $X_3$ is N or CH.
18. The method of claim 10, wherein $X_1$ is NH, and $X_2$ and $X_3$ are N.
19. The method of claim 10, wherein $hAr^2$ has the structure:

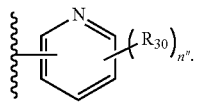

20. The method of claim 19 wherein each $R_{30}$ is independently selected from the group consisting of a hydroxy, fluoro, chloro, $NH_2$, $NHCH_3$, $N(CH_3)_2$, $CO_2CH_3$, amide, SEt, $SCH_3$, methyl, ethyl, isopropyl, trifluoromethyl, methoxy, ethoxy, isopropoxy, and trifluoromethoxy.

21. The method of claim 10, wherein the pyridine radical is a 2-pyridine radical having the structure:

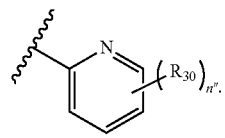

22. The method of claim 21 wherein n" is 0 or 1.
23. The method of claim 1, wherein the compound is selected from the group consisting of:
2-((3-(2,3-dimethoxyphenyl)-1H-1,2,4-triazol-5-ylthio) methyl)pyridine;
2-((5-(2-methoxy-4-methylphenyl)-1H-1,2,4-triazol-3-ylthio)methyl)pyridine;
2-((5-(2,4-dimethylphenyl)-1H-1,2,4-triazol-3-ylthio)methyl)pyridine;
2-((5-(4-Ethylphenyl)-1H-1,2,4-triazol-3-ylthio)methyl) pyridine;
2-((5-(4,5-dimethylfuran-2-yl)-1H-1,2,4-triazol-3-ylthio) methyl)pyridine;
2-((5-(4-Ethyl-2-methylphenyl)-1H-1,2,4-triazol-3-ylthio)methyl)pyridine; and
2-((5-(4-ethyl-2-methoxyphenyl)-1H-1,2,4-triazol-3-ylthio)methyl)pyridine.

24. The method of claim 1 wherein the comestible composition comprises at least a savory flavor modulating amount of monosodium glutamate.

25. The method of claim 1, wherein the modified comestible composition is a food or beverage for human consumption.

26. The method of claim 1, wherein the compound is present in the modified comestible composition at a concentration from about 0.01 ppm to about 30 ppm.

27. The method of claim 1, wherein the compound is present in the modified comestible composition in a concentration from about 0.1 ppm to about 3 ppm.

* * * * *